US011471468B2

(12) United States Patent
Kazmi et al.

(10) Patent No.: US 11,471,468 B2
(45) Date of Patent: Oct. 18, 2022

(54) METHODS AND SYSTEMS FOR CONDITIONING OF PARTICULATE CRYSTALLINE MATERIALS

(71) Applicant: Pearl Therapeutics, Inc., Redwood City, CA (US)

(72) Inventors: Ali Kazmi, San Francisco, CA (US); David Lechuga-Ballesteros, San Jose, CA (US); Herman E. Snyder, West Lafayette, IN (US); James Ivey, Edmonton (CA); Reinhard Vehring, Edmonton (CA); Jason H. Speck, Dublin, CA (US); Sarvajna Dwivedi, Redwood City, CA (US)

(73) Assignee: Pearl Therapeutics, Inc., Redwood City, CA (US)

( * ) Notice: Subject to any disclaimer, the term of this patent is extended or adjusted under 35 U.S.C. 154(b) by 99 days.

(21) Appl. No.: 16/777,340

(22) Filed: Jan. 30, 2020

(65) Prior Publication Data

US 2020/0368251 A1 Nov. 26, 2020

Related U.S. Application Data

(63) Continuation of application No. 15/873,779, filed on Jan. 17, 2018, now abandoned, which is a continuation of application No. 14/213,834, filed on Mar. 14, 2014, now abandoned.

(60) Provisional application No. 61/799,956, filed on Mar. 15, 2013.

(51) Int. Cl.
*A61K 31/56* (2006.01)
*B02C 19/06* (2006.01)
*A61K 31/537* (2006.01)
*A61K 31/58* (2006.01)
*A61K 31/7016* (2006.01)
*A61K 9/14* (2006.01)
*A61K 31/40* (2006.01)

(52) U.S. Cl.
CPC ............... *A61K 31/56* (2013.01); *A61K 9/14* (2013.01); *A61K 31/40* (2013.01); *A61K 31/537* (2013.01); *A61K 31/58* (2013.01); *A61K 31/7016* (2013.01); *B02C 19/06* (2013.01)

(58) Field of Classification Search
CPC ...................................... A61K 31/56
See application file for complete search history.

(56) References Cited

U.S. PATENT DOCUMENTS

| 2,956,062 A | 10/1960 | Lunsford |
| 3,175,299 A | 3/1965 | Boucher |
| 3,929,768 A | 12/1975 | Brattsand et al. |
| 3,994,974 A | 11/1976 | Murakami et al. |
| 4,187,301 A | 2/1980 | Edwards |
| 4,335,121 A | 6/1982 | Phillipps et al. |
| 4,472,393 A | 9/1984 | Shapiro |
| 4,590,206 A | 5/1986 | Forrester et al. |
| 4,992,474 A | 2/1991 | Skidmore et al. |
| 5,126,375 A | 6/1992 | Skidmore et al. |
| 5,225,445 A | 7/1993 | Skidmore et al. |
| 5,610,163 A | 3/1997 | Banholzer et al. |
| 5,612,053 A | 3/1997 | Baichwal et al. |
| 5,654,314 A | 8/1997 | Banholzer et al. |
| 5,684,199 A | 11/1997 | Francotte |
| 5,707,634 A | 1/1998 | Schmitt |
| 5,709,884 A | 1/1998 | Trofast et al. |
| 5,727,333 A | 3/1998 | Folan |
| 5,833,891 A | 11/1998 | Subramaniam et al. |
| 5,851,453 A | 12/1998 | Hanna et al. |
| 5,858,410 A | 1/1999 | Muller et al. |
| 5,874,063 A | 2/1999 | Briggner et al. |
| 5,886,200 A | 3/1999 | Kwok et al. |
| 5,889,015 A | 3/1999 | Sequeira et al. |
| 5,928,469 A | 7/1999 | Franks et al. |
| 6,030,604 A | 2/2000 | Trofast |
| 6,040,344 A | 3/2000 | Gao et al. |
| 6,054,488 A | 4/2000 | Oliver et al. |
| 6,057,307 A | 5/2000 | Sequeira et al. |
| 6,057,581 A | 5/2000 | Doan |
| 6,063,138 A | 5/2000 | Hanna et al. |
| 6,068,832 A | 5/2000 | Berry et al. |
| 6,129,905 A | 10/2000 | Cutie |
| 6,177,560 B1 | 1/2001 | Heggie et al. |
| 6,258,341 B1 | 7/2001 | Foster et al. |
| 6,260,549 B1 | 7/2001 | Sosiak |
| 6,309,623 B1 | 10/2001 | Weers et al. |
| 6,309,671 B1 | 10/2001 | Foster et al. |
| 6,358,530 B1 | 3/2002 | Eljamal et al. |
| 6,365,581 B1 | 4/2002 | Sequeira et al. |
| 6,372,258 B1 | 4/2002 | Platz et al. |
| 6,433,027 B1 | 8/2002 | Bozung et al. |

(Continued)

FOREIGN PATENT DOCUMENTS

| AU | 642913 B2 | 4/1991 |
| AU | 775588 B2 | 12/2000 |

(Continued)

OTHER PUBLICATIONS

Cook et al., "Process Drying Practice," 1991 (4 pages).

(Continued)

*Primary Examiner* — Shaojia A Jiang
*Assistant Examiner* — Everett White
(74) *Attorney, Agent, or Firm* — Seed IP Law Group LLP

(57) ABSTRACT

Methods and systems for the preparation of conditioned micronized active agents. Additionally, methods and systems for in-process conditioning of micronized active agent particles and compositions comprising conditioned micronized materials.

29 Claims, 20 Drawing Sheets

(56) References Cited

U.S. PATENT DOCUMENTS

| | | |
|---|---|---|
| 6,433,040 B1 | 8/2002 | Dellamary et al. |
| 6,451,285 B2 | 9/2002 | Blondino et al. |
| 6,455,524 B1 | 9/2002 | Bozung et al. |
| RE37,872 E | 10/2002 | Franks et al. |
| 6,475,467 B1 | 11/2002 | Keller et al. |
| 6,518,239 B1 | 2/2003 | Kuo et al. |
| 6,537,524 B1 | 3/2003 | Hassan et al. |
| 6,565,885 B1 | 5/2003 | Tarara et al. |
| 6,630,466 B2 | 10/2003 | Bozung et al. |
| 6,638,495 B2 | 10/2003 | Weers et al. |
| 6,667,344 B2 | 12/2003 | Banerjee et al. |
| 6,677,322 B2 | 1/2004 | Sequeira et al. |
| 6,677,323 B2 | 1/2004 | Sequeira et al. |
| 6,719,994 B2 | 4/2004 | Meoli et al. |
| 6,777,423 B2 | 8/2004 | Banholzer et al. |
| 6,814,953 B2 | 11/2004 | Banerjee et al. |
| 6,908,928 B2 | 6/2005 | Banholzer et al. |
| 6,942,821 B2 | 9/2005 | Dayrit et al. |
| 6,946,117 B1 | 9/2005 | Schutt et al. |
| 6,964,759 B2 | 11/2005 | Lewis et al. |
| 7,067,502 B2 | 6/2006 | Hassan et al. |
| 7,186,401 B2 | 3/2007 | Keller et al. |
| 7,205,343 B2 | 4/2007 | Dellamary et al. |
| 7,229,607 B2 | 6/2007 | Bannister et al. |
| 7,244,742 B2 | 7/2007 | Pieper et al. |
| RE39,820 E | 9/2007 | Banholzer et al. |
| 7,273,604 B2 | 9/2007 | Hills et al. |
| 7,306,787 B2 | 12/2007 | Tarara et al. |
| 7,393,544 B2 | 7/2008 | Dellamary et al. |
| 7,442,388 B2 | 10/2008 | Weers et al. |
| 7,566,705 B2 | 7/2009 | Hassan et al. |
| 7,628,978 B2 | 12/2009 | Weers et al. |
| 7,736,670 B2 | 6/2010 | Staniforth et al. |
| 7,790,145 B2 | 9/2010 | Weers et al. |
| 7,915,303 B2 | 3/2011 | Baxter |
| 7,985,766 B2 | 7/2011 | Goede et al. |
| 8,048,451 B2 | 11/2011 | Staniforth et al. |
| 8,048,910 B2 | 11/2011 | Maus et al. |
| 8,080,263 B2 | 12/2011 | Dellamary et al. |
| 8,168,223 B1 | 5/2012 | Tarara et al. |
| 8,246,934 B2 | 8/2012 | Weers et al. |
| 8,252,268 B2 | 8/2012 | Slowey et al. |
| 8,303,991 B2 | 11/2012 | Staniforth et al. |
| 8,324,266 B2 | 12/2012 | Vehring et al. |
| 8,435,567 B2 | 5/2013 | Staniforth et al. |
| 8,703,806 B2 | 4/2014 | Vehring et al. |
| 2002/0188281 A1 | 12/2002 | Dellamary et al. |
| 2003/0018019 A1 | 1/2003 | Meade et al. |
| 2003/0068280 A1 | 4/2003 | Bannister et al. |
| 2003/0114428 A1 | 6/2003 | Sequeira et al. |
| 2004/0081584 A1 | 4/2004 | Doyrit et al. |
| 2004/0081627 A1 | 4/2004 | Jinks et al. |
| 2004/0101483 A1 | 5/2004 | Muller-Walz et al. |
| 2004/0170568 A1 | 9/2004 | Weers et al. |
| 2005/0042174 A1 | 2/2005 | Nilsson et al. |
| 2005/0080052 A1 | 4/2005 | Hills et al. |
| 2005/0121026 A1 | 6/2005 | Nilsson et al. |
| 2005/0175548 A1 | 8/2005 | Goede et al. |
| 2005/0207986 A1 | 9/2005 | Schutt et al. |
| 2005/0255049 A1 | 11/2005 | Slowey et al. |
| 2005/0287077 A1 | 12/2005 | Creazzo et al. |
| 2006/0148693 A1 | 7/2006 | Wollin |
| 2006/0159629 A1 | 7/2006 | Tarara et al. |
| 2006/0165606 A1 | 7/2006 | Tarara et al. |
| 2006/0252815 A1 | 11/2006 | Goede et al. |
| 2006/0257324 A1 | 11/2006 | Lewis et al. |
| 2006/0269484 A1 | 11/2006 | Knopeck et al. |
| 2007/0104658 A1 | 5/2007 | Batycky et al. |
| 2007/0122351 A1 | 5/2007 | Kunka et al. |
| 2007/0193577 A1 | 8/2007 | Keller |
| 2007/0196285 A1 | 8/2007 | Maus et al. |
| 2007/0212405 A1 | 9/2007 | Dellamary et al. |
| 2007/0270481 A1 | 11/2007 | Goede et al. |
| 2008/0125407 A1 | 5/2008 | Chu et al. |
| 2008/0220073 A1 | 9/2008 | Bannister et al. |
| 2008/0226564 A1 | 9/2008 | Weers et al. |
| 2008/0227690 A1 | 9/2008 | Schmitke et al. |
| 2008/0233194 A1 | 9/2008 | Dellamary et al. |
| 2008/0267886 A1 | 10/2008 | Collingwood |
| 2008/0274189 A1 | 11/2008 | Collingwood et al. |
| 2008/0279948 A1 | 11/2008 | Collingwood et al. |
| 2008/0286363 A1 | 11/2008 | Collingwood et al. |
| 2008/0300226 A1 | 12/2008 | Goede et al. |
| 2008/0317862 A1 | 12/2008 | Collingwood et al. |
| 2009/0088408 A1 | 4/2009 | Meade et al. |
| 2009/0130026 A1 | 5/2009 | Lewis et al. |
| 2009/0298802 A1 | 12/2009 | Sequeira et al. |
| 2010/0034890 A1 | 2/2010 | Clarke et al. |
| 2010/0197719 A1 | 8/2010 | Bozung et al. |
| 2010/0329984 A1 | 12/2010 | Weers et al. |
| 2011/0023876 A1 | 2/2011 | Vehring et al. |
| 2011/0132356 A1 | 6/2011 | Vehring et al. |
| 2011/0132357 A1 | 6/2011 | Vehring et al. |
| 2011/0135737 A1 | 6/2011 | Vehring et al. |
| 2012/0024554 A1 | 2/2012 | Boehm et al. |
| 2012/0039817 A1 | 2/2012 | Vehring et al. |
| 2012/0039952 A1 | 2/2012 | Vehring et al. |
| 2012/0325942 A1 | 12/2012 | Lustig et al. |
| 2013/0092160 A1 | 4/2013 | Vehring et al. |
| 2014/0275517 A1 | 9/2014 | Kazmi et al. |

FOREIGN PATENT DOCUMENTS

| | | |
|---|---|---|
| CA | 2 442 415 A1 | 10/2002 |
| CA | 2 479 638 A1 | 10/2003 |
| CA | 2 495 454 A1 | 3/2004 |
| CA | 2 527 178 A1 | 12/2004 |
| CA | 2 607 391 A1 | 11/2006 |
| CN | 1170356 A | 1/1998 |
| DE | 10214264 A1 | 10/2003 |
| EP | 0 416 950 A1 | 3/1991 |
| EP | 0 416 951 A1 | 3/1991 |
| EP | 0 418 716 A1 | 3/1991 |
| EP | 1 621 197 A2 | 4/2003 |
| EP | 1 408 967 B1 | 4/2004 |
| EP | 1 530 471 B1 | 5/2005 |
| EP | 1 570 861 A2 | 9/2005 |
| EP | 1 651 270 B1 | 3/2007 |
| EP | 1 894 568 A1 | 3/2008 |
| EP | 1 718 336 B1 | 6/2008 |
| EP | 1 651 221 B1 | 1/2009 |
| EP | 2 036 572 A1 | 3/2009 |
| EP | 1 971 369 B1 | 8/2009 |
| EP | 2 098 248 A1 | 9/2009 |
| EP | 1 755 590 B1 | 8/2011 |
| EP | 1 651 224 B1 | 10/2011 |
| EP | 1 019 021 B2 | 12/2012 |
| EP | 2 037 879 B1 | 5/2013 |
| JP | 2000-513340 A | 10/2000 |
| JP | 2006-512044 A | 4/2006 |
| JP | 2007-520506 A | 7/2007 |
| JP | 2007-520508 A | 7/2007 |
| JP | 2008-503500 A | 2/2008 |
| JP | 2008-521788 A | 6/2008 |
| JP | 2008-534611 A | 8/2008 |
| JP | 2012-513311 A | 6/2012 |
| RU | 2 319 512 C2 | 3/2008 |
| WO | 1986/003750 A1 | 7/1986 |
| WO | 1991/014468 A1 | 10/1991 |
| WO | 92/004365 A1 | 3/1992 |
| WO | 92/016528 A1 | 10/1992 |
| WO | 93/011773 A1 | 6/1993 |
| WO | 95/005805 A1 | 3/1995 |
| WO | 95/015151 A1 | 6/1995 |
| WO | 96/019198 A1 | 6/1996 |
| WO | 96/032149 A1 | 10/1996 |
| WO | 96/032344 A1 | 10/1996 |
| WO | 97/038741 A1 | 10/1997 |
| WO | 97/039758 A1 | 10/1997 |
| WO | 97/044080 A1 | 11/1997 |
| WO | 98/041193 A1 | 9/1998 |
| WO | 99/015182 A1 | 4/1999 |
| WO | 99/16422 A1 | 4/1999 |
| WO | 99/54048 | 10/1999 |

(56) References Cited

FOREIGN PATENT DOCUMENTS

| | | | |
|---|---|---|---|
| WO | 00/032165 A1 | 6/2000 |
| WO | 00/036915 A1 | 6/2000 |
| WO | 00/053157 A1 | 9/2000 |
| WO | 00/053187 A1 | 9/2000 |
| WO | 00/061108 A1 | 10/2000 |
| WO | 00/069468 A1 | 11/2000 |
| WO | 01/00312 A1 | 1/2001 |
| WO | 01/004118 A2 | 1/2001 |
| WO | 01/054664 A1 | 8/2001 |
| WO | 01/076575 A2 | 10/2001 |
| WO | 02/078671 A1 | 10/2002 |
| WO | 02/085326 A2 | 10/2002 |
| WO | 03/075854 A2 | 9/2003 |
| WO | 2004/014293 A2 | 2/2004 |
| WO | 2004/060344 A2 | 7/2004 |
| WO | 2004/105759 A2 | 12/2004 |
| WO | 2005/000267 A2 | 1/2005 |
| WO | 2005/013994 A1 | 2/2005 |
| WO | 2005/014005 A1 | 2/2005 |
| WO | 2005/074900 A2 | 8/2005 |
| WO | 2005/105043 A2 | 11/2005 |
| WO | 2005/110402 A1 | 11/2005 |
| WO | 2006/114379 A1 | 11/2006 |
| WO | 2006/128847 A2 | 12/2006 |
| WO | 2007/009164 A1 | 1/2007 |
| WO | 2007/057219 A1 | 5/2007 |
| WO | 2007/057221 A1 | 5/2007 |
| WO | 2007/057222 A1 | 5/2007 |
| WO | 2007/057223 A1 | 5/2007 |
| WO | 2007/095041 A1 | 8/2007 |
| WO | 2007/134964 A1 | 11/2007 |
| WO | 2008/000482 A1 | 1/2008 |
| WO | 2008/014161 A2 | 1/2008 |
| WO | 2008/025787 A2 | 3/2008 |
| WO | 2008/102128 A2 | 8/2008 |
| WO | 2009/095681 A2 | 8/2009 |
| WO | 2010/097188 A1 | 9/2010 |
| WO | 2010/138862 A2 | 12/2010 |
| WO | 2010/138868 A2 | 12/2010 |
| WO | 2010/138884 A2 | 12/2010 |
| WO | 2012/051426 A1 | 4/2012 |
| WO | 2012/110770 A2 | 8/2012 |
| WO | 2012/120284 A1 | 9/2012 |
| WO | 2012/158166 A1 | 11/2012 |

OTHER PUBLICATIONS

Masters, "Spray Drying Handbook," Third Edition, pp. 140-162, 1979 (14 pages).
U.S. Appl. No. 61/799,956, "Methods and Systems for Conditioning of Micronized Crystalline Materials and Associated Compositions," filed Mar. 15, 2013, 48 pages.
"Guidance for Industry: Nasal Spray and Inhalation Solution, Suspension, and Spray Drug Products—Chemistry, Manufacturing, and Controls Documentation," retrieved on Feb. 19, 2014 from http://www.fda.gov/downloads/drugs/guidanceComplianceRegulatoryInformation/Guidance/ucm070575.pdf, U.S. Department of Health and Human Services, Food and Drug Administration, Center for Drug Evaluation and Research, pp. 13-14, Jul. 2002, 48 pages.
Applicant Initiated Interview Summary, dated Aug. 2, 2012, for U.S. Appl. No. 13/281,726, 6 pages.
Applicant Initiated Interview Summary, dated Dec. 12, 2012, for U.S. Appl. No. 12/790,448, 3 pages.
Applicant Initiated Interview Summary, dated Dec. 20, 2012, for U.S. Appl. No. 12/790,605, 3 pages.
Applicant Initiated Interview Summary, dated Feb. 22, 2013, for co-pending U.S. Appl. No. 12/790,448, 3 pages.
Applicant Initiated Interview Summary, dated Jan. 30, 2012, for corresponding U.S. Appl. No. 12/790,671, 3 pages.
Applicant Initiated Interview Summary, dated May 22, 2012, for corresponding U.S. Appl. No. 12/790,671, 3 pages.
Applicant Initiated Interview Summary, dated Oct. 28, 2013, for U.S. Appl. No. 13/692,904, 3 pages.
Applicant Initiated Interview Summary, dated Sep. 27, 2012, for U.S. Appl. No. 13/281,726, 3 pages.
Applicant Initiated Interview Summary, dated Apr. 9, 2014, for U.S. Appl. No. 12/790,605, 2 pages.
Applicant Initiated Interview Summary, dated May 23, 2012, for corresponding U.S. Appl. No. 12/790,605, 3 pages.
Australian Examination Report, dated Jan. 29, 2018, for corresponding Australian Patent Application No. 2014228414, 2 pages.
Baculard, "Place du Bronchodual® dans le traitement de fond de l'asthme de l'enfant," *Arch Péditar* 2(Suppl 2):149s-153s, 1995.
Barnes, "Chronic obstructive pulmonary disease: new opportunities for drug development," *Trends in Pharmacological Sciences* 19:415-423, 1998.
Barnes, "Efficacy of Inhaled Corticosteroids in Asthma," *Allergy Clin Immunol* 102:531-538 1998.
Beck, "Utilisation du bromure d'ipratropium par voie inhalée pour de traitement de l'asthme aigu chez l'enfant Expérience Clinique," *Arch Pédiatar* 2(Suppl 2):145s-148s, 1995.
Blondino et al., "Surfactant Dissolution and Water Solubilization in Chlorine-Free Liquified Gas Propellants," pp. 935-945, 1998.
Braga et al., "Making crystals from crystals: a green route to crystal engineering and polymorphism," *Chem Comm*, pp. 3635-3645, 2005.
Brambilla et al., "Modulation of aerosol clouds produced by pressurised inhalation aerosols," *International Journal of Pharmaceutics* 186:53-61, 1999.
Capraz et al., "The Effect of Inhaled Budesonide and Formoterol on Bronchial Remodeling and HRCT Features in Young Asthmatics," *Lung* 185:89-96, 2007.
Cazzola et al., "Incremental Benefit of Adding Oxitropium Bromide to Formoterol in Patients with Stable COPD," *Pulmonary Pharmacology & Therapeutics* 12:267-271, 1999.
Chinese Office Action, dated Jan. 16, 2015, for corresponding Chinese Patent Application No. 201080033310.3, 9 pages.
Chinese Office Action, dated Jun. 23, 2017, for corresponding Chinese Patent Application No. 201480026439.X, 20 pages (with English translation).
Chinese Second Office Action, dated Apr. 8, 2018, for corresponding Chinese Patent Application No. 201480026439.X, 7 pages (with English translation).
Colombian Patent Application No. 15245664, Official Action, dated Dec. 30, 2016, 12 pages (translation only).
Cydulka et al., "Effects of Combined Treatment with Glycopyrrolate and Albuterol in Acute Exacerbation of Chronic Obstructive Pulmonary Disease," *Annals of Emergency Medicine* 25:470-473, 1995.
Da Rocha et al., "Science and Technology of Pressurized Metered-Dose Inhalers," *Controlled Pulmonary Drug Delivery*, Chapter 8, pp. 165-201, 2011.
Dellamary et al., "Hollow Porous Particles in Metered Dose Inhalers," *Pharmaceutical Research* 17(2):168-174, 2000.
Drugs Information Online, "FDA Approves Symbicort: Astrazeneca's Symbicort (budesonide/formoterol) Treatment For Asthma Approved by The FDA," retrieved on Oct. 28, 2013, from www.Drugs.com, Jul. 22, 2006, 2 pages.
Duddu et al., "Improved Lung Delivery from a Passive Dry Powder Inhaler Using an Engineered PulmoSphere Powder," *Pharmaceutical Research* 19(5):689-695 2002.
Encyclopedia of Medicament, M., RLS, 2001, p. 952, article formoterol, pp. 642-643, article Oxys. (with English Translation).
Hansel et al., "Glycopyrrolate Causes Prolonged Bronchoprotection and Bronchodilatation in Patients with Asthma," *Chest* 128:1974-1979, 2005.
Hartman et al., "The Efficiency and Stability of a Novel Lipid-based Budesonide Metered Dose Inhaler Formulation Utilizing HFA," AAPS Annual Meeting and Exposition, Salt Lake City, UT, Oct. 26-30, 2003, 1 page.
Hirst et al., "In Vivo Lung Deposition of Hollow Porous Particles from a Pressurized Metered Dose Inhaler," *Pharmaceutical Research* 19(3):258-264, 2002.

(56) References Cited

OTHER PUBLICATIONS

Hoye et al., "Measurement and Correlation of Solute Solubility in HFA-134a/Ethanol Systems," *International Journal of Pharmaceutics* 362:184-188, 2008.
International Preliminary Report on Patentability, Application No. PCT/US2014/029489, dated Sep. 15, 2015, 5 pages.
International Preliminary Report on Patentability, dated Nov. 29, 2011, for International Application No. PCT/US2010/036650, 10 pages.
International Preliminary Report on Patentability, dated Nov. 29, 2011, for International Application No. PCT/US2010/036676, 9 pages.
International Preliminary Report on Patentability, dated Nov. 19, 2013, for International Application No. PCT/US2011/036868, 8 pages.
International Preliminary Report on Patentability, dated Dec. 8, 2011, for International Application No. PCT/US2010/036659, 11 pages.
International Search Report, dated Aug. 12, 2011, for International Application No. PCT/US2011/036868, 8 pages.
International Search Report, dated Oct. 4, 2013, for corresponding Australian Patent Application No. 2010253770, 4 pages.
International Search Report, dated Feb. 25, 2011, for International Application No. PCT/US2010/036650, 5 pages.
International Search Report, dated Feb. 25, 2011, for International Application No. PCT/US2010/036659, 5 pages.
International Search Report, dated Feb. 25, 2011, for International Application No. PCT/US2010/036676, 5 pages.
International Search Report, dated May 20, 2014, for corresponding International Application No. PCT/US2014/029489, 9 pages.
International Search Report, dated Sep. 2, 2014, for corresponding International Application No. PCT/US/2014039234, 12 pages.
James et al., "The surface characterisation and comparison of two potential sub-micron, sugar bulking excipients for use in low-dose, suspension formulations in metered dose inhalers," *International Journal of Pharmaceutics* 361(1-2):209-221, 2008.
Japanese Office Action, dated Apr. 28, 2015, for corresponding Japanese Application No. 2012-513314, 8 pages. (with English Translation).
Japanese Office Action, dated Dec. 16, 2014, for corresponding Japanese Patent Application No. 2012-513319, 4 pages. (English Translation Only).
Japanese Office Action, dated Dec. 19, 2017, for corresponding Japanese Patent Application No. 2016-503111, 5 pages (with English Translation).
Japanese Office Action, dated Jan. 27, 2015, for corresponding Japanese Patent Application No. YTM/PP15-0004, 5 pages. (with English Translation).
Japanese Office Action, dated Jul. 1, 2014, for corresponding Japanese Patent Application No. 2012-513319, 8 pages.
Johnson et al., "Effect of Inhaled glycopyrrolate and atropine in asthma. Precipitated by exercise and cold air inhalation," *Chest* 85(3):325-328, 1984.
Lechuga-Ballessteros et al., "Residual Water in Amorphous Solids, Measurement and Effects on Stability," In Progress in Amorphous Food and Pharmaceutical Systems, Levine, H., Ed. The Royal Society of Chemistry; London, pp. 275-316, 2002.
Lechuga-Ballesteros et al., "Compositions, Methods and Systems for Respiratory Delivery of Three or More Active Agents," U.S. Appl. No. 14/285,435, filed May 22, 2014, 92 pages.
Leckie et al., "Novel Therapy for COPD," *Exp. Opin. Invest. Drugs* 9(1):3-23, 2000.
Mahler et al., "Effectiveness of Fluticasone Propionate and Salmeterol Combination Delivered via the Diskus Device in the Treatment of Chronic Obstructive Pulmonary Disease," *Am J Respir Crit Care Med* 166:1084-1091, 2002.
Miller, "Qualitative Effects of Water on Suspension Aerosol Formulations," *Respiratory Drug Delivery*, CRC Press, p. 250, 1990, 3 pages.

Newhouse et al., "Inhalation of a Dry Powder Tobramycin PulmoSphere Formulation in Healthy Volunteers," *Chest* 124:360-366, 2003.
Office Action, dated Aug. 1, 2014, for corresponding Japanese Patent Application No. 2012-513319, 8 pages. (with English Translation).
Office Action, dated Jul. 11, 2014, for corresponding Russian Application No. 2011152960, 8 pages.
Office Action, dated Jun. 27, 2014, for corresponding Chinese Patent Application No. 201080033310.3, 17 pages. (with English Translation).
Panettieri et al., "Comparison of the efficacy and safety of arformoterol 15 microg twice daily and arformoterol 30 microg once daily in CORD: a single-dose, multicenter, randomized, modified-blind, two crossover study," *Clin. Ther.* 31(8):1716-1723, Aug. 2009. (Abstract Only).
Ridder et al., "Surfactant solubility and aggregate orientation in hydrofluoroalkanes," *International Journal of Pharmaceutics* 295:57-65, 2005.
Rogueda, "Novel hydrofluoroalkane suspension formulations for respiratory drug delivery," *Expert Opin. Drug Deliv.* 2(4):625-638, 2005.
Russian Office Action, dated Feb. 26, 2014, for corresponding Russian Application No. 2011154083/15, 6 pages.
Russian Office Action, dated Mar. 23, 2018, for corresponding Russian Application No. 2015144286/15, 14 pages.
Russian Office Action, dated May 27, 2015, for corresponding Russian Application No. 20111154148/15(081430), 9 pages. (English Translation Only).
Russian Office Action, dated May 7, 2015, received May 13, 2015, for corresponding Russian Application No. 2013155903/15(087185), 12 pages. (with English Translation).
Schroeckenstein et al., "Twelve-hour bronchodilation in asthma with a single aerosol dose of the anticholinergic compound glycopyrrolate," *J Allergy Clin. Immunol.* 82(1):115-119, 1988.
Seddon, "Pseudopolymorph: a Polemic," *Crystal Growth & Design* 4(6):1087, 2004, 2 pages.
Singapore Patent Application No. 11201507286Q, Examination Report, dated Feb. 28, 2017, 11 pages.
Singh et al., "NVA237, a once-daily inhaled antimuscarin moderate-to-severe COPD," presented at the American Thoracic Society International Conference, San Diego, California, May 19-24, 2006, poster, 2 pages.
Skorodin, "Pharmacotherapy for Asthma and Chronic Obstructive Pulmonary Disease," *Arch. Intern. Med.* 153:814-828, 1993.
Tarara et al., "Characterization of Suspension-Based Metered Dose Inhaler Formulations Composed of Spray-Dried Budesonide Microcrystals Dispersed in HFA-134a," *Pharmaceutical Research* 21(9):1607-1614, 2004.
Troy (Eds.), *The Science and Practice of Pharmacy*, 21st Edition, Part 2: Pharmaceutics, Table 16-1, Lippincott, Williams & Wilkins, 2006, p. 212, 3 pages.
Vehring et al., "Compositions for Pulimonary Delivery of Long-Acting Muscarinic Antagonists and Associated Methods and Systems," Advisory Action, dated Feb. 1, 2013, for co-pending U.S. Appl. No. 12/790,448, 2 pages.
Vehring et al., "Compositions for Pulimonary Delivery of Long-Acting Muscarinic Antagonists and Associated Methods and Systems," Office Action, dated May 7, 2012, for co-pending U.S. Appl. No. 12/790,448, 30 pages.
Vehring et al., "Compositions for Pulimonary Delivery of Long-Acting Muscarinic Antagonists and Associated Methods and Systems," Office Action, dated Oct. 16, 2012, for co-pending U.S. Appl. No. 12/790,448, 18 pages.
Vehring et al., "Compositions for Pulimonary Delivery of Long-Acting Muscarinic Antagonists and Associated Methods and Systems," Response to Office Action, dated May 7, 2012, filed Aug. 7, 2012, for co-pending U.S. Appl. No. 12/790,448, 19 pages.
Vehring et al., "Compositions for Pulimonary Delivery of Long-Acting Muscarinic Antagonists and Associated Methods and Systems," Response to Office Action, dated Oct. 16, 2012, filed Jan. 16, 2013, for co-pending U.S. Appl. No. 12/790,448, 17 pages.
Vehring et al., "Compositions for Pulimonary Delivery of Long-Acting Muscarinic Antagonists and Associated Methods and Sys-

(56) References Cited

OTHER PUBLICATIONS tems," Response to Office Action, dated Oct. 16, 2012, filed Mar. 1, 2012, for co-pending U.S. Appl. No. 12/790,448, 20 pages.

Vehring et al., "Compositions for Pulimonary Delivery of Long-Acting Muscarinic Antagonists and Associated Methods and Systems," Preliminary Amendment, filed Apr. 24, 2012, for co-pending U.S. Appl. No. 12/790,448, 8 pages.

Vehring et al., "Compositions for Pulmonary Delivery of Long-Acting B2 Adrenergic Receptor Agonists and Associated Methods and Systems," Office Action, dated Aug. 16, 2012, for corresponding U.S. Appl. No. 12/790,605, 14 pages.

Vehring et al., "Compositions for Pulmonary Delivery of Long-Acting B2 Adrenergic Receptor Agonists and Associated Methods and Systems," Office Action, dated Mar. 1, 2012, for corresponding U.S. Appl. No. 12/790,605, 11 pages.

Vehring et al., "Compositions for Pulmonary Delivery of Long-Acting B2 Adrenergic Receptor Agonists and Associated Methods and Systems," Response to Office Action, dated Aug. 16, 2012, filed Jan. 16, 2013, for corresponding U.S. Appl. No. 12/790,605, 26 pages.

Vehring et al., "Compositions for Pulmonary Delivery of Long-Acting B2 Adrenergic Receptor Agonists and Associated Methods and Systems," Response to Office Action, dated Mar. 1, 2012, filed Jun. 1, 2012, for corresponding U.S. Appl. No. 12/790,605, 23 pages.

Vehring et al., "Compositions for Pulmonary Delivery of Long-Acting B2 Adrenergic Receptor Agonists and Associated Methods and Systems," Response to Office Action, dated Sep. 6, 2013, filed Dec. 6, 2013, for corresponding U.S. Appl. No. 12/790,605, 24 pages.

Vehring et al., "Compositions for Pulmonary Delivery of Long-Acting B2 Adrenergic Receptor Agonists and Associated Methods and Systems," Office Action, dated Sep. 6, 2013, for corresponding U.S. Appl. No. 12/790,605, 18 pages.

Vehring et al., "Compositions for Pulmonary Delivery of Long-Acting B2 Adrenergic Receptor Agonists and Associated Methods and Systems," Notice of Allowance, dated Apr. 9, 2014, for U.S. Appl. No. 12/790,605, 11 pages.

Vehring et al., "Compositions for Pulmonary Delivery of Long-Acting B2 Adrenergic Receptor Agonists and Associated Methods and Systems," U.S. Appl. No. 14/327,425, filed Jul. 9, 2014, 119 pages.

Vehring et al., "Compositions for Pulmonary Delivery of Long-Acting Muscarinic Antagonists and Associated Methods and Systems," Final Office Action, dated Nov. 24, 2014, for U.S. Appl. No. 12/790,448, 21 pages.

Vehring et al., "Compositions for Pulmonary Delivery of Long-Acting B2 Adrenergic Receptor Agonists and Associated Methods and Systems," Office Action, dated May 1, 2015, for U.S. Appl. No. 14/327,425, 15 pages.

Vehring et al., "Compositions for Respiratory Delivery of Active Agents and Associated Methods and Systems," Advisory Action, dated Jun. 27, 2012, for U.S. Appl. No. 12/790,671, 3 pages.

Vehring et al., "Compositions for Respiratory Delivery of Active Agents and Associated Methods and Systems," Office Action, dated Nov. 14, 2011, for corresponding U.S. Appl. No. 12/790,671, 15 pages.

Vehring et al., "Compositions for Respiratory Delivery of Active Agents and Associated Methods and Systems," Office Action, dated Apr. 11, 2012, for U.S. Appl. No. 12/790,671, 18 pages.

Vehring et al., "Compositions for Respiratory Delivery of Active Agents and Associated Methods and Systems," Response to Office Action, dated Apr. 11, 2012, filed Sep. 11, 2012, for U.S. Appl. No. 12/790,671, 29 pages.

Vehring et al., "Compositions for Respiratory Delivery of Active Agents and Associated Methods and Systems," Response to Office Action, dated Feb. 19, 2014, filed Jul. 21, 2014, for corresponding U.S. Appl. No. 12/790,671, 33 pages.

Vehring et al., "Compositions for Respiratory Delivery of Active Agents and Associated Methods and Systems," Office Action, dated Apr. 10, 2015, for U.S. Appl. No. 12/790,671, 16 pages.

Vehring et al., "Compositions, Methods & Systems for Respiratory Delivery of Two or More Active Agents," Final Office Action, dated Mar. 13, 2015, for U.S. Appl. No. 12/790,710, 23 pages.

Vehring et al., "Compositions, Methods & Systems for Respiratory Delivery of Two or More Active Agents," Office Action, dated Dec. 17, 2014, for U.S. Appl. No. 14/334,503, 14 pages.

Vehring et al., "Compositions, Methods and Systems for Respiratory Delivery of Two or More Active Agents," U.S. Appl. No. 14/334,503, filed Jul. 17, 2014, 129 pages.

Vehring et al., "Compositions, Methods and Systems for Respiratory Delivery of Two or More Active Agents," Response to Office Action, dated Feb. 17, 2012, filed May 16, 2012, for U.S. Appl. No. 13/281,726, 20 pages.

Vehring et al., "Compositions, Methods and Systems for Respiratory Delivery of Two or More Active Agents," Response to Office Action, dated Mar. 28, 2013, filed Sep. 27, 2013, for co-pending U.S. Appl. No. 13/692,904, 21 pages.

Vehring et al., "Compositions, Methods and Systems for Respiratory Delivery of Two or More Active Agents," Amendment, filed on Jan. 31, 2014, for U.S. Appl. No. 13/109,884, 22 pages.

Vehring et al., "Compositions, Methods and Systems for Respiratory Delivery of Two or More Active Agents," Preliminary Amendment, filed Oct. 14, 2011, for U.S. Appl. No. 13/109,884, 16 pages.

Vehring et al., "Compositions, Methods and Systems for Respiratory Delivery of Two or More Active Agents," Preliminary Amendment, filed Dec. 3, 2012, for U.S. Appl. No. 13/692,904, 13 pages.

Vehring et al., "Compositions, Methods and Systems for Respiratory Delivery of Glycopyrrolate and Two or More Active Agents," Notice of Allowance, dated Oct. 28, 2013, for U.S. Appl. No. 13/692,904, 13 pages.

Vehring et al., "Compositions, Methods and Systems for Respiratory Delivery of Glycopyrrolate and Two or More Active Agents," Office Action, dated Mar. 28, 2013, for co-pending U.S. Appl. No. 13/692,904, 12 pages.

Vehring et al., "Compositions, Methods and Systems for Respiratory Delivery of Two or More Active Agents," U.S. Appl. No. 14/257,828, filed Apr. 21, 2014, 132 pages.

Vehring et al., "Compositions, Methods and Systems for Respiratory Delivery of Two or More Active Agents," Office Action, dated Nov. 20, 2013, for U.S. Appl. No. 12/790,710, 19 pages.

Vehring et al., "Compositions, Methods and Systems for Respiratory Delivery of Two or More Active Agents," Office Action, dated Oct. 31, 2013, for U.S. Appl. No. 13/109,884, 16 pages.

Vehring et al., "Compositions, Methods and Systems for Respiratory Delivery of Two or More Active Agents," Notice of Allowance, dated Aug. 2, 2012, for U.S. Appl. No. 13/281,726, 5 pages.

Vehring et al., "Compositions, Methods and Systems for Respiratory Delivery of Two or More Active Agents," Amendment After Allowance, filed Sep. 21, 2012, for U.S. Appl. No. 13/281,726, 11 pages.

Vehring et al., "Compositions, Methods and Systems for Respiratory Delivery of Two or More Active Agents," Office Action, dated Feb. 17, 2012, for U.S. Appl. No. 13/281,726, 27 pages.

Vehring et al., "Compositions, Methods and Systems for Respiratory Delivery of Two or More Active Agents," Supplemental Amendment, filed Oct. 3, 2013, for co-pending U.S. Appl. No. 13/692,904, 14 pages.

Vehring et al., "Compositions, Methods and Systems for Respiratory Delivery of Two or More Active Agents," Amendment After Allowance, filed Dec. 23, 2013, for co-pending U.S. Appl. No. 13/692,904, 18 pages.

Vehring et al., "Compositions, Methods and Systems for Respiratory Delivery of Two or More Active Agents," Preliminary Amendment, filed Dec. 3, 2013, for co-pending U.S. Appl. No. 13/692,904, 13 pages.

Vervaet et al., "Drug-surfactant-propellant interactions in HFA-formulations," *International Journal of Pharmaceutics* 186:13-30, 1999.

Vippagunta et al., "Crystalline solids," *Advanced Drug Delivery Reviews* 48:3-26, 2001.

(56) References Cited

OTHER PUBLICATIONS

Walker et al., "Prolonged effect of inhaled glycopyrrolate in asthma," *Chest* 91(1):49-51, 1987.
Wermuth (Ed.), "The Practice of Medicinal Chemistry: Chapter 37, Preparation of Water-Soluble Compounds Through Salt Formulation," Academic Press, Third Edition, p. 758, 2008, 6 pages.
Wesseling et al., "A Comparison of the Effects of Anticholinergic and $\beta_2$-Agonist and Combination Therapy on Respiratory Impedance in COPD," *Chest* 101(1):166-173, 1992.
Written Opinion, dated Jun. 28, 2016, for corresponding Singapore Application No. 11201507286Q, 14 pages.
Young et al., "The influence of micronized particulates on the aerosolization properties of pressurized metered dose inhalers," *Aerosol Science* 40:324-331, 2009.
Zheng (ed.), "Formulation and Analytical Development for Low-Dose Oral Drug Products," John Wiley & Sons, Inc., Hoboken, New Jersey, Table 4.1, p. 65, 2009, 3 pages.

FIG. 3A     FIG. 3B

METHODS AND SYSTEMS FOR CONDITIONING OF PARTICULATE CRYSTALLINE MATERIALS

BACKGROUND

Technical Field

This disclosure relates generally to systems and methods for the preparation and stabilization of particulate materials. More specifically, this disclosure relates to systems and methods for conditioning particulate materials to improve the physicochemical stability of the materials as well as compositions incorporating such particles.

Description of the Related Art

Particulate crystalline materials, including micronized crystalline particulates, are useful in a variety of contexts. For example, certain industrially useful compounds are conveniently stored in bulk as dry, particulate powders. Additionally, certain compounds can be better utilized or incorporated into commercial products when provided as micronized crystalline particulates. This can be seen with pharmaceutically active compounds that exhibit improved formulation, delivery, or therapeutic attributes when provided in micronized crystalline form.

However, processes used to produce certain crystalline materials can result in material characteristics that introduce an undesired level of physiochemical instability. Techniques for micronization of crystalline material often utilize energy-intensive milling, grinding, shearing or particle-to-particle collisions to reduce particle size. An example of one such technique is air jet milling, which uses high velocity air or gas to cause particle-to-particle collisions and to generate micronized material, including particles ranging from about 0.5 to about 30 μm in diameter. The exertion of thermal or mechanical energy during energy-intensive micronization processes can cause the formation of non-crystalline, amorphous material that can lead to significant physicochemical instability of the resulting micronized particles. Such amorphous material may be present in the form of amorphous regions on otherwise crystalline particles or as substantially amorphous particles.

The presence of amorphous material within micronized crystalline material can result in a propensity for the particles to fuse, aggregate, and/or agglomerate. In certain cases, the instability appears particularly acute when the micronized material is exposed, even for very short periods of time, to an environment that includes a solvent capable of solubilizing or plasticizing the amorphous material. In such instances, exposure of the micronized material often leads to recrystallization of amorphous material contained therein or sorbed, vapor-driven conversion of amorphous phase to crystalline phase, which can be accompanied by fusing and agglomeration of the micronized particles. The fusing, aggregation and/or agglomeration of the micronized particles can cause significant changes in particle size and the overall particle size distribution of the micronized material, which is problematic for applications requiring the long-term physical stability of the micronized material.

In addition, processes used in the manufacture and purification of crystalline materials can leave undesired contaminants. For example, solvents, including various organic solvents, play an important role in the manufacture of pharmaceutically active compounds and excipients used in the production of drug products. Solvents are often used during the synthesis of pharmaceutically active compounds and drug product excipients to increase yields or aid in crystallization. In many manufacturing processes, the final purification step involves crystallization or re-crystallization of the desired compound, and the crystalline material formed in such processes can entrap solvent present in the solution from which the material is crystallized. Even after subjecting the material to a drying step, such as a freeze-drying or a high-temperature drying process, solvent entrapped in a crystalline material is often difficult to completely remove, and some amount of residual solvent can remain. The presence of residual solvent, even in small amount can have undesirable effects. Organic solvents, in particular, can present health and safety hazards and can influence product efficacy, safety and stability.

BRIEF DESCRIPTION OF THE SEVERAL VIEWS OF THE DRAWINGS

FIG. 3A is a drawing of one view of one embodiment of a dispersion head assembly as described in the present disclosure.

FIG. 3B is a drawing of another view of one embodiment of a dispersion head assembly as described in the present disclosure.

DETAILED DESCRIPTION

Figure 1:
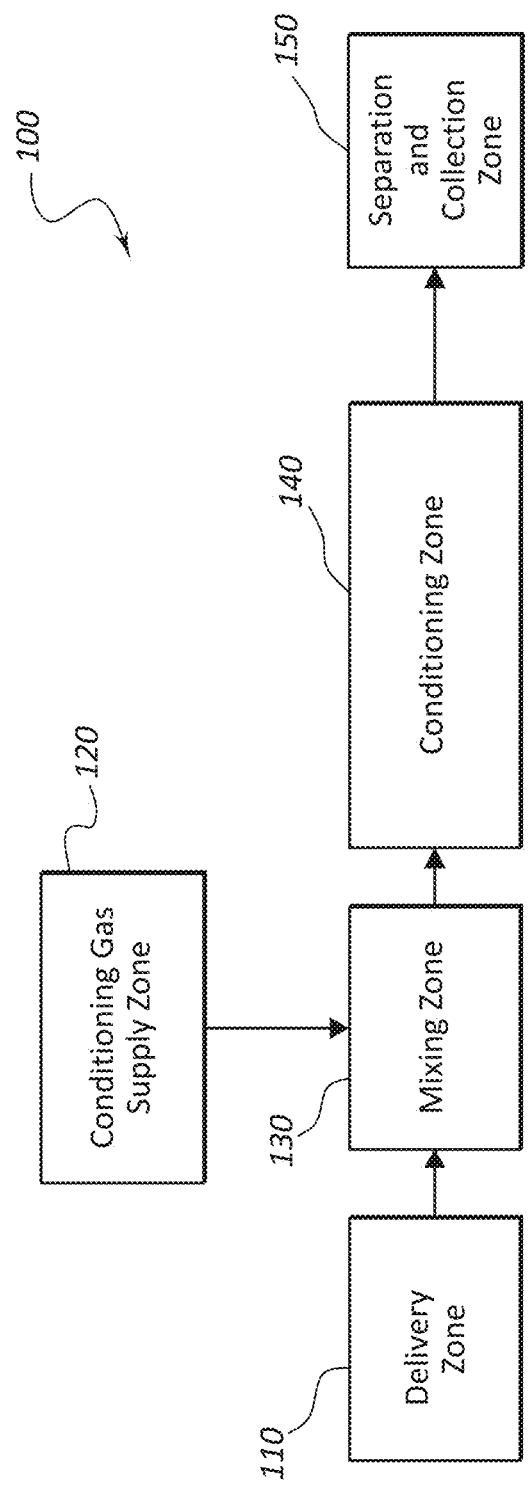
FIG. 1 is a diagram showing one embodiment of a system disclosed herein for in-process conditioning of micronized crystalline material.

Systems and methods for conditioning particulate crystalline material are described herein. Conditioning a particulate crystalline material according to the present description generally involves (i) providing a particulate material to be conditioned, (ii) delivering the material to be conditioned to a mixing zone where it is combined with a conditioning gas, (iii) maintaining the material in contact with the conditioning gas within a conditioning zone for a desired residence time, (iv) separating the conditioned material from the conditioning gas, and (v) collecting the conditioned material. In carrying out a conditioning process according to the present description, the material to be conditioned is typically entrained or aerosolized within a delivery gas that is blended with the conditioning gas, and the particulate material remains entrained, suspended or aerosolized in the conditioning gas as it travels through the conditioning zone. The nature of the conditioning gas and the residence time of the particulate material within the conditioning zone are controlled to accomplish annealing or phase transformation of the material.

In certain embodiments, the systems and methods described herein may be adapted for conditioning a single crystalline material. In alternative embodiments, the systems and methods described herein may be adapted to simultaneously condition two or more crystalline materials. For example, where two or more materials are to be conditioned simultaneously, the materials may be introduced into a conditioning zone as a blended material or as individual materials delivered via independent material inputs.

Additionally, the systems and methods described herein can be configured and adapted to provide one or more conditioning steps. For example, in certain embodiments, systems and methods may be adapted to provide a conditioning gas and conditioning zone that subject the particulate material to annealing conditions whereby amorphous material is converted into a more stable crystalline structure, and the amorphous content of the of the crystalline material is measurably reduced or eliminated. In other embodiments, the systems and methods described herein may be adapted to anneal particulate crystalline material by reducing the presence of residual solvent(s). In such embodiments, the systems and methods may be adapted to provide a conditioning gas and conditioning zone that subject the particulate material to annealing conditions whereby residual solvent within the crystalline material is reduced, removed, or replaced by, for example, vaporization or by solvent exchange. In still other embodiments, the methods and systems described herein can be adapted to both reduce or eliminate amorphous content and reduce or eliminate the presence of residual solvent(s). In such embodiments, the different annealing processes may be conducted simultaneously (e.g., using a conditioning gas and conditioning zone that serves to reduce both amorphous content and the presence of one or more solvent within the crystalline material) or sequentially using primary and secondary conditioning environments.

Where the systems and methods described herein are adapted to reduce amorphous content, without being bound by a particular theory, it is presently believed that amorphous material present in the crystalline particulate material undergoes an amorphous to crystalline phase transformation preceded by the plasticization or localized dissolution followed by crystallization of the amorphous material. Annealing of particulate material, including micronized material, as described herein works to reduce the amount of amorphous material and preserve the desired particle size distribution of the particulate material by inhibiting fusing, aggregation, and/or agglomeration of the micronized particles as a result of the plasticization or localized dissolution that can occur in unannealed materials. In specific embodiments, the methods described herein provide a reduction in amorphous content relative to unconditioned material of at least 50%. For example, in such embodiments, the methods described herein provide a reduction in amorphous content relative to unconditioned material selected from of at least 75% and at least 90%.

The systems and methods described herein are suited to conditioning a wide variety of particulate crystalline materials that include, for example, amorphous material (e.g., particles formed of amorphous material or crystalline particles that include one or more regions of amorphous material) and/or residual solvent. For example, the systems and methods described herein are suitable for application to materials exhibiting different physical and chemical characteristics (e.g., water soluble materials and materials soluble in organic solvents), and the methods and systems described herein are applicable to materials prepared for and useful in a wide range of products and processes, including, for example, industrial chemicals and processes, food products and additives, cosmetic products, nutritional products and formulations, such as nutritional supplement products, nutraceutical products and formulations, pharmaceutically active agents, and pharmaceutical excipients. In the context of food additives and nutritional products, for example, among many others, the systems and methods described herein may be utilized to improve the physiochemical stability of one or more of the following: aspartame; cyclamate; saccharin; stevia; sucralose; amino acids; vitamins; minerals for nutritional supplements; creatine; and ascorbic acid.

Though not limited to such applications, for convenience of description and exemplification, the disclosure and experimental examples provided herein describe the present systems and methods in the context of micronized crystalline materials for use in pharmaceutical products. Micronization of crystalline active agent and pharmaceutical excipient material is often employed and can be useful in formulation of pharmaceutical compositions for a variety of reasons. For example, for a given active agent or excipient, a crystalline morphology is the most physically and chemically stable morphology, yet it is often beneficial to reduce the particle size distribution of crystalline materials to facilitate delivery (e.g., micronization to allow respiratory or pulmonary delivery or to provide improved formulation characteristics, delivery performance, dissolution performance, and/or bioavailability). Where micronized material is utilized, however, preserving the physiochemical stability of micronized particulates is also generally important to maintaining the efficacy and shelf-life of pharmaceutical products incorporating such materials. Though they are described in the context of micronized pharmaceutical materials, the systems and methods according to the present description can be utilized to condition a variety of crystalline materials exhibiting any particle size distribution that allows the material to be entrained, suspended, or aerosolized within a conditioning gas contained within a conditioning zone for a residence time sufficient to anneal the selected material.

Active agents that can be delivered or formulated as a crystalline material can be processed using the systems and methods described herein. Systems and methods according to the present description are adaptable to water soluble active agents as well as to active agents soluble in organic solvents. Examples of active agents that may be processed according to the present methods include, but are not limited to, beta agonists, muscarinic antagonists, corticosteroids, PDE4 inhibitors, anti-infectives, diuretics, beta blockers, statins, anti-inflammatories, including non-steroidal anti-inflammatory actives, analgesics, and active agents exhibiting a combination of one or more of the preceding pharmacological effects (e.g., bi- or multifunctional molecules, such as, for example, a bi-functional muscarinic antagonist and beta agonist).

More specific examples of active agents suitable for processing using the systems and methods described herein include steroids, muscarinic antagonists, β-agonists, and bi-functional compounds exhibiting, for example, muscarinic antagonist and β-agonists activity suited for respiratory or pulmonary delivery. Such actives include, for example, short-acting beta agonists, e.g., bitolterol, carbuterol, fenoterol, hexoprenaline, isoprenaline (isoproterenol), levosalbutamol, orciprenaline (metaproterenol), pirbuterol, procaterol, rimiterol, salbutamol (albuterol), terbutaline, tulobuterol, reproterol, ipratropium and epinephrine; long-acting $β_2$ adrenergic receptor agonist, e.g., bambuterol, clenbuterol, formoterol, and salmeterol; ultra-long-acting $β_2$ adrenergic receptor agonists, e.g., carmoterol, milveterol, indacaterol, and saligenin- or indole-containing and adamantyl-derived $β_2$ agonists; corticosteroids, e.g., beclomethasone, budesonide, ciclesonide, flunisolide, fluticasone, methyl-prednisolone, mometasone, prednisone and trimacinolone; anti-inflammatories, e.g., fluticasone propionate, beclomethasone dipropionate, flunisolide, budesonide, tripedane, cortisone, prednisone, prednisilone, dexamethasone, betamethasone, or triamcinolone acetonide; antitussives, e.g., noscapine; bronchodilators, e.g., ephedrine, adrenaline, fenoterol, formoterol, isoprenaline, metaproterenol, salbutamol, albuterol, salmeterol, terbutaline; and muscarinic antagonists, including long-acting muscarinic antagonists, e.g., glycopyrronium, dexipirronium, scopolamine, tropicamide, pirenzepine, dimenhydrinate, tiotropium, darotropium, aclidinium, trospium, ipatropium, atropine, benzatropin, or oxitropium.

Where appropriate, the active agents conditioned using the systems and methods described herein may be provided as salts (e.g., alkali metal or amine salts or as acid addition salts), esters, solvates (hydrates), derivatives, or a free base. Additionally, the active agents may be in any isomeric form or mixture of isomeric forms, for example, as pure enantiomers, a mixture of enantiomers, as racemates or as mixtures thereof. In this regard, the form of the active agent may be selected to optimize the activity and/or stability.

The systems and methods described herein are also applicable to excipients, adjuvants, carriers, etc. used in pharmaceutical formulations. Such materials can be processed according to the methods described herein either individually or in mixtures suitable for formulation. Though not limited to these specific examples, the systems and methods described herein can be utilized to improve the physiochemical stability of sucrose, a-lactose monohydrate, mannitol, citric acid, glucose, maltose, arabinose, xylose, ribose, fructose, mannose, galactose, sorbose, trehalose, sorbitol, xylitiol, maltodextrin, and isomaltol.

Where a micronized crystalline material is conditioned using the methods or systems described herein, the material can be prepared to exhibit a wide range of desired particle size distributions using any suitable micronization technique. In the context of the present description, the term "micronized" refers to materials exhibiting a median size as large as, for example, 500 microns, and "micronization" processes refer to any suitable process by which a micronized crystalline material is produced. The desired particle size or size distribution of crystalline material conditioned according to the present description will depend on, among other factors, the nature of the material and its desired use or application of the material. Techniques suitable for preparing and providing micronized crystalline material include, for example, milling or grinding processes, including wet-milling and jet milling processes, precipitation from supercritical or near-supercritical solvents, high pressure homogenization, spray drying, spray freeze drying, or lyophilization. Examples of patent references teaching suitable methods for obtaining micronized crystalline particles include, for example, in U.S. Pat. Nos. 6,063,138, 5,858, 410, 5,851,453, 5,833,891, 5,707,634, and International Patent Publication No. WO 2007/009164, the contents of each of which are incorporated herein by reference.

Though the median size of a micronized material may be as large as 500 μm, often where a micronized material is needed, the particle size distribution of the material will be significantly smaller. For example, in many contexts requiring micronized material, the material will exhibit a median particle size of 100 μm or less. In the context of pharmaceutically active agents or materials prepared for use in pharmaceutical formulations, the median particle size of the micronized material may be below 50 μm or even 10 μm. Where the micronized material conditioned according to the methods described herein is an excipient or active agent to be used in a pharmaceutical product for pulmonary delivery, the micronized material is prepared to exhibit a particle size distribution that facilitates pulmonary delivery. In such embodiments, for example, the micronized material may exhibit a particle size distribution wherein at least 90% of the active agent particles by volume exhibit an optical diameter of about 10 μm or less. In other such embodiments, the micronized material may exhibit a particle size distribution wherein at least 90% of the active agent particles by volume exhibit an optical diameter selected from a range of about 10 μm to about 1 μm, about 9 μm to about 1 μm, about 8 μm to about 1 μm, about 7 μm to about 1 μm, about 5 μm to about 2 μm, and about 3 μm to about 2 μm. In still further embodiments where the micronized material is prepared for use in a pharmaceutical product for pulmonary delivery, the micronized material may exhibit a particle size distribution wherein at least 90% of the active agent particles by volume exhibit an optical diameter selected from 10 μm or less, 9 μm or less, 8 µm or less, 7 µm or less, 6 µm or less, 5 µm or less, 4 µm or less, 3 µm or less, 2 µm or less, or 1 µm or less.

It will be readily understood that the embodiments, as generally described herein, are exemplary. The more detailed description of the systems and methods provided herein is not intended to limit the scope of the present disclosure, but is merely representative of various embodiments.

I. Definitions

Unless specifically defined otherwise, the terms used herein have their normal meaning as understood in the art. The following terms are specifically defined for the sake of clarity.

The term "active agent" as used herein includes any agent, drug, compound, composition or other substance that may be used on, or administered to a human or animal for any purpose, including any agent, drug, compound, composition or other substance that provides a nutritional, therapeutic, pharmaceutical, pharmacological, diagnostic, cosmetic, prophylactic agents and/or immunomodulating effect. The term "active agent" may be used interchangeably with the terms, "drug," "pharmaceutical," "medicament," "drug substance," "active pharmaceutical ingredient," "pharmaceutically active agent," or "therapeutic." As used herein the "active agent" may also encompass natural or homeopathic products that are not generally considered therapeutic.

The term "annealing" refers to a physiochemical change or phase transformation in a material that results in improved physiochemical stability. In certain embodiments, the term "annealing" refers to a process whereby amorphous content within a crystalline particulate material is reduced or eliminated. In other embodiments, the term "annealing" refers to a process whereby residual solvent contained within a crystalline particulate material is reduced or eliminated by, for example, solvent vaporization and/or exchange. In still further embodiments, the methods and systems described herein may anneal a crystalline particulate material by both reducing amorphous content and reducing the presence of a residual solvent.

The term "conditioning," as used herein, generally refers to methods and processes that may be used to improve the physiochemical stability of a particulate crystalline material. In specific embodiments, the term "conditioning" refers to methods that cause a controlled annealing of the particulate material.

The term "phase transformation" refers to a change in the bulk of the crystals present in a particulate crystalline material. In particular embodiments, annealing of a material using the conditioning systems or methods described herein results in a phase transformation selected from, for example, removal of a solvent of crystallization, replacement of a solvent of crystallization, an amorphous to crystalline phase change, or a change in physical structure beyond just an amorphous to crystalline phase change.

As used herein, "physiochemical" refers to one or both of the physical and chemical stability of a material.

As used herein, the term "inhibit" refers to a reduction, prevention, or slowing of any given process, event, or characteristic.

When used to refer to the conditioned particulate material described herein, the terms "physical stability" and "physically stable" refer to a composition that is resistant to one or more of particle fusing, aggregation, agglomeration, and particle size changes. In certain embodiments, physical stability may be evaluated through exposing the particulate material to accelerated degradation conditions, such as increased temperature and/or humidity as described herein.

When referred to herein, the term "optical diameter" indicates the size of a particle as measured using a laser diffraction particle size analyzer equipped with a dry powder dispenser (e.g., Sympatec GmbH, Clausthal-Zellerfeld, Germany).

II. Systems for Conditioning Particulate Crystalline Material

FIG. 1 provides a schematic illustration of an embodiment of a system for conditioning particulate crystalline material according to the present description. The system 100 includes a delivery zone 110, wherein one or more crystalline materials (e.g., one or more pharmaceutically active agents or pharmaceutically acceptable excipients or adjuvants) may be delivered and prepared for mixing with a conditioning gas. The system also includes a conditioning gas supply zone 120. The conditioning gas is supplied from the conditioning gas supply zone 120, and in certain embodiments, the conditioning gas is generated within the conditioning gas supply zone 120. The crystalline particulate material and the conditioning gas may be introduced into a mixing zone 130, after which they enter a conditioning zone 140. The conditioning zone 140 includes a controlled atmosphere contained and maintained within a conditioning chamber. The controlled atmosphere includes the conditioning gas and any delivery gas used for delivering the crystalline particulate material, and the particulate material being conditioned remains entrained, suspended, or aerosolized within the controlled atmosphere within the conditioning chamber. The crystalline material undergoes an annealing process within the conditioning zone 140 as it is maintained within the conditioning zone 140 for a desired residence time. The micronized material may be separated from the conditioning gas and collected from the conditioning zone 140 in the separation and collection zone 150, which can include any of a number of well-known components suited to the collection of micronized material.

The nature of and extent to which annealing of the particulate material takes place can be controlled by the residence time of the material within the conditioning zone and by the properties of the conditioning gas, including, for example the presence and concentration of one or more solvents, and the temperature, flow rate, and direction or turbulence of flow of the conditioning gas. In some embodiments of the systems disclosed herein, the residence time of the micronized active agent particles in the conditioning zone 140 may be controlled by the geometry of the conditioning zone 140 or by the flow rate of the conditioning gas through the conditioning zone 140.

The material to be conditioned may be provided to the delivery zone 110 in a form that is appropriate for the chosen material and the conditioning process. Where a particulate material exhibiting a desired particle size distribution is desired, the material may be prepared to exhibit the targeted particle size distribution prior to introduction into the delivery zone 110. In such an embodiment, the particulate material can be fed from the delivery zone 110 into the mixing zone 130 using any suitable device or system for controlled feeding of a powder or particulate material at a desired feed rate. Controlled feeding of the particulate material will typically include entraining the particulate material in a dispersion component, such as, for example a delivery gas suitable for dispersion and delivery of the particulate material into the mixing zone 130 and/or the conditioning zone 140.

In certain embodiments, particulate material may be subjected to a micronization process within the delivery zone 110. In such embodiments, the delivery zone 110 may include a device or system that processes the crystalline material to provide a micronized particulate material that exhibits a desired particle size distribution. Where the delivery zone 110 includes a device or system suitable for carrying out micronization of the selected crystalline material, the delivery zone 110 may incorporate any one of a number of known devices or systems for micronization. For example, the crystalline material may be micronized in the delivery zone 110 using known milling or grinding processes, known crystallization or recrystallization processes, or known micronization processes utilizing precipitation from supercritical or near-supercritical solvents, spray drying, spray freeze drying, or lyophilization.

In embodiments where the delivery zone 110 includes a micronizer, the mixing zone 130 and/or conditioning zone 140 may be operably linked to the micronizer. In such embodiments, the crystalline material may be processed to exhibit the targeted particle size distribution within the delivery zone 110 and, prior to collection, immediately delivered to the mixing zone 130 while the particles remain airborne as they exit from the micronizer. Therefore, the systems and methods described herein allow for conditioning of micronized material as a sequential but integrated step in a process of producing and collecting a micronized crystalline material. Such "in-line" or "in-process" conditioning of micronized crystalline material provides the benefits associated with the annealing achieved by the conditioning process, while also eliminating the need to conduct a first process for producing micronized (or size comminuted) material followed by a second, separate conditioning process for annealing the micronized material.

The mixing zone 130 illustrated in FIG. 1 is shown as separate from the conditioning zone 140. In such an embodiment, the crystalline material to be conditioned (such as, e.g., micronized material suspended or entrained within a delivery gas) and the conditioning gas are delivered to the mixing zone 130 prior to their entry into the conditioning zone 140. The mixing zone 130 can be sized and configured as desired to achieve desired mixing of the particulate material and conditioning gas. In certain embodiments, the mixing zone 130 may include a dispersion head assembly into which both the particulate material and the conditioning gas are fed and directed into the conditioning zone 140. Alternatively, in other embodiments, the mixing zone 130 may be an area within the conditioning zone 140 where the particulate material and the conditioning gas are delivered into the conditioning zone in a manner that accomplishes the mixing required for annealing of the particulate material within the conditioning zone. In such embodiments, the micronized material may be introduced into the conditioning zone as a particulate material entrained or aerosolized within a delivery gas, and the conditioning gas may be introduced into the conditioning chamber such that the conditioning gas begins to mix with the delivery gas and the micronized material disbursed therein upon entry into the conditioning zone 140.

The conditioning zone 140 may be formed within a conditioning chamber, which can be provided by any structure, such as a column, tank, tube, funnel, coil, or the like, suitable for maintaining a controlled atmosphere and receiving the particulate material and conditioning gas. The characteristics of the controlled atmosphere within the conditioning zone 140 can be adjusted to achieve a desired conditioning of one or more selected particulate materials. In particular embodiments, the conditioning gas is delivered at a specified rate and mixes with the delivery gas at a selected ratio. For example, the conditioning gas may be supplied to the conditioning zone 140 (e.g., through a dispersion head assembly) at a targeted gas flow rate. The gas flow rate will depend on, among other factors, the amount of micronized material being processed and the angle at which the gas is introduced into the conditioning zone 140. In certain embodiments, the conditioning gas is introduced into the conditioning zone 140 at a rate ranging from about 20 SCFM up to about 500 SCFM, and the delivery gas having the particulate material to be conditioned entrained therein may be supplied at a gas flow rate ranging from about 20 SCFM up to about 75 SCFM. However, depending on the angle at which the conditioning and delivery gases are introduced into the conditioning zone 140 and the nature of the material being processed, the gas flow rate of both the conditioning gas and the delivery gas may be increased as high as 3,300 SCFM. In other embodiments, the conditioning gas may be supplied at a flow rate of 30 SCFM up to about 100 SCFM and the delivery gas containing the micronized material to be conditioned may be supplied at a gas flow rate ranging from about 30 SCFM up to about 60 SCFM. In addition to, or as an alternative to, controlling the rate at which the conditioning gas is introduced into the controlled atmosphere, the ratio of the conditioning gas to the delivery gas may be selected to facilitate conditioning of the micronized material. In particular embodiments, the conditioning gas is mixed with the delivery gas at a ratio selected from 1:1, 1.2:1, 1.4:1, 1.6:1, 1.8:1, 2.0:1, 2.2:1, 2.4:1, 2.6:1, 2.8:1, 3:1, 3.2:1, 3.4:1, 3.6:1, 3.8:1, and 4:1.

The temperature of the conditioning gas may also be controlled. Annealing of particulate material can be significantly affected by temperature. In certain embodiments, the temperature of the conditioning gas is selected from between about 10° C. and 100° C. In specific examples of such embodiments, the temperature of the conditioning gas may be selected from one of the following ranges, between about 10° C. and 70° C., between about 20° C. and 50° C., between about 10° C. and 50° C., and between about 20° C. and 30° C., depending on the nature of the particulate material being processed.

The conditioning gas may also include one or more solvent vapors. In such embodiments, the conditioning gas includes a carrier gas having one or more solvent vapors dispersed therein. The inclusion of a solvent vapor within the conditioning gas can be particularly useful in conditioning processes adapted to reduce or eliminate amorphous content and to conditioning process adapted to reduce or eliminate the presence of residual solvent(s) by solvent exchange.

Where a solvent is included in the conditioning gas, the solvent will typically be selected according to the material to be conditioned. For example, in embodiments where the material to be conditioned is water soluble, the conditioning gas may include water vapor carried within an inert gas. In certain embodiments, the solvent vapor may be a combination of water and water miscible organic solvents (e.g., alcohols, ketones, esters, etc.) Alternatively, in embodiments where the material to be conditioned is not water soluble, but exhibits solubility in one or more organic solvents, the solvent vapor included in the conditioning gas may simply include an organic solvent vapor, such as an alcohol (e.g., ethanol, methanol, isopropyl alcohol, etc.), ketone (e.g., acetone, methyl ketone, ethyl ketone, etc.), ester (e.g., ethyl acetate, etc.), aliphatic alcohol (e.g., octanol, etc.), or alkane (e.g., octane, nonane, etc.) vapor, carried within an inert gas. As used herein, "inert" refers to a carrier gas that is non-reactive with the micronized material being conditioned and preferably the solvent vapor. Examples of inert gases include, without limitation, compressed dry air, nitrogen, inert gas (e.g., argon, helium, etc.), carbon dioxide, and the carrier gas included in the conditioning gas can be selected according to the solvent vapor or combination of solvent vapors to be used in the conditioning gas or conditioning zone. In embodiments where the conditioning of the particulate material includes solvent exchange, the solvent(s) included in the conditioning gas may be selected to provide improved safety and/or physiochemical stability of the particulate material.

Where a solvent is included in the conditioning gas, the conditioning gas can be prepared and maintained at a specified temperature or temperature range in order to maintain the solvent as a vapor. As already mentioned, controlling the temperature of the conditioning gas can also serve to facilitate the conditioning process, with the temperature being selected to facilitate a desired level of annealing over a selected residence time.

The relative concentration of solvent vapor included in a conditioning gas can also be adjusted to accomplish a desired level of conditioning for different material characteristics. For example, the concentration of solvent vapor within the conditioning gas may be adjusted based on the chemical or physical properties of the crystalline material to be processed. In specific embodiments, the relative humidity (RH) or relative saturation (RS) and temperature conditions of the conditioning gas are selected to provide RH or RS and temperature conditions that exceed the glass transition temperature (Tg) of the amorphous content of the material being processed. For example, for each of the solvents included within the conditioning gas, the vapor pressure of the solvent may be maintained at a vapor pressure of about 0.05 to 0.95 of the saturation vapor pressure for the solvent.

Figure 16:
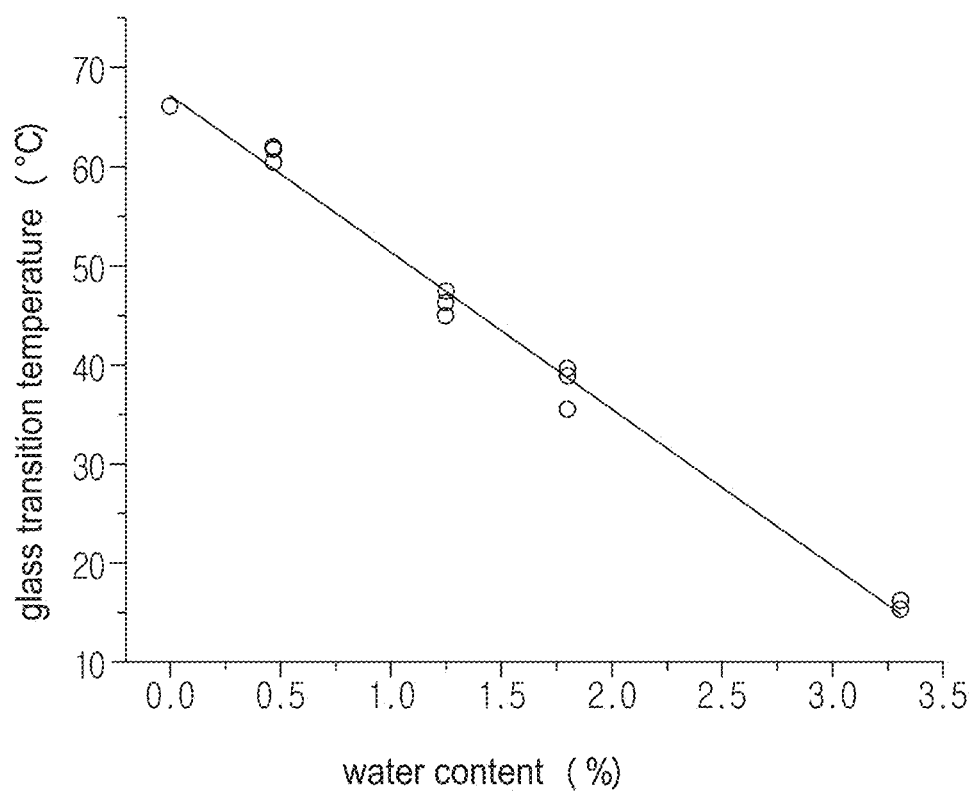
FIG. 16 illustrates an exemplary plasticization curve, which shows the Tg of a given amorphous material as a function of solvent content.

Crystallization of an amorphous phase typically occurs rapidly when the amorphous material is exposed to conditions that exceed its glass transition temperature, usually twenty degrees Celsius above the glass transition temperature (Lechuga-Ballesteros, D.; Miller, D. P.; Zhang, J., Residual water in amorphous solids, measurement and effects on stability. In *Progress in Amorphous Food and Pharmaceutical Systems*, Levine, H., Ed. The Royal Society of Chemistry: London, 2002; pp 275-316). Exposure of amorphous material to temperature in excess of the glass transition can be achieved in the absence of any solvent by exposing the amorphous material to a stream of hot air above its glass transition temperature. However, the glass transition temperature is also a function of the fraction of solvent present in the amorphous material, an effect known as plasticization. Plasticization is typically represented by a plasticization curve, such as the one shown in FIG. 16, which shows the Tg of a given amorphous material as a function of solvent (in this case water) content.

Figure 17:
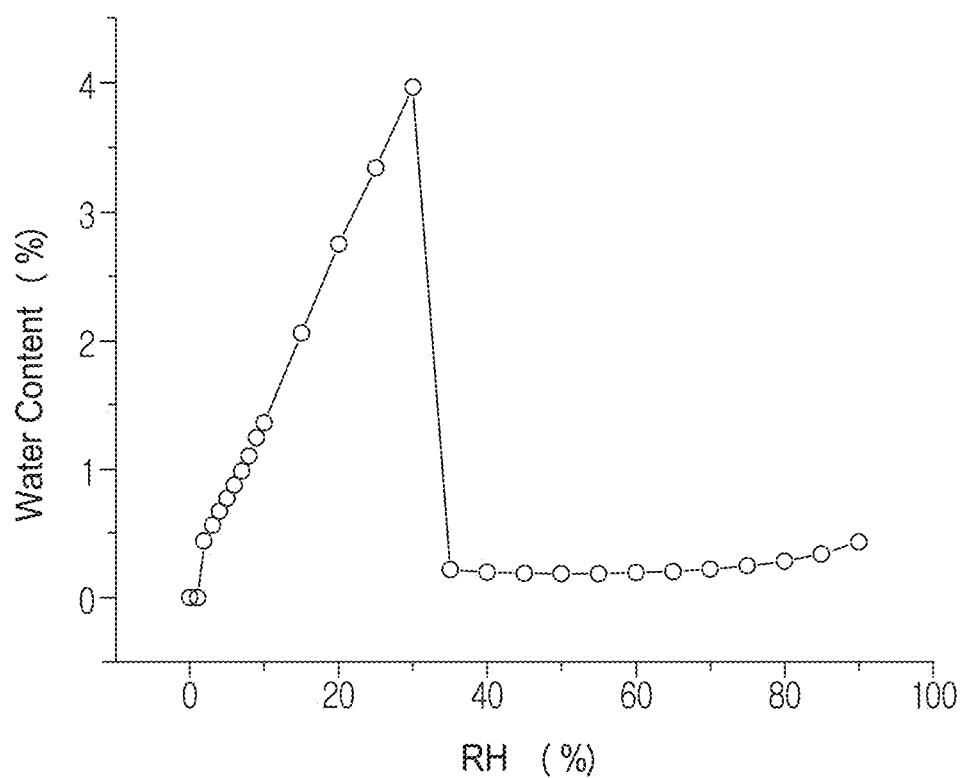
FIG. 17 illustrates an exemplary sorption isotherm, representing the amount of solvent in an amorphous material as a function of the solvent activity at a given temperature.

In addition, the solvent content held in an amorphous material is a function of the vapor concentration of the solvent surrounding the amorphous solid. This can be illustrated by the sorption isotherm provided in FIG. 17. The sorption isotherm of a given material is a representation of the amount of solvent in the amorphous material as a function of the solvent activity (which is proportional to the solvent vapor pressure to saturation solvent vapor pressure ratio) at a given temperature.

Figure 18:
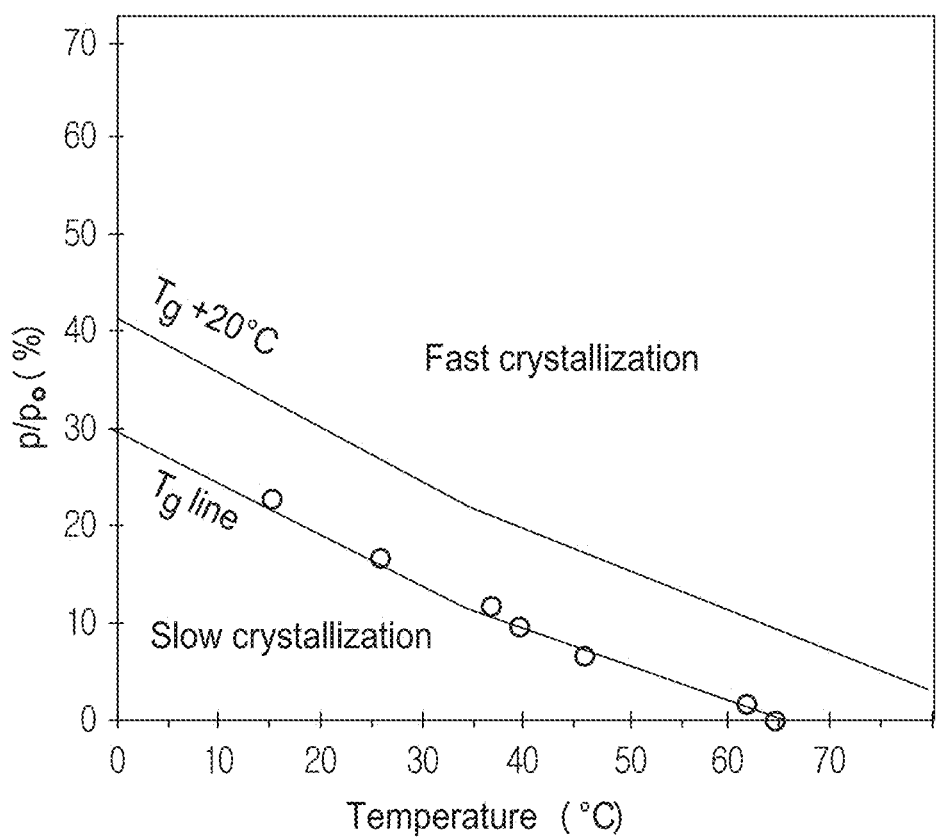
FIG. 18 illustrates an exemplary stability diagram for glycopyrrolate.

The glass transition plasticization curve and the sorption isotherm can be combined to construct a stability diagram as the one shown in FIG. 18 for the selected material. The stability diagram shown in FIG. 18 is one created for glycopyrrolate. The stability diagram can be used to choose operational conditions for the systems and methods described herein that promote fast annealing of the crystalline material selected for conditioning. For example, as is illustrated in FIG. 18, in the case of glycopyrrolate fast crystallization of amorphous material will occur at RH>50% in the range of 20-40° C., and at 60° C. it would only require 10% RH to promote annealing.

The nature and extent of annealing that takes place within the conditioning zone can also be adjusted by altering the residence time of the particulate material within the conditioning zone 140. The residence time is the average time particulate material spends within the conditioning zone 140. The residence time of the particulate material within the conditioning zone 140 can be adjusted by changes to one or more of a variety of process variables. For example, the volume and dimensions of the conditioning chamber can be altered, to provide longer or shorter residence times, with, for example, relatively higher volume or larger physical dimensions generally resulting in relatively longer residence times. The flow rates and temperatures of one or both of the conditioning gas and the delivery gas can also be adjusted to affect residence time. In addition, the manner by which the conditioning gas or delivery gas is introduced into the conditioning chamber can affect particle residence time. As an example, introduction of the conditioning gas and/or delivery gas in a manner that creates a generally linear flow through the conditioning chamber may create a relatively shorter residence time compared to introduction of the same gas(es) in a manner that creates a more turbulent recirculating dispersion of the gas(es).

In general, the residence time of the particulate material within the conditioning chamber can be selected from about 0.5 seconds to several minutes. In particular embodiments, the residence time may be up to about 10 minutes or 600 seconds. In particular embodiments, the residence time may be selected from about 0.5 to about 10 seconds, 0.5 to about 20 seconds, 0.5 to about 30 seconds, 0.5 to about 40 seconds, and 0.5 to about 50 seconds. In certain such embodiments, the particulate material may be conditioned by the conditioning gas for a residence time selected from about 0.5 seconds, 1 second, 1.5 seconds, 2 seconds, 2.5 seconds, 3 seconds, 3.5 seconds, 4 seconds, 5 seconds, 6 seconds, 7 seconds, 8 seconds, 9 seconds, and 10 seconds.

After the particulate material has been annealed in the conditioning zone 140, the conditioned material is separated from the conditioning gas and collected in the separation and collection zone 150. The micronized material may be separated and collected from the conditioning gas using known particle collection techniques and equipment. In certain embodiments of the systems disclosed herein, the micronized material may continue to anneal while in the separation and collection zone 150. The collection zone 150 can be formed by or include a cyclone collector. Cyclone collectors for collection of particulate materials, including micronized materials, and separation of such materials from a conditioning gas. Cyclone collectors are commercially available and suitable for use as the collection zone 150 of the systems described herein.

In addition to a collection device, such as a cyclone collector, the collection zone 150 may be configured to facilitate direct collection of the processed material. Where a collection zone 150 is configured to allow direct collection of the conditioned material, the collector included in the collection zone may simply deliver the conditioned product to a container from which the conditioned material can be collected or removed. Such a container may include a collection bag that can be removed from the collection device, as is often used in conjunction with a cyclone collector. The collection bag may be sealable and formed using a material that enables efficient collection of the conditioned material, while also being permeable to a gas used in the collection system. In another embodiment, the collector included in the collection zone 150 may be configured as a holding chamber. In such an embodiment, the collector, such as a cyclone collector, may be used to separate the conditioned material from a conditioning gas and collect the conditioned material into a holding chamber where the conditioned material can be maintained in a fluidized state for a desired period of time. Annealing of the crystalline material processed according to the present description is not always complete as the material exits the conditioning zone 140, and may continue as the material is collected. Depending on the material being processed and the annealing conditions, it may be beneficial to maintain the conditioned material in a fluidized state within a collection chamber for a period of time sufficient to allow additional progress of the annealing process.

Figure 19:
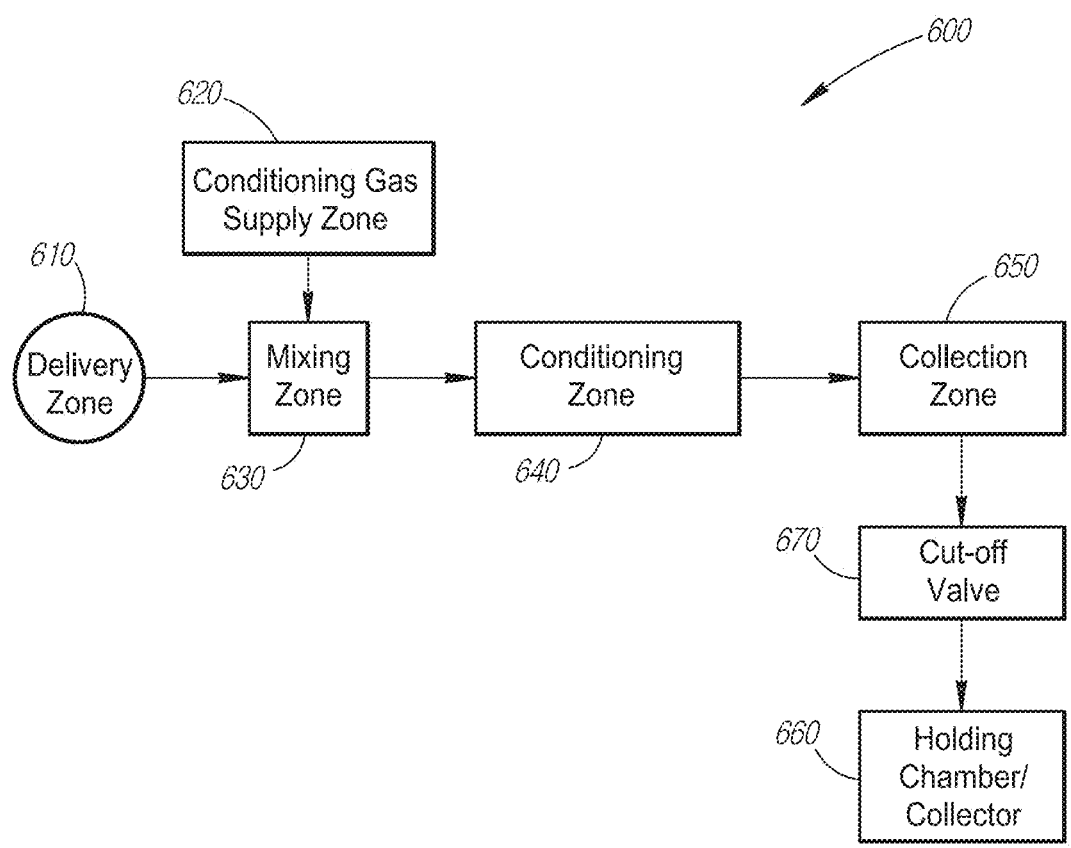
FIG. 19 is a diagram showing an embodiment of a system disclosed herein configured to facilitate multiple conditioning steps.

In still other embodiments, the collection zone 150 may be configured to allow further processing of the conditioned material. In such embodiments, the collection zone 150 may be operably linked to one or more additional systems, including an additional conditioning system as described herein, for further processing of the conditioned material. In such embodiments, the collector included in the collection zone 150 may be configured to deliver the conditioned material directly for continued processing or the collection zone 150 may be configured to include or be in operable communication with a holding chamber as described and illustrated herein, such as, for example, in association with the systems illustrated in FIG. 19 and FIG. 20.

In some embodiments, the systems and methods described herein may be utilized to simultaneously process and condition more than one particulate material. For example, two or more micronized materials may be simultaneously introduced into a conditioning zone. The materials may be combined prior to introduction into the conditioning zone or they may be introduced independently into the conditioning zone. In some embodiments, the materials may be combined prior to micronization and introduced into the conditioning zone as a particulate material including a combination of two or more chemical entities. Even further, where two or more different particulate materials are introduced into the conditioning zone (whether as a combined product stream or as two or more independently introduced materials), the materials may exhibit similar solubility characteristics (e.g., each of the different materials exhibit solubility in water or each of the materials exhibit solubility in a given organic solvent). However, the methods described herein are also suited to simultaneously conditioning two or more materials in the same conditioning zone where at least two of the two or more different materials exhibit different solubility characteristics (e.g., at least one is water soluble, while another is soluble only in an organic solvent, or one is soluble in a first organic solvent, while a second is soluble in a second organic solvent).

Figure 2:
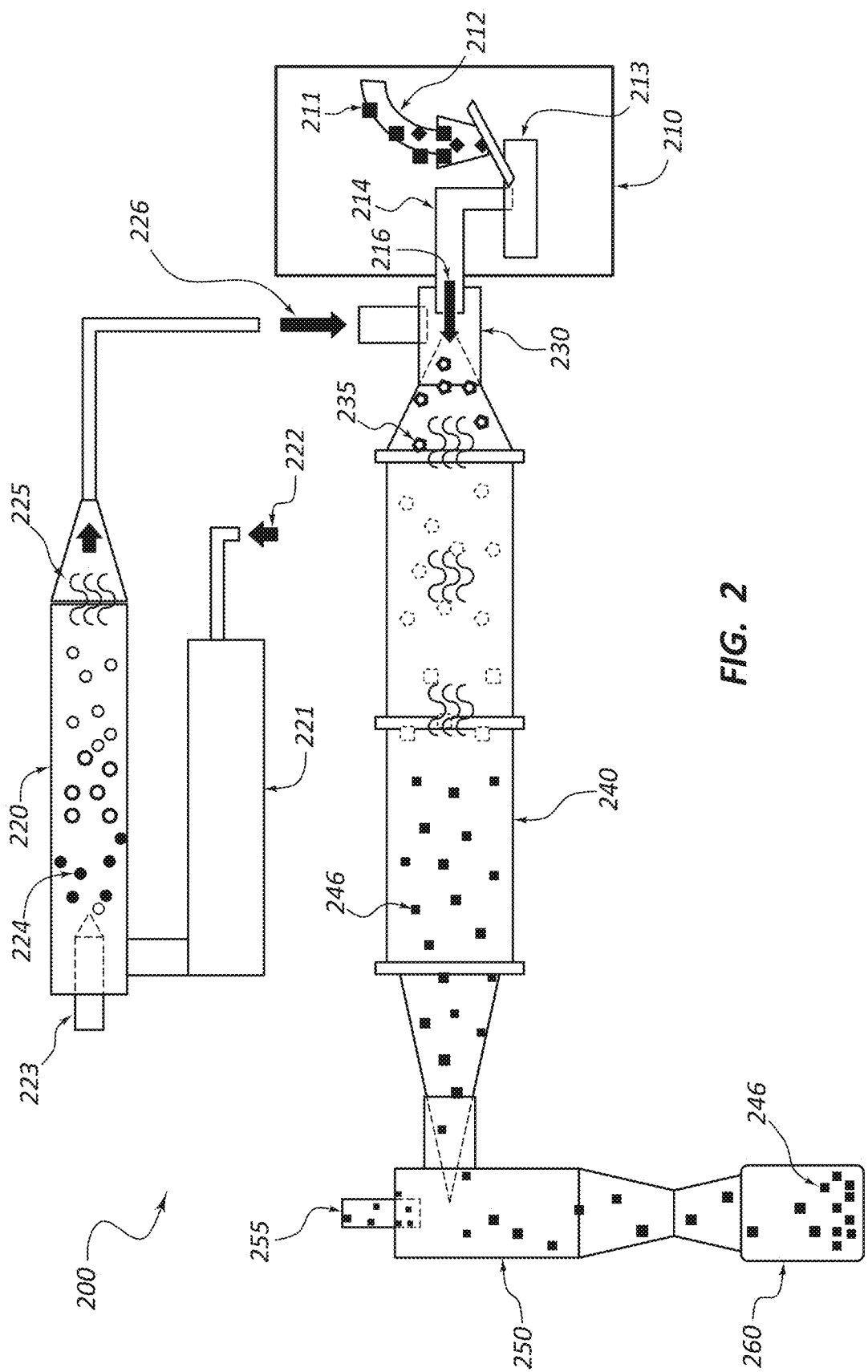
FIG. 2 is a diagram showing an embodiment of a system disclosed herein for in-process conditioning of micronized crystalline material.

Certain embodiments of a system for the in-process conditioning of a micronized material according to the present description can be represented by the system illustrated in FIG. 2. Because the delivery zone of the system illustrated in FIG. 2 includes a device configured for the micronization of the material to be conditioned, the delivery zone of the system will be referred to as a micronizing zone 210. As shown in FIG. 2, the micronizing zone 210 may be configured to deliver aerosolized micronized particles directly into a mixing zone 230. In specific embodiments, the micronization zone 210 includes a jet mill 213 and the crystalline material 211 to be micronized is delivered to the jet mill 213 using a standard feeder 212. After micronization, the micronized material 235 may be delivered through an outlet 214 as aerosolized particles carried by a delivery gas 216 and supplied to the mixing zone 230.

The micronized crystalline material is supplied to the mixing zone 230 as a micronized material with a desired particle size distribution. In certain embodiments, for example, at least 90% of the micronized particles by volume exhibit an optical diameter of about 10 µm or less. In other embodiments, at least 90% of the micronized crystalline particles by volume exhibit an optical diameter selected from a range of about 10 µm to about 1 µm, about 9 µm to about 1 µm, about 8 µm to about 1 µm, about 7 µm to about 1 µm, about 5 µm to about 2 µm, and about 3 µm to about 2 µm. In further embodiments, at least 90% of the micronized crystalline particles by volume exhibit an optical diameter selected from 10 µm or less, 9 µm or less, 8 µm or less, 7 µm or less, 6 µm or less, 5 µm or less, 4 µm or less, 3 µm or less, 2 µm or less, or 1 µm or less.

The micronizing zone 210 may be separated from an external environment or contained within a safety barrier or enclosure (not shown). Such a design can be particularly advantageous where the micronized material is an active agent or is otherwise biologically active. The safety barrier may be used in order to prevent unwanted contact with any micronized material produced in the micronizing zone 210. Where included in the systems described herein, a safety barrier may be constructed of any suitable material such as metal, glass, plastic, composites, etc., that are sufficient to contain micronized particles.

With reference to FIG. 2, in particular embodiments, the conditioning gas 226 utilized in an in-line conditioning system may be prepared within the conditioning gas supply zone 220. For example, the conditioning gas supply zone 220 may include a heating chamber 221 to which a carrier gas 222 may be provided for heating to a desired temperature. In one such embodiment, the heating chamber 221 comprises a heat source, such as an electric heater or furnace, for heating the carrier gas 222. The carrier gas 222 provided for use in the systems disclosed herein may comprise one or more gases suitable for the methods described herein for conditioning a given micronized crystalline material. For example, the carrier gas 222 may comprise one or more inert gasses or atmospheric gasses such as those described herein, including, for example, compressed air, nitrogen, oxygen, and helium.

The conditioning gas supply zone 220 may further comprise a liquid evaporation chamber 225. The solvent used to produce the solvent vapor disbursed within the carrier gas 222 can be generated within or provided from the evaporation chamber 225, and the evaporation chamber can be configured to provide the carrier gas 222 with a desired concentration of solvent vapor within the conditioning gas 226. Where the micronized crystalline material is water soluble, the solvent can be an aqueous solvent, such as purified or distilled water, and in such embodiments, the evaporation chamber 225 is configured to create a conditioning gas 226 having a desired relative humidity. In other embodiments, particularly where the micronized crystalline material to be conditioned is not water soluble, the solvent for use with the systems disclosed herein may be a non-aqueous liquid, such as an organic solvent described herein.

A liquid atomizer 223 may be used to deliver liquid solvent to the carrier gas 222 in the form of atomized liquid droplets 224 suspended within the carrier gas 222. Atomization of the liquid solvent facilitates conversion of the liquid solvent into a solvent vapor within the evaporation chamber 225. In more specific embodiments, a liquid atomizer used in the systems described herein provides control over the size of the atomized droplets delivered to the carrier gas 222 as well as the rate and volume of liquid solvent atomized. Where used, a liquid atomizer 223 can be selected from, for example, pressure nozzles, pneumatic atomizers, impinging jet atomizers. In one such embodiment, the carrier gas 222 is heated in the heating chamber 221, a liquid atomizer 223 delivers liquid solvent to the carrier gas within the conditioning gas supply zone 220, and the carrier gas 222 and atomized liquid solvent 224 are supplied to the liquid evaporation chamber 225. As the carrier gas 222 and atomized liquid solvent 224 pass through the liquid evaporation chamber, the liquid solvent vaporizes and the carrier gas becomes a conditioning gas 226 having a desired solvent vapor concentration.

In certain embodiments, where the solvent vapor is formed from an aqueous solvent, the conditioning gas 226 may be supplied at a temperature ranging from about 20° C. to about 100° C., and with a relative humidity ranging from about 0.05% to about 75%. In more specific embodiments where the solvent used to form the solvent vapor is an aqueous solvent, the conditioning gas 226 may be supplied having a temperature selected from at least about 20° C., 21° C., 22° C., 23° C., 24° C., 25° C., 26° C., 27° C., 28° C., 29° C., and 30° C. and having a relative humidity selected from at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74% and 75%. In particular embodiments, however, the temperature may be as high as 22° C. and the relative humidity as low as 0.05%.

Figure 3C:
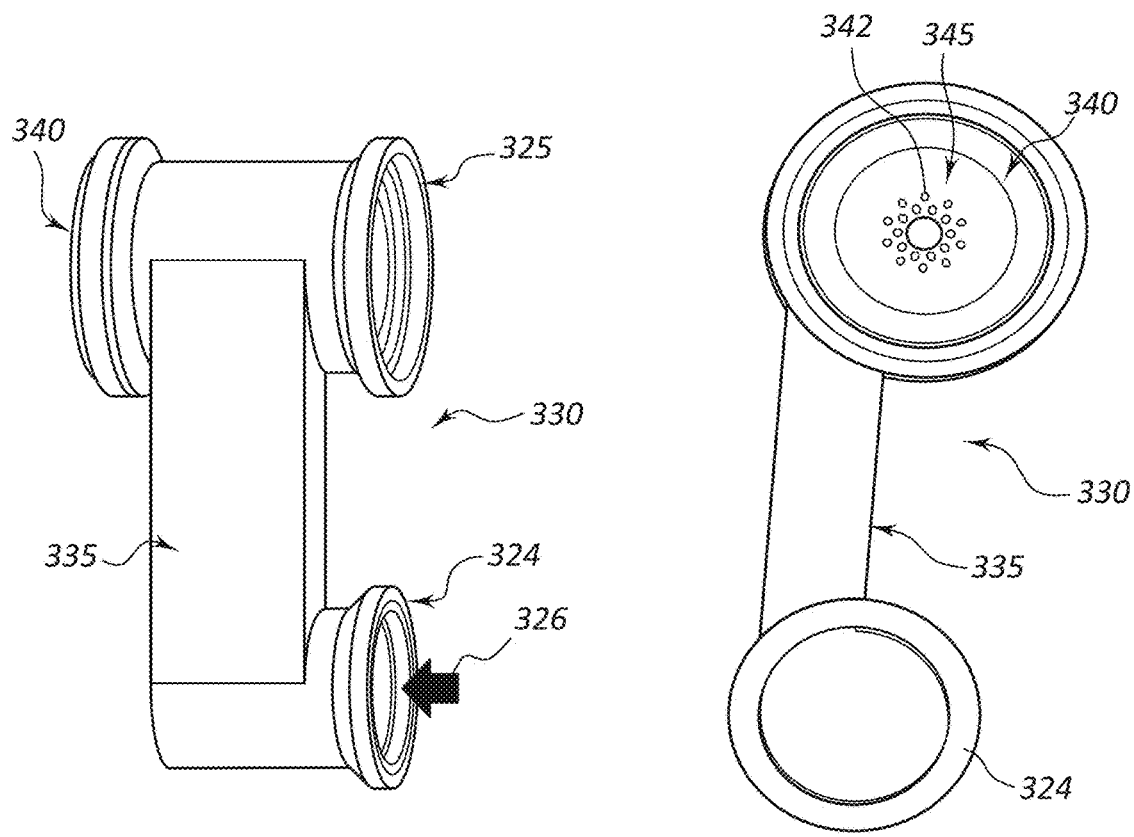
FIG. 3C is a drawing of a cross-sectional view of one embodiment of a dispersion head assembly.
Figure 3C:
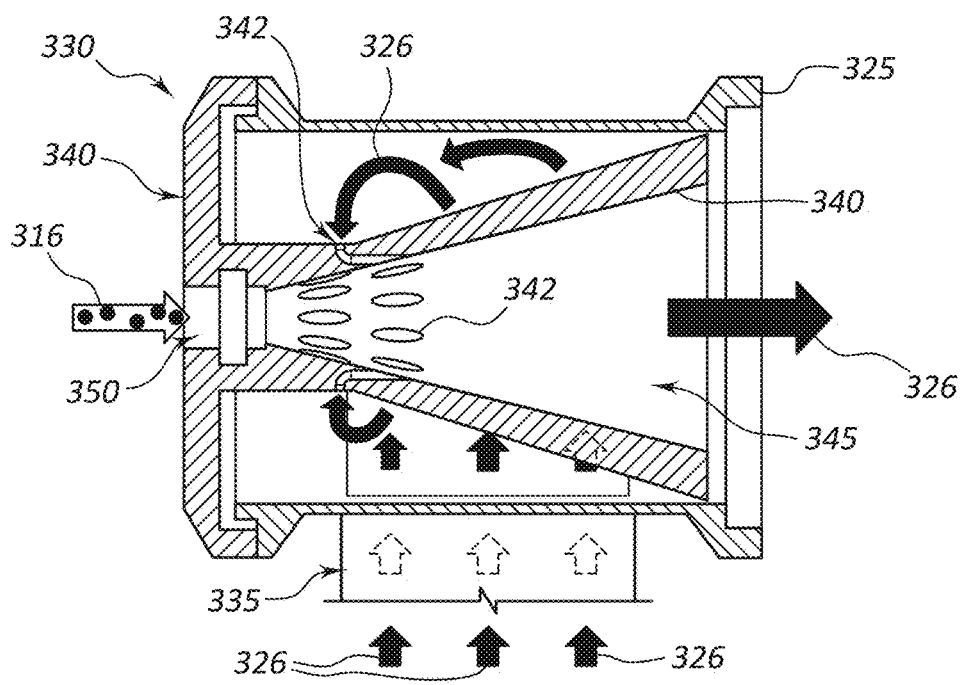

With continued reference to FIG. 2, the mixing zone 230 is configured to mix incoming micronized crystalline material 235 with the conditioning gas 226. In particular embodiments, the mixing zone 230 is configured to mix a delivery gas flow 216 with a conditioning gas 226. In some embodiments of the systems disclosed herein for in-process conditioning of micronized active agents, the mixing zone 230 may comprise a dispersion head assembly configured to mix the delivery gas 216 with the conditioning gas 226. With reference to FIGS. 3A, 3B, and 3C, a dispersion head assembly 330 suitable for use in the systems described herein may include a housing 335 and a mixing head 340, wherein a conditioning gas 326 and a delivery gas 316 may be mixed. The housing 335 comprises a conditioning gas inlet 324 and a gas outlet 325, wherein the conditioning gas 326 may be supplied to the dispersion head assembly 330 through the conditioning gas inlet 324. As shown in FIG. 3C, the conditioning gas 326 may be delivered to the mixing head 340 where it can enter an injection nozzle 345 through an injection inlet 342. The mixing head 340 may also comprise a delivery gas inlet 350 through which the delivery gas 316, having the micronized material entrained therein, may enter the injection nozzle 345. As the delivery gas 316 and the conditioning gas 326 enter the injection nozzle 345 they are mixed together thereby exposing the micronized crystalline material to the conditioning gas 326.

Where a mixing head is included in a system according to the present description, as shown in FIG. 3, the mixing head may be modifiable and interchangeable such that the mixing head 340 may be removed from the dispersion head assembly 330 and modified or exchanged for a different mixing head. The design of the mixing head 340, such as the size, shape, number, and location of one or more injection nozzle inlets 342, may be modified and adjusted to control the mixing dynamics, volume, and/or rate at which the delivery gas and conditioning gas exit the mixing head 340 and are delivered to the conditioning zone 240. In specific embodiments, the design of the mixing head 340, including the size, shape, and location of the delivery gas inlet 350, may be modified and adjusted to control the mixing dynamics and the volume and/or rate of mixed gases that exit the mixing head 340.

Figure 4A:
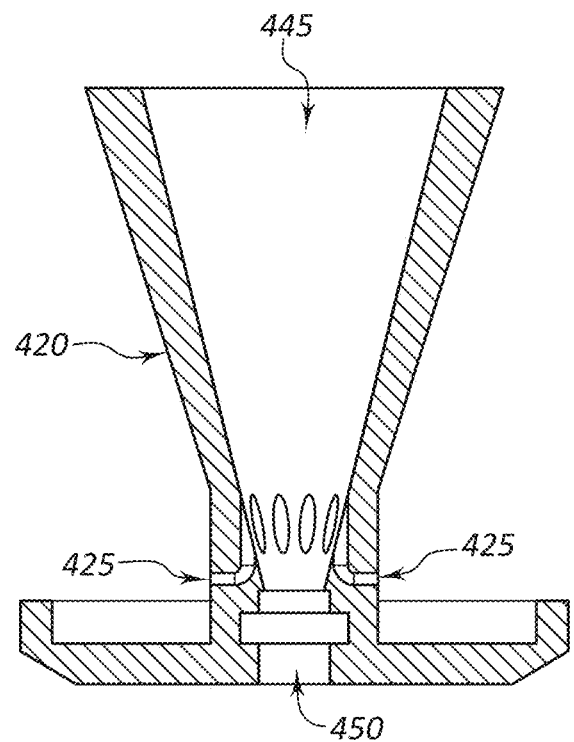
FIG. 4A is a cross-sectional drawing of one embodiment of a mixing head as described in the present disclosure.
Figure 4B:
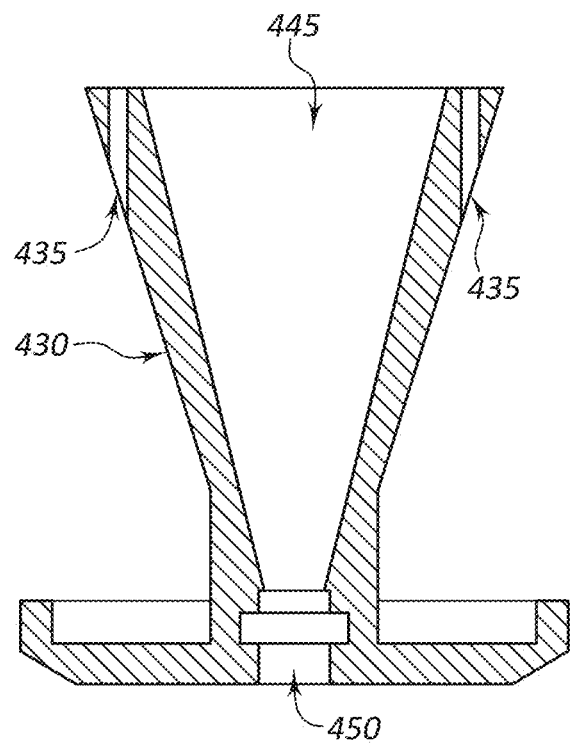
FIG. 4B is a cross-sectional drawing of another embodiment of a mixing head as described in the present disclosure.

In certain embodiments, the dispersion head assembly and/or mixing head may be configured to mix the conditioning gas and the micronized crystalline material upon entry into the conditioning zone 240. Alternatively, the dispersion head assembly and/or mixing head may be configured to mix the conditioning gas and micronized crystalline material before the mixture leaves the mixing zone 230 and is delivered to the conditioning zone 240. For example, FIGS. 4A and 4B provide further embodiments of different mixing heads that may be used in the systems described herein. FIG. 4A shows mixing head 420 comprising delivery gas inlet 450 and injection nozzle inlet 425 located near the base of the injection nozzle 445. FIG. 4B shows a mixing head 430 comprising a delivery gas inlet 450 and injection nozzle inlet 435 located near the edge of the injection nozzle 445. In further embodiments, the mixing heads disclosed herein may include one or more injection nozzle inlets located at desired positions within or around the injection nozzle 445. In other embodiments, the conditioning gas and the micronized crystalline material may be mixed in the injection nozzle 445 before the mixture leaves the mixing zone 230 and is delivered to the conditioning zone 240.

The systems disclosed herein can include a mixing zone 230 configured to mix the conditioning gas 226 with the delivery gas 216 in a desired ratio, such as a ratio of gas volumes (volume/volume) or a mass flow rate ratio (SCFM/SCFM). For example, in particular embodiments, the mixing zone, including, for example, a dispersion head assembly, may be configured to mix the conditioning gas 226 and delivery gas 216 in a ratio of about 1 to 4 parts conditioning gas 226 with about 1 part of the delivery gas 216. In certain such embodiments, the conditioning gas 226 may be mixed with the delivery gas 216 in a ratio selected from any of about 1:1, 1.2:1, 1.4:1, 1.6:1, 1.8:1, 2.0:1, 2.2:1, 2.4:1, 2.6:1, 2.8:1, 3:1, 3.2:1, 3.4:1, 3.6:1, 3.8:1, and 4:1.

With continued reference to FIG. 2, the conditioning zone 240 (also referred to herein as a "conditioning chamber") included in the systems described herein is configured to contain and maintain a controlled atmosphere tailored to the conditioning of a desired micronized material and to receive the delivery gas 216 and conditioning gas 226 from the mixing zone 230. As noted above, in some embodiments, the conditioning chamber 240 and mixing zone 230 may be provided as separate subsystems placed in fluid communication one with another. Alternatively, the mixing zone 230 and conditioning chamber 240 may be integrated such that two different subsystems are not required. Where, provided as separate subsystems, the mixing zone 230 and conditioning chamber 240 are configured such that the mixed delivery gas 216 and conditioning gas 226 are delivered into the conditioning chamber 240 from the mixing zone 230.

In certain embodiments, after the conditioning gas 226 and the delivery gas 216, comprising micronized active agent particles, are mixed together in the mixing zone 230, the micronized particles 235 enter the conditioning chamber 240 together with the conditioning gas 226. While in the conditioning chamber 240, the micronized particles 235 are exposed for a desired time period to the conditioning gas 226, and during their residence time within the conditioning chamber 240, the amorphous material included in the micronized particles 235 anneals. The residence time of the micronized particles 235 in the conditioning chamber 240 may be controlled by one or more of the following: the dimension and geometry of the conditioning chamber 240; the rate at which the mixture of the conditioning gas 226 and the delivery gas 216 are delivered into the conditioning chamber 240; the flow pattern of the mixture of the conditioning gas 226 and the delivery gas 216 within the conditioning chamber 240; the amount of micronized material carried by the mixture of delivery gas 216 and conditioning gas 226; and the system used for collection of the conditioned micronized material. In particular embodiments, the residence time of the micronized active agent particles 235 within the conditioning chamber 240 may be for a period of time ranging from about 0.5 to 10 seconds. In certain such embodiments, the residence time of the micronized particles 235 within the conditioning chamber 240 may be selected from one the residence times detailed herein.

A conditioning chamber 240 suitable for use in the systems described may be configured as for example, a tank, a column, a funnel, a tube, or other appropriate devices or structures. In further embodiments, the conditioning chamber 240 may further include heaters, inlets, outlets, and other means and devices for controlling the conditions and gas flow within the conditioning chamber 240. The geometry of the conditioning chamber 240 may be modified by adjusting, for example, the length, width, height, volume, and shape of the conditioning chamber 240.

Conditioned micronized active agent particles 246 are separated from the conditioning gas 226 in a separating zone 250. The separating zone 250 may comprise elements or devices designed to separate conditioned micronized active agent particles 246 from the carrier gas 216 and conditioning gas 226, such as, for example, a cyclone separator, bag collector or other separation equipment, as known by those of skill in the art. In particular embodiments, the separating zone 250 may comprise an exhaust outlet 255 whereby, for example, the exhaust gas and other materials may exit from the separating zone 250. Though micronized material will have been conditioned within the conditioning zone 240, in certain embodiments, the process of annealing is does not end immediately upon collection of the micronized material from the conditioning zone 240. For example, in certain embodiments, although the controlled atmosphere of the conditioning zone 240 initiates or even substantially completes the annealing process, annealing of amorphous material continues as the micronized material exits the conditioning zone 240 and is separated and collected. In addition to a system or device of separating the conditioned micronized material from the delivery and conditioning gases, the separating zone 250 may further included one or more filters and collectors. Filters may be placed, for example, at the exhaust outlet 255 to capture or prevent unwanted escape of fines. Additionally, a collector 260 is included within the separating zone 250 to facilitate capture and containment of the conditioned material. Once collected the, conditioned crystalline material can be stored or further processed, as desired.

Though FIG. 1 and FIG. 2 illustrate conditioning systems having a single conditioning zone, systems according to the present description may also include multiple conditioning zones. In such embodiments, the different conditioning zones may expose the crystalline particulate material to different annealing conditions. Such systems, therefore, can be configured to provide multiple in-process conditioning steps. FIG. 19 and FIG. 20 provide schematic illustrations of two embodiments of conditioning systems that provide two conditioning zones, thereby facilitating multiple annealing steps within a single system.

As shown in FIG. 19, a conditioning system 600 as described herein may include a delivery zone 610, a conditioning gas supply zone 620, a mixing zone 630, a conditioning zone 640, and a collection zone 650, as described herein. In addition, the system may include a product holding chamber 660 that is separated from the collection zone 650 by, for example, a cut-off valve 670. In such an embodiment, the conditioning system can be configured as described in relation to the systems illustrated in FIG. 1 and FIG. 2, and the system can be adapted for annealing a wide range of materials using any suitable process conditions described herein. As conditioned product is collected in the collection zone 650, the cut-off valve 670 remains open and conditioned product is delivered to the product holding chamber 660. The product holding chamber 660 can be configured to maintain the conditioning product in a continuously fluidized state. The cut-off valve 670 can be any valve mechanism suited to use in this context, that can be cycled between open and closed states, and when closed provides a physical barrier capable of separating the conditioned material from collection zone 650. In certain embodiments, the cut-off valve 670 seals the product holding chamber 660 from the collection zone 650 such that, once closed, the conditioned product will not regress into the collection zone 650 and process gases (e.g., delivery gas or conditioning gas) do not pass between the collection zone 650 and the product holding chamber 660.

Once delivered to the product holding chamber 660, the conditioned product may be maintained in a fluidized state and the cut-off valve 670 closed. At that point, the system can re-equilibrate to supply a secondary conditioning gas. In such an embodiment, the upstream components of the conditioning system 600 (e.g., the delivery zone 610, conditioning gas supply zone 620, mixing zone 630, conditioning zone 640, and collection zone 650) may be purged of the primary conditioning gas used to condition the material present in the product holding chamber 660, and a secondary conditioning gas can be supplied from and/or generated in the gas supply zone 620. Once the system is re-equilibrated with the secondary conditioning gas, the cut-off valve 670 may be opened to expose the conditioned product contained within the product holding chamber 660 to the secondary conditioning gas. The product can be maintained in a continuously fluidized state within the product holding chamber 660 as it is exposed to the secondary conditioning gas for a period of time sufficient to accomplish a secondary annealing. The nature and content of the secondary conditioning gas, including the presence and concentration of one or more solvents, and the temperature, flow rate, and direction or turbulence of flow of the secondary conditioning gas may be adjusted to accomplish a desired secondary annealing for a wide range of selected materials using process conditions described herein. By adjusting the characteristics of the secondary conditioning gas and the residence time of the particulate material within the product holding chamber 660, the system illustrated in FIG. 19 can be utilized to provide multiple conditioning steps using a single system.

The residence time of the conditioned product within the holding chamber 660 can be easily adjusted based on the material itself, the conditioning gas(es), and the nature or extent of annealing desired. For example, as is true of particles conditioned within a conditioning zone, the residence time of a conditioned product within a holding chamber 660 may be a matter of seconds or minutes. For example the residence time of the conditioned material within the holding chamber 660 may be selected from those residence times detailed above in relation to the conditioning zone. However, the conditioned product can also be maintained within the holding chamber 660 indefinitely. In certain embodiments, the conditioned product is maintained within a holding chamber 660 for a time selected from up to 5 minutes, up to 10 minutes, up to 30 minutes, up to 1 hour, up to 1.5 hours, up to 2 hours, up to 5 hours, up to 10 hours, up to 12 hours, up to 18 hours, and up to 24 hours. Such flexibility enables the conditioned product to be exposed to a secondary conditioning gas for any amount of time needed to accomplish secondary conditioning. A relatively longer residence time affords exposure to a secondary conditioning gas over a long period of time and may be particularly useful for a secondary conditioning process that requires more time than might be practically achieved within a given system's conditioning zone.

Figure 20:
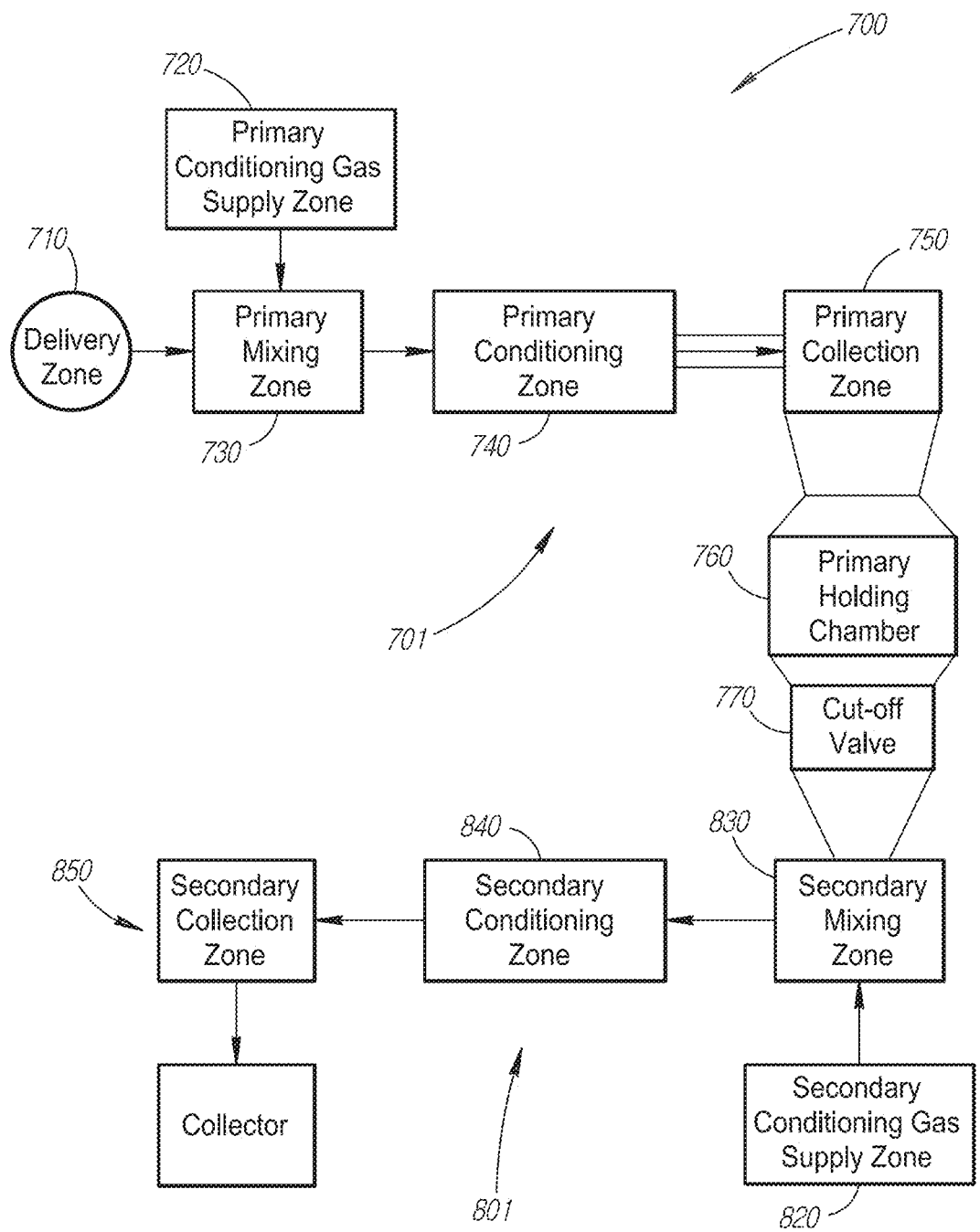
FIG. 20 is a diagram showing another embodiment of a system disclosed herein configured to facilitate multiple conditioning steps.

FIG. 20 illustrates a conditioning system 700 that includes two conditioning subsystems, a primary conditioning system 701 and secondary conditioning system 801. The primary conditioning system 701, includes a delivery zone 710, a primary conditioning gas supply zone 720, a primary mixing zone 730, a primary conditioning zone 740, and a primary collection zone 750. The primary conditioning system 701 and the secondary conditioning system 801 may be separated by, for example, a primary holding chamber 760 and one or more cut-off valve 770 (only a single cut-off valve is shown). The primary holding chamber 760 may be configured for maintaining conditioned product received from the primary conditioning system 701 in a continuously fluidized state, and the cut-off valve 770 can be any valve mechanism suited to use in this context, that can be cycled between open and closed states, and when closed provides a physical barrier capable of isolating the primary and secondary conditioning systems 701, 801. In certain embodiments, the cut-off valve 770 seals the primary holding chamber 760 from the secondary conditioning system 801 such that, when closed, product collected from the primary conditioning system 701 will not pass into the secondary conditioning system 801, material transferred to the secondary conditioning system 801 will not regress into the primary conditioning system 701, and process gases (e.g., delivery gas or conditioning gas) do not pass between the primary and secondary conditioning systems 701, 801. In some embodiments, a second cut-off valve (not shown) can be positioned between the primary holding chamber 760 and the primary collection zone 750. Such a configuration may be particularly advantageous where communication of process gases between the primary and secondary conditioning systems 701, 801 must be minimized.

As shown in FIG. 20, the secondary conditioning system 801 may include a secondary conditioning gas supply zone 820, a secondary mixing zone 830, a secondary conditioning zone 840, and a secondary collection zone 850. In the embodiment illustrated in FIG. 20, the primary and secondary conditioning systems 701, 801 can be configured as described in relation to the systems illustrated in FIG. 1 and FIG. 2, and the systems can be adapted for conditioning a wide range of materials using any process conditions described herein.

As material is processed in the primary conditioning system 701 a primary annealing of the material takes place and the primary annealed material is collected in the primary collection zone 750 and delivered to the primary holding chamber 760. While the product is processed in the primary conditioning system 701 and collected in the primary holding chamber 760, the cut-off valve 770 will typically remain closed. Once the first conditioning process is complete and the primary annealed material is collected in the primary holding chamber 760, the cut-off valve 770 may be opened and the primary annealed material delivered into the secondary mixing zone 830. The primary annealed material may be dispersed within a delivery gas as it is delivered to or within the secondary mixing zone 830. The delivery gas can be any suitable delivery gas as described herein, and by dispersing the primary annealed product in a delivery gas, the primary annealed product is suspended or entrained within the delivery gas. A secondary conditioning gas is delivered and/or generated within the secondary conditioning gas supply zone 820, and the secondary conditioning gas is mixed with the primary annealed product (and any delivery gas used to disperse the primary annealed product) in the secondary mixing zone 830.

The primary annealed product remains entrained, suspended or aerosolized in the secondary conditioning gas within the secondary conditioning zone 840. The primary annealed product is maintained within the secondary conditioning zone 840 for a period of time sufficient to accomplish a secondary annealing. As is true of the conditioning gas utilized in each embodiment of the systems described herein, the nature and content of the secondary conditioning gas, including the presence and concentration of one or more solvents, and the temperature, flow rate, and direction or turbulence of flow of the secondary conditioning gas may be adjusted to accomplish a desired secondary annealing for a wide range of selected materials using process conditions described herein. By adjusting the characteristics of the secondary conditioning gas and the residence time of the particulate material within the secondary conditioning zone 840, the system illustrated in FIG. 20 can be utilized to provide multiple conditioning steps using a single system.

Though described in relation to embodiments illustrated in the figures provided herein, conditioning systems according to the present description are not limited to the specific, illustrated embodiments. The systems for conditioning crystalline particulate materials described herein are scalable and adaptable for areas of various size. In particular embodiments, the systems disclosed herein may be scaled-up or scaled-down with regard to, for example, gas flow rates, active agent mass, material output, desired particle residence time, etc., according the desired output rate and the available space and equipment. In certain embodiments, the systems disclosed herein may be assembled as a modular unit and incorporated or built into established processes and systems for the manufacture of conditioned particulate material, and are well-suited for efficient production of conditioned, micronized particulates. For example, the systems as disclosed here may be incorporated into commercial milling and micronization processes or a built into a spray drying system. In further embodiments, the systems described herein may be operated as part of a batch process where one or more micronized materials are conditioned and then collected in separate batches. In alternative embodiments, the systems described herein may be operated as part of a continuous feed process whereby one or more micronized materials are continuously delivered to the system and continuously conditioned and collected.

III. Methods for Conditioning Particulate Crystalline Material

Methods for conditioning particulate crystalline material are also provided herein. Methods according to the present description can be carried out using the conditioning systems provided herein. In general, the methods described herein include: (1) generating and/or providing a crystalline particulate material; (2) introducing the particulate material in an atmosphere where it is blended with a conditioning gas; (3) maintaining the particulate material in contact with the conditioning gas for a desired residence time; and (4) collecting the conditioned particulate material. In specific embodiments, the particulate material is a micronized crystalline material. Examples of materials that may be conditioned using the methods described herein include those materials already described. In particular embodiments of methods according to the present description, the material to be conditioned is typically entrained or aerosolized within a delivery gas that is blended with the conditioning gas, and the particulate material remains entrained, suspended or aerosolized in the conditioning gas as it travels through the conditioning zone. The nature of the conditioning gas and the residence time of the particulate material within the conditioning zone are controlled to accomplish annealing of the material.

In specific embodiments, the methods include a continuous process for micronizing, conditioning, and collecting a crystalline material. In such embodiments, generating the crystalline material includes subjecting the material to a micronization process and conditioning of the micronized material may be conducted in-line with particle collection. Where, the methods described herein provide in-line or in-process conditioning of micronized material (or, more generally, any size comminuted material), the particulate material may be blended with a conditioning gas and retained within a conditioning zone to anneal the particulate prior to particle collection.

In other embodiments, methods according to the present description include primary and secondary conditioning steps. In such embodiments, the crystalline particulate material can be introduced into (e.g., entrained, suspended, or aerosolized within) a first conditioning gas to carry out a primary annealing and subsequently introduced into (e.g., entrained, suspended, or aerosolized within) a second conditioning gas to carry out a secondary annealing. Alternatively, for certain materials, a conditioning gas may be selected that provides substantially simultaneous primary and secondary annealing of the particulate material. For example, in methods where primary and secondary annealing are carried out using a single conditioning gas, the conditioning gas may anneal the particulate material through both reduction of amorphous content and removal of an undesired residual solvent by vaporization or solvent replacement.

The methods provided can be tailored to specific materials to be processed. For example, glycopyrronium is an active agent that can be conditioning using the systems and methods described herein. Micronization of crystalline glycopyrronium can lead to a micronized material that includes significant amorphous content, and in particular embodiments, the present methods can be adapted to reduce or eliminate amorphous material from crystalline glycopyrronium particulates. Glycopyrronium conditioned according to the present description may be in any crystalline form, isomeric form or mixture of isomeric forms. In this regard, the form of glycopyrronium may be selected to optimize the activity and/or stability of glycopyrronium. Where appropriate, glycopyrronium may be provided as a salt (e.g. alkali metal or amine salts, or as acid addition salts), esters or solvate (hydrates). Suitable counter ions include, for example, fluoride, chloride, bromide, iodide, nitrate, sulfate, phosphate, formate, acetate, trifluoroacetate, propionate, butyrate, lactate, citrate, tartrate, malate, maleate, succinate, benzoate, p-chlorobenzoate, diphenyl-acetate or triphenylacetate, o-hydroxybenzoate, p-hydroxybenzoate, 1-hydroxynaphthalene-2-carboxylate, 3-hydroxynaphthalene-2-carboxylate, methanesulfonate and benzenesulfonate. In particular embodiments of the methods described herein, the bromide salt of glycopyrronium is used, namely (3-[(cyclopentylhydroxyphenylacetyl)oxy]-1, 1-dimethylpyrrolidinium bromide). The bromide salt of glycopyrronium is commonly referred to as glycopyrrolate. Glycopyrrolate is commercially available and can be prepared according to the procedures set out in U.S. Pat. No. 2,956,062, the contents of which are incorporated herein by reference.

Where crystalline glycopyrronium, such as crystalline glycopyrrolate, is the material processed by the methods described herein, the glycopyrronium material can be micronized to exhibit particle size characteristics as described herein, such as, for example, a particle size distribution suitable for pulmonary delivery. Moreover, the micronized glycopyrronium can be prepared and provided using any suitable micronization technique and delivered into the conditioning chamber via a delivery gas suitable to the chosen micronization technique. In one such embodiment, the glycopyrronium is micronized via a jet mill and the delivery gas may be typical gas flow exiting the jet mill, which would include aerosolized, micronized particles of glycopyrronium.

In specific embodiments, the bromide salt of glycopyrronium (glycopyrrolate) may be processed according to the present methods. Where glycopyrrolate is the material being conditioned, a conditioning gas may be mixed with a delivery gas (e.g., a jet mill gas flow) in a ratio of about 1 to 4 parts conditioning gas flow with about 1 part of the delivery gas. In certain such embodiments, the conditioning gas flow may be mixed with the jet mill gas flow in a ratio selected from about 1:1, 1.2:1, 1.4:1, 1.6:1, 1.8:1, 2.0:1, 2.2:1, 2.4:1, 2.6:1, 2.8:1, 3:1, 3.2:1, 3.4:1, 3.6:1, 3.8:1, and 4:1. In specific embodiments, the conditioning gas may be supplied at a gas flow rate ranging from about 150 SCFM up to about 500 SCFM, and the delivery gas may be supplied at a gas flow rate of ranging from about 20 SCFM up to about 75 SCFM. However, in some embodiments, depending on the desired conditions for the conditioning zone and the nature of the material being processed, the gas flow rate of both the conditioning gas and the delivery gas may be increased as high as 3,300 SCFM.

When conditioning glycopyrrolate, the conditioning gas may be delivered at a temperature ranging from about 20° C. to about 30° C. and include water vapor as a solvent. In particular embodiments of methods for conditioning glycopyrrolate, the temperature of the conditioning gas may be selected from at least 20° C., 21° C., 22° C., 23° C., 24° C., 25° C., 26° C., 27° C., 28° C., 29° C., and 30° C. Moreover, where included in the conditioning gas for annealing glycopyrrolate according to the methods described herein, water vapor may be provided at a concentration that results in a relative humidity ranging from about 50% to about 80%.

In particular embodiments of methods for conditioning glycopyrrolate, the conditioning gas may be supplied at a temperature described herein with a relative humidity selected from at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74% and 75%. At the temperatures and relative humidity described herein, the residence time of the micronized glycopyrrolate material within the conditioning chamber may be from about 0.5 to about 10 seconds. In certain such embodiments, the micronized glycopyrrolate material is present within the conditioning chamber for a residence time selected from about 0.5 seconds, about 1 second, about 1.5 seconds, about 2 seconds, about 2.5 seconds, about 3 seconds, about 3.5 seconds, about 4 seconds, about 5 seconds, about 6 seconds, about 7 seconds, about 8 seconds, about 9 seconds, and about 10 seconds. However, the residence time can be adjusted as needed to achieve the desired reduction of amorphous content.

In other embodiments, the methods provided can be tailored to for the annealing of materials soluble in organic solvents. For example, the methods described herein can be tailored to the conditioning of corticosteroid active agents soluble in organic solvents. In certain such embodiments, the methods described herein can be tailored for the conditioning of a corticosteroid selected from fluticasone and budesonide. Fluticasone, pharmaceutically acceptable salts of fluticasone, such as fluticasone propionate, and preparation of such materials are known, and described, for example, in U.S. Pat. Nos. 4,335,121, 4,187,301, and U.S. Patent Publication No. US2008/125407, the contents of which are incorporated herein by reference. Budesonide is also well known and described, for example, in U.S. Pat. No. 3,929,768, the contents of which are incorporated herein by reference.

Micronization of crystalline corticosteroids, such as budesonide and fluticasone, can lead to a micronized material that includes significant amorphous content, and in particular embodiments, the present methods can be adapted to reduce or eliminate amorphous material from particulate crystalline corticosteroid material. A corticosteroid conditioned according to the present description may be in any crystalline form, isomeric form or mixture of isomeric forms. In this regard, the form of the corticosteroid may be selected to optimize the activity and/or stability of corticosteroid. Where appropriate, the corticosteroid may be provided as a salt (e.g. alkali metal or amine salts, or as acid addition salts), esters or solvate (hydrates).

Where a crystalline corticosteroid material, such as crystalline fluticasone or budesonide, is the material processed by the methods described herein, the corticosteroid material can be micronized to exhibit particle size characteristics as described herein, such as a particle size distribution suitable for pulmonary delivery. Moreover, the micronized corticosteroid can be prepared and provided using any suitable micronization technique and delivered into the conditioning chamber via a delivery gas suitable to the chosen micronization technique. In one such embodiment, the selected corticosteroid is micronized via a jet mill and the delivery gas may be typical gas flow exiting the jet mill, which would include aerosolized, micronized particles of the corticosteroid.

In specific embodiments, the corticosteroid to be processed according to the present methods is selected from fluticasone propionate and budesonide. In such embodiments, a conditioning gas may be mixed with a delivery gas (e.g., a jet mill gas flow) in a ratio of about 1 to 4 parts conditioning gas flow with about 1 part of the delivery gas. In certain such embodiments, the conditioning gas flow may be mixed with the jet mill gas flow in a ratio selected from about 1:1, 1.2:1, 1.4:1, 1.6:1, 1.8:1, 2.0:1, 2.2:1, 2.4:1, 2.6:1, 2.8:1, 3:1, 3.2:1, 3.4:1, 3.6:1, 3.8:1, and 4:1. In specific embodiments, the conditioning gas may be supplied at a gas flow rate ranging from about 150 SCFM up to about 500 SCFM and the delivery gas may be supplied at a gas flow rate of ranging from about 20 SCFM up to about 75 SCFM. However, in some embodiments, depending on the desired conditions for the conditioning zone and the nature of the material being processed, the gas flow rate of both the conditioning gas and the delivery gas may be increased as high as 3,300 SCFM.

When conditioning a corticosteroid exhibiting solubility in an organic solvent, such as fluticasone propionate or budesonide, the conditioning gas may be delivered at a temperature ranging from about 20° C. to about 30° C. and include an organic solvent vapor as a solvent. In particular embodiments of methods for conditioning a corticosteroid, including a corticosteroid selected from fluticasone propionate and budesonide, the temperature of the conditioning gas may be selected from at least 20° C., 21° C., 22° C., 23° C., 24° C., 25° C., 26° C., 27° C., 28° C., 29° C., and 30° C.

Moreover, where included in the conditioning gas, the organic solvent vapor may be provided within the conditioning gas to provide a relative saturation of the solvent in the conditioning zone ranging from about 10% to about 95%. Suitable organic solvents include an alcohol (e.g., ethanol, methanol, isopropyl alcohol, etc.), ketone (e.g., acetone, methyl ketone, ethyl ketone, etc.), ester (e.g., ethyl acetate, etc.), aliphatic alcohol (e.g., octanol, etc.), or alkane (e.g., octane, nonane, etc.). In specific embodiments for the conditioning of corticosteroid materials, including corticosteroids selected from fluticasone propionate and budesonide, the organic solvent vapor may be provided within the conditioning gas to provide a relative saturation of the solvent in the conditioning zone ranging from about 50% to about 80%. For example, in embodiments of methods for conditioning corticosteroid materials, including corticosteroids selected from fluticasone propionate and budesonide, the conditioning gas may be supplied at a temperature described herein with a relative solvent saturation selected from at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74% and 75%. At the temperatures and relative solvent saturation described herein, the residence time of the micronized corticosteroid material within the conditioning chamber may be from about 0.5 to about 10 seconds. In certain such embodiments, the micronized corticosteroid material is present within the conditioning chamber for a residence time selected from about 0.5 seconds, about 1 second, about 1.5 seconds, about 2 seconds, about 2.5 seconds, about 3 seconds, about 3.5 seconds, about 4 seconds, about 5 seconds, about 6 seconds, about 7 seconds, about 8 seconds, about 9 seconds, and about 10 seconds. However, the residence time can be adjusted as needed to achieve the desired conditioning.

As is further evidenced by the experimental examples that follow, methods according to the present description can be adapted to accomplish conditioning of varying materials exhibiting divergent physical and chemical properties.

IV. Exemplary Embodiments

In specific embodiments, methods for conditioning a particulate crystalline material (e.g., micronized crystalline material) according to the present description include: providing aerosolized micronized crystalline particles, wherein said micronized crystalline particles contain one or both of an amorphous material and a residual solvent; continuously mixing the micronized crystalline particles with a conditioning gas comprising a carrier gas and a conditioning vapor in a chamber connected directly to the exit of a micronization apparatus; maintaining the micronized crystalline particles in contact with the conditioning gas for sufficient time to result in annealing of said micronized crystalline particles, wherein said annealing results in a phase transformation; and separating the micronized crystalline particles from the conditioning gas. As detailed herein, such a phase transformation refers to a change in the bulk of the crystals present in a particulate crystalline material. In such embodiments, the phase transformation may be selected from removal of a solvent of crystallization, replacement of a solvent of crystallization, an amorphous to crystalline phase change, or a change in physical structure beyond just an amorphous to crystalline phase change.

The material (e.g., micronized crystalline material) processed according to any method described herein may be mixed with the conditioning gas for between about 0.1 to 600 seconds before the micronized crystalline material exits the conditioning zone.

The material (e.g., micronized crystalline material) processed according to any method described herein may be mixed with the conditioning gas for between about 2 to 6 seconds before the material exits the conditioning zone.

The material (e.g., micronized crystalline material) processed according to any method described herein may be mixed with the conditioning gas for about 3 seconds before the micronized crystalline material exits the conditioning zone.

The material (e.g., micronized crystalline material) processed according to methods described herein may be water soluble. Where the material to be processed according to a method described herein is water soluble, the conditioning gas may include a solvent vapor that is an aqueous solvent vapor, and the conditioning gas may be provided at a temperature ranging from about 20° C. to 100° C. and at a relative humidity ranging from about 0.05% to 95%.

The material (e.g., micronized crystalline material) processed according methods described herein may not be water soluble (e.g., soluble in one or more organic solvents). Where the material to be processed according to a method described herein is not water soluble the conditioning gas may include a solvent vapor that is an organic solvent vapor, and the conditioning gas may be provided at a temperature ranging from about 20° C. to 100° C. and at a vapor pressure of a non-aqueous solvent in the range of about 0.05% to 95%.

The material (e.g., micronized crystalline material) processed according to methods described herein may be an admixture of water soluble and non-water soluble materials. In such instances, the conditioning gas may include a solvent vapor that includes an aqueous solvent vapor and an organic solvent vapor, and the conditioning gas may be supplied at a temperature ranging from about 10° C. to 100° C. and at a relative humidity of the aqueous solvent in the range of about 0.05% to 95% and a vapor pressure of the non-aqueous solvent in the range of about 0.05% to 95%.

In any of the methods described herein, the material (e.g., micronized crystalline material) to be processed may be entrained, suspended, or aerosolized within a delivery gas before mixing with a conditioning gas. In such embodiments, the material may be produced using a jet mill and aerosolized in the jet mill gas flow.

In any of the embodiments of the methods and systems described herein, the conditioning gas may be mixed with the particulate material (e.g., an aerosolized micronized crystalline material) in a ratio of about 1 to 10 parts conditioning gas with about 1 part of the aerosolized micronized crystalline material. In such embodiments, the aerosolized micronized crystalline material may be entrained, suspended or aerosolized within a delivery gas.

In any of the embodiments of the systems and methods described herein, the conditioning gas may be supplied at a flow rate ranging from about 25 standard cubic feet per minute (SCFM) up to about 300 SCFM while mixing with the particulate crystalline material.

In any of the embodiments of the systems and methods described herein, the particulate material (e.g., micronized crystalline material) may be entrained, suspended or aerosolized within a delivery gas and the aerosolized particulate material supplied at a flow rate ranging from about 25 standard cubic feet per minute (SCFM) up to about 200 SCFM while mixing with a conditioning gas.

In any of the embodiments of the systems and methods described herein, the conditioning gas may comprise nitrogen gas.

In any of the embodiments of the systems and methods described herein, the particulate material (e.g., micronized crystalline material) may be mixed with the conditioning gas in a closed chamber.

In any of the embodiments of the systems and methods described herein, the particulate material (e.g., micronized crystalline material) may be one of glycopyrronium, including glycopyrrolate, dexipirronium, scopolamine, tropicamide, pirenzepine, dimenhydrinate, tiotropium, darotropium, aclidinium, umeclidinium, trospium, ipatropium, atropine, benzatropin, oxitropium, ephedrine, adrenaline, fenoterol, formoterol, isoprenaline, metaproterenol, salbutamol, albuterol, salmeterol, terbutaline, fluticasone, including fluticasone propionate, budesonide, mometasone, ciclesonide, and Compound A.

In specific embodiments, systems for conditioning a particulate crystalline material (e.g., micronized crystalline material) according to the present description include: a delivery zone for delivering the particulate material; a mixing zone in fluid communication with the delivery zone, wherein the particulate crystalline material is delivered from the micronizing zone to the mixing zone and therein mixed with a conditioning gas; a conditioning gas supply zone in fluid communication with the mixing zone, the conditioning gas supply zone providing the conditioning gas at a desired temperature and solvent vapor concentration to the mixing zone to be mixed with the particulate crystalline material; a conditioning zone in fluid communication with the mixing zone, wherein the mixture of the particulate crystalline material and the conditioning gas is delivered and remains in the conditioning zone for a desired residence time; and a separation and collection zone, wherein the conditioned particulate crystalline material is separated from the conditioning gas and the conditioned material is collected. In certain such embodiments, the delivery zone may be a micronizing zone comprising a device for micronizing the particulate crystalline material.

In particular embodiments, the systems described herein are configured to process a particulate crystalline material (e.g., micronized crystalline material) that is water soluble and the conditioning gas supply zone is configured to provide a conditioning gas that includes a water vapor at a temperature ranging from about 20° C. to 100° C. and at a humidity ranging from about 0.05% to 90% relative humidity.

In particular embodiments, the systems described herein are configured to process a particulate crystalline material (e.g., micronized crystalline material) that is not water soluble and the conditioning gas supply zone is configured to provide a conditioning gas that includes an non-aqueous (e.g. an organic solvent as described herein) vapor at a temperature ranging from about 20° C. to 100° C. and at a vapor pressure of a non-aqueous solvent in the range of about 0.05% to 90%.

In particular embodiments, the systems described herein are configured to process a particulate crystalline material (e.g., micronized crystalline material) that is an admixture of water soluble and non-water soluble materials, and the conditioning gas supply zone is configured to provide the conditioning gas at a temperature ranging from about 20° C. to 30° C. and at a relative humidity of 50 to 75% and vapor pressure of a non-aqueous solvent in the range of about 50% to 75%.

In any of the embodiments described herein, the system for conditioning particulate material may include a conditioning gas supply zone configured to provide a conditioning gas at a temperature of about 25° C. and with a humidity of about 65% relative humidity In any of the embodiments described herein, the system for conditioning particulate material may include a conditioning zone configured to maintain the mixture of the particulate material (e.g., micronized crystalline material) and the conditioning gas within the conditioning zone for a residence time of between about 0.5 to 60 seconds. For example, the systems for conditioning particulate material described herein may include a conditioning zone configured to maintain a mixture of the particulate crystalline material and the conditioning gas within the conditioning zone for a residence time of between about 1 to about 10 seconds. In even more specific embodiments, the systems for conditioning particulate material described herein may include a conditioning zone configured to maintain a mixture of the particulate crystalline material and the conditioning gas within the conditioning zone for a residence time of about 3 seconds.

In any of the embodiments described herein including a delivery zone that comprises a device for micronizing the particulate crystalline material (i.e., a micronizing zone), the device for micronizing the particulate crystalline material may be a jet mill or any other suitable system or device as described herein.

In any of the embodiments described herein, the systems for conditioning a particulate material may be configured for conditioning a material selected from a particulate crystalline material (e.g., micronized crystalline material) selected from at least one of glycopyrronium, including glycopyrrolate, dexipirronium, scopolamine, tropicamide, pirenzepine, dimenhydrinate, tiotropium, darotropium, aclidinium, umeclidinium, trospium, ipatropium, atropine, benzatropin, oxitropium, ephedrine, adrenaline, fenoterol, formoterol, isoprenaline, metaproterenol, salbutamol, albuterol, salmeterol, terbutaline, fluticasone, including fluticasone propionate, budesonide, mometasone, ciclesonide, and Compound A.

In particular embodiments of the systems described herein, the systems may be configured for conditioning a particulate glycopyrrolate material using any of the process conditions detailed herein. In certain such embodiments, the systems described herein can be configured for micronizing a crystalline glycopyrrolate material. In such embodiments, the systems may include a micronizing zone with a jet mill for micronizing glycopyrrolate. In certain such embodiments, the jet mill gas may be a delivery gas and mixed with a conditioning gas within the mixing zone at a ratio of from about 1 to 4 parts conditioning gas mixed with about 1 part of the jet mill gas.

In any of the embodiments described herein, the systems for conditioning a particulate crystalline material (e.g., micronized crystalline material) may include a conditioning gas supply zone configured to provide the conditioning gas to the mixing zone at a flow rate ranging from about 150 standard cubic feet per minute (SCFM) up to about 300 SCFM.

In any of the embodiments described herein, the systems for conditioning a particulate crystalline material (e.g., micronized crystalline material) may be configured to entrain, suspend, or aerosolize the particulate material within a delivery gas before the material is introduced to a mixing zone or blended with a conditioning gas. In any of the embodiments described herein, the systems for conditioning a particulate crystalline material (e.g., micronized crystalline material) may be configured to deliver the particulate material in a delivery gas at a flow rate ranging from about 35 standard cubic feet per minute (SCFM) up to about 200 SCFM.

In any of the embodiments described herein, the systems for conditioning a particulate crystalline material (e.g., micronized crystalline material) may be configured to include a mixing zone that comprises a dispersion head assembly wherein the conditioning gas and the micronized crystalline material are mixed. In such embodiments, the dispersion head assembly may include a mixing head configured to control the mixing of the conditioning gas and the particulate crystalline material. Where a system as described herein includes a mixing head, the mixing head may be configured to include an injection nozzle inlet configured to deliver the conditioning gas to an injection nozzle and a delivery gas inlet configured to deliver the micronized crystalline material to the injection nozzle.

In any of the embodiments described herein, the systems for conditioning a particulate crystalline material (e.g., micronized crystalline material) the collection zone may include a cyclone collector.

In any of the embodiments described herein, the systems for conditioning a particulate crystalline material (e.g., micronized crystalline material), the system may be configured to process micronized crystalline material having a particle size ranging from about 0.1 µm to about 10 µm.

In any of the embodiments described herein, the systems for conditioning a particulate crystalline material (e.g., micronized crystalline material), the system may include a holding chamber for collecting the conditioned particles. In certain such embodiments, the system may be configured to prepare and/or deliver a secondary conditioning gas to the holding chamber and mix the secondary conditioning gas with the conditioned crystalline particles within in the holding chamber for a period of time sufficient to provide a secondary conditioning of the crystalline particles. Alternatively, in embodiments of a system for conditioning a particulate crystalline material that include a holding chamber, the holding chamber may be configured simply to receive the conditioned material or to facilitate transition of the conditioned material from a primary conditioning system to a secondary conditioning system. In any of the embodiments of the systems described herein that include a holding chamber, the holding chamber may be configured to maintain the conditioned material in a continuously fluidized state.

EXPERIMENTAL EXAMPLES

Example 1

Glycopyrrolate (3-[(cyclopentylhydroxyphenylacetyl)oxy]-1,1-dimethylpyrrolidinium bromide) was received as coarse crystalline active agent from the manufacturer (Boehringer Ingelheim Chemicals, Inc., Petersburg, Va. 23805). The glycopyrrolate (GP) was then micronized by jet milling to achieve a reduction in particle size distribution.

A portion of the micronized GP was also conditioned using an in-process conditioning system wherein nitrogen conditioning gas was supplied to the in-process conditioning system and was controlled for flow rate, temperature and humidity. The conditioning gas was humidified through a droplet evaporation chamber after which it was directed to a mixing zone. In the mixing zone, the conditioning gas was mixed with the jet-milled aerosol comprising the micronized GP. The aerosol then entered a conditioning zone where annealing of the micronized GP occurred. The particle residence time through the conditioning zone was TABLE 3-continued Particle size distributions initial and post-exposure

| Batch # | % Amorphous Content Initial | Particle Size Distribution Initial | | | | Particle Size Distribution Post-exposure | | | | Physical Stability |
|---|---|---|---|---|---|---|---|---|---|---|
| | | X10 (μm) | X50 (μm) | X90 (μm) | Span (μm) | X10 (μm) | X50 (μm) | X90 (μm) | Span (μm) | |
| 2B | 5.3% | 0.6 | 1.6 | 3.1 | 1.6 | 0.7 | 2.0 | 3.6 | 1.4 | Unstable, partially fused |
| 2C | 0.9% | 0.6 | 1.5 | 2.8 | 1.5 | 0.6 | 1.6 | 2.9 | 1.5 | Stable, no fusing |
| 2D | 0.9% | 0.6 | 1.5 | 2.7 | 1.4 | 0.6 | 1.5 | 2.8 | 1.5 | Stable, no fusing |
| 2E | 2.6% | 0.5 | 1.3 | 2.6 | 1.6 | 0.5 | 1.4 | 2.7 | 1.5 | Stable, no fusing |
| 2F | 0.9% | 0.6 | 1.5 | 2.8 | 1.5 | 0.6 | 1.6 | 2.9 | 1.5 | Stable, no fusing |
| 2G | 2.3% | 0.5 | 1.4 | 2.7 | 1.6 | 0.6 | 1.5 | 2.9 | 1.5 | Stable, no fusing |

Figure 5:
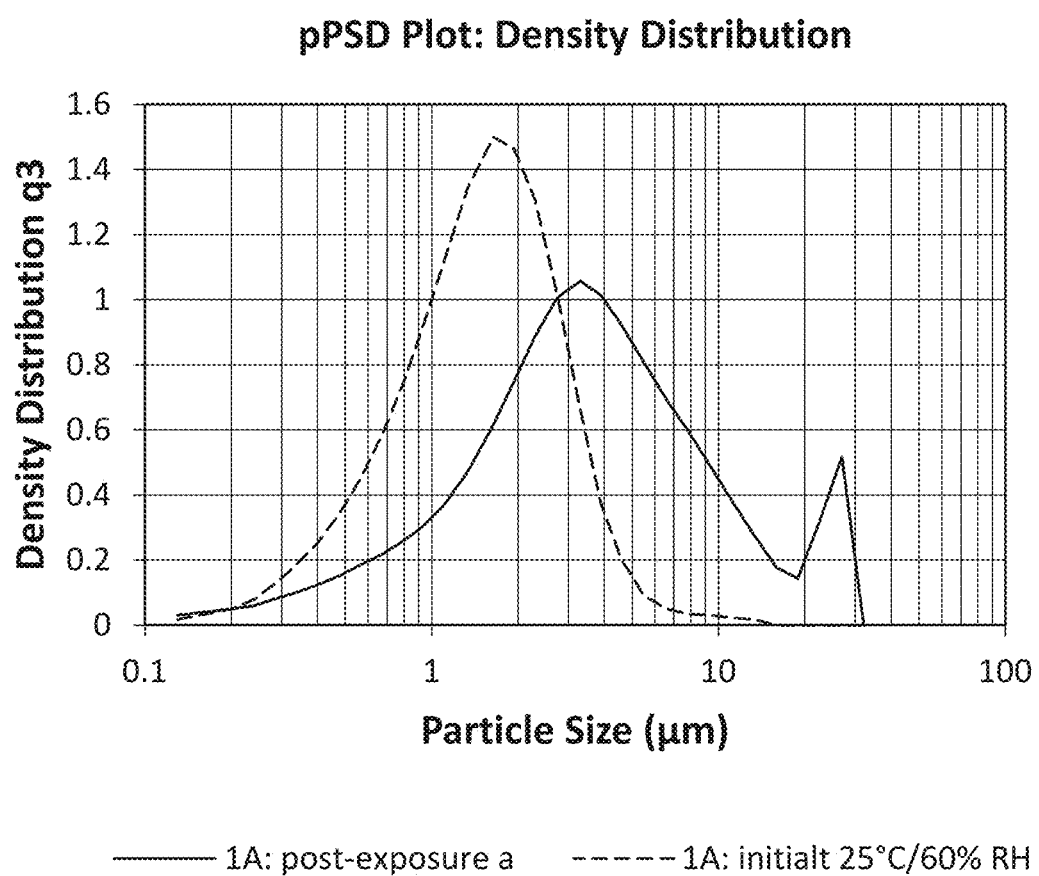
FIG. 5 is a graph depicting the unstable particle size distribution of a standard micronized glycopyrrolate sample as discussed in Example 1.

As shown in FIG. 5, analysis of the particle size distribution of the 1A control batch confirms the instability of the standard micronized GP as evidenced by the significant increase in particle size distribution of the micronized GP particles after 1-day exposure.

Figure 6A:
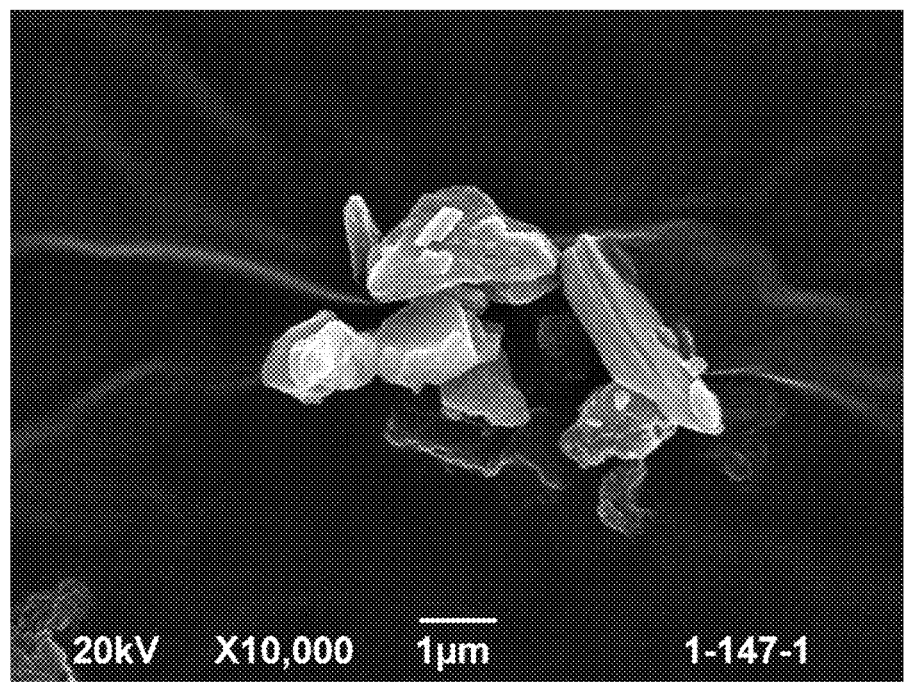
FIG. 6A is an electron micrograph showing the amorphous morphology of a standard micronized glycopyrrolate sample as discussed in Example 1.
Figure 6B:
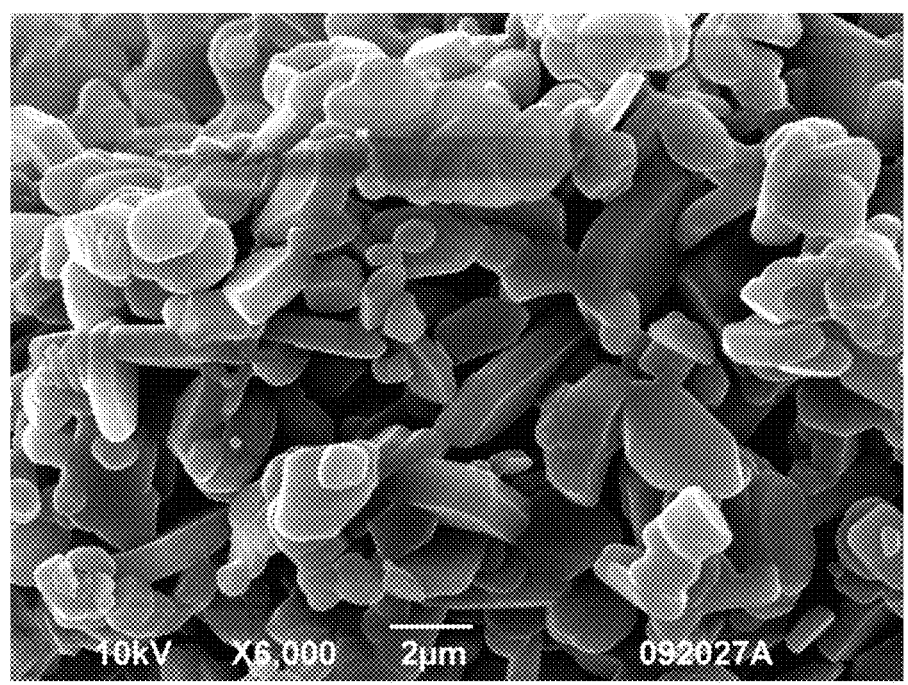
FIG. 6B is an electron micrograph showing the fusing and agglomeration of a standard micronized glycopyrrolate sample after exposure as discussed in Example 1.

FIG. 6A is an electron micrograph of the 1A control sample before exposure showing an amorphous morphology with rough surfaces and edges and increased shape variability. FIG. 6B is an electron micrograph of the 1A control sample after exposure showing that the unstable amorphous micronized GP material leads to fusing and agglomeration of the micronized GP particles.

Figure 7:
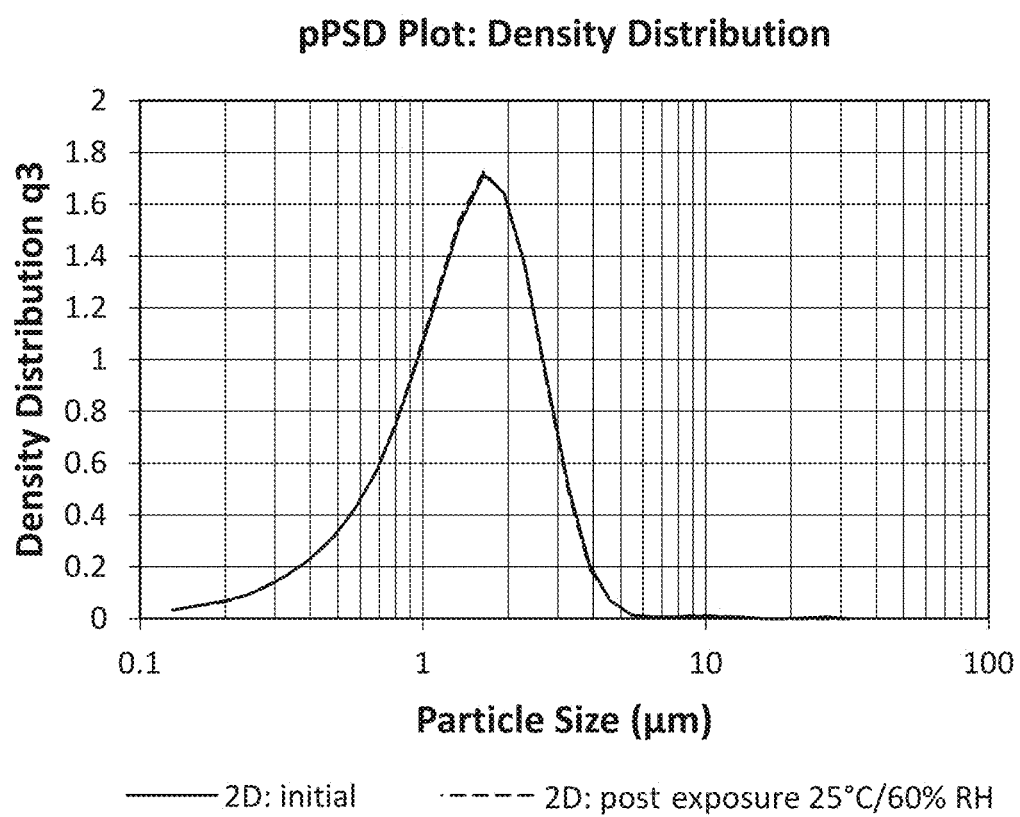
FIG. 7 is a graph depicting the stable particle size distribution of a conditioned micronized glycopyrrolate sample as discussed in Example 1.

In contrast, analysis of the 2D batch that was conditioned according to the in-process conditioning parameters as listed in Table 2, showed particle size stability. As shown in FIG. 7, the particle size distribution was essentially identical for the initial sampling and after the 1-day exposure at 25° C. and 60% relative humidity. Similar results were observed for the stability of the particle size distribution for the 2C, 2E, 2F, and the 2G samples (not shown).

Figure 8A:
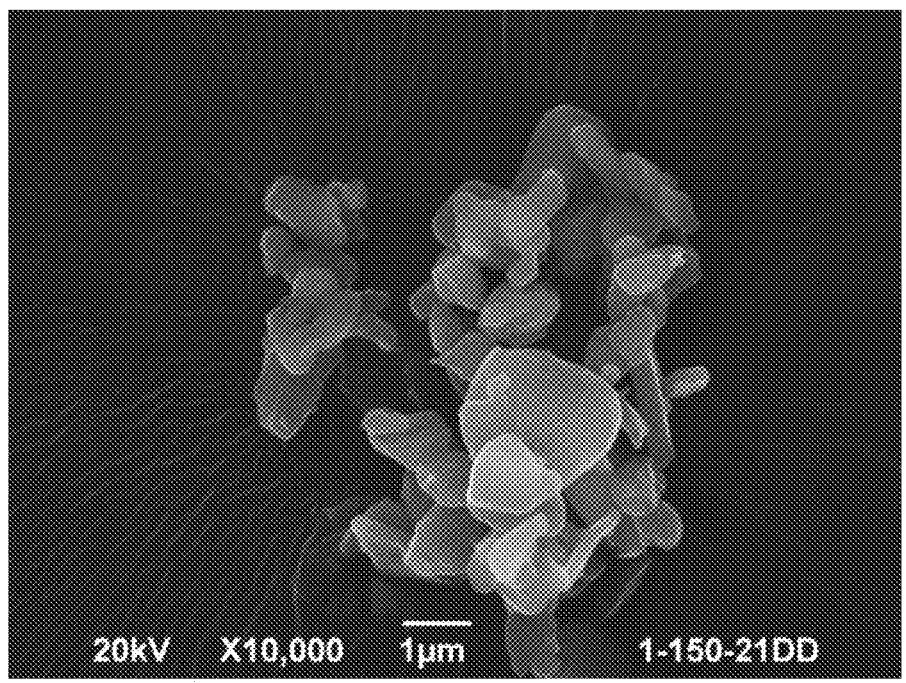
FIG. 8A is an electron micrograph showing the crystalline morphology of a conditioned micronized glycopyrrolate sample as discussed in Example 1.
Figure 8B:
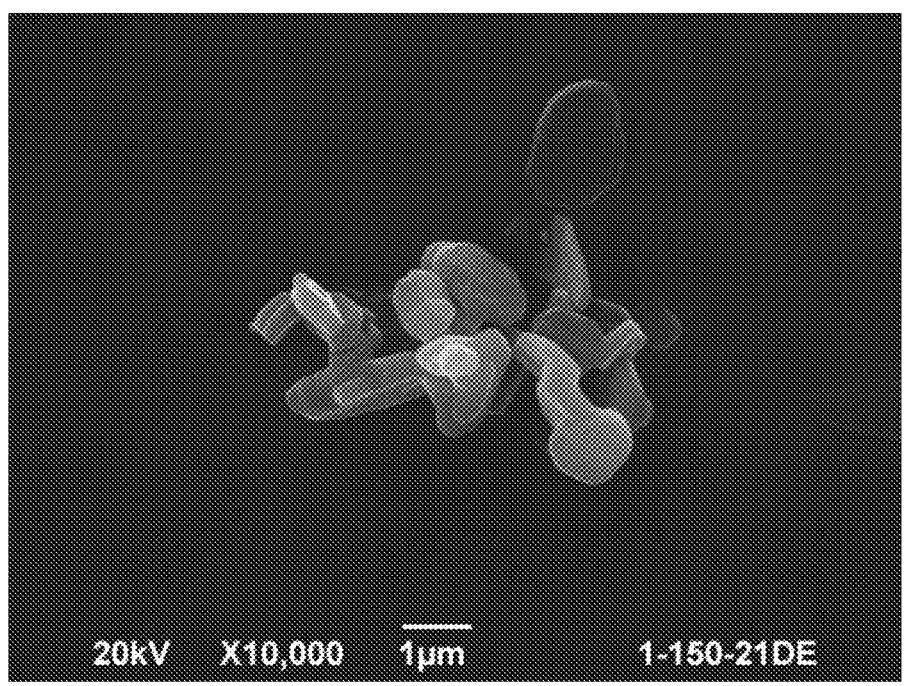
FIG. 8B is an electron micrograph showing the increased stability of a conditioned micronized glycopyrrolate sample after exposure as discussed in Example 1.

Electron micrographs of the in-process conditioned sample 2E show improved stability of conditioned micronized GP particles. As shown in FIG. 8A, the conditioned micronized GP particles show a crystalline morphology with smooth surfaces and distinct edges. As seen in FIG. 8B, the conditioned micronized GP particles show improved stability with no fusing and agglomeration even after exposure to heat and humidity. Accordingly, the in-process conditioning system disclosed herein improves micronized GP particle stability and prevents particle fusing and agglomeration.

Examples 2 & 3

Examples 2 and 3 provide examples of in-process conditioning of water insoluble molecules using a conditioning gas containing a vaporized organic solvent (ethanol) to promote annealing. Budesonide and fluticasone propionate were selected as representative compounds. The annealing conditions were determined by selecting conditions that would promote crystallization of the amorphous fraction under an ethanol atmosphere by determining the corresponding ethanol sorption isotherms.

Example 2

Budesonide (16,17-(butylidenebis(oxy))-11,21-dihydroxy-, (11-β,16-α)-pregna-1,4-diene-3,20-dione16,17-(butylidenebis(oxy))-11,21-dihydroxy-, (11-β,16-α)-pregna-1,4-diene-3,20-dione) was micronized using a laboratory scale jet mill set at 75 psig grinding pressure and 80 psig injection pressure. The crystalline budesonide was fed into the jet mill at a powder feed rate of approximately 25±10% g/hr. Two batches of micronized budesonide were produced. One was not subjected to further processing, while the second was conditioned to remove amorphous content according to the present description.

Batch 1 (unannealed/not conditioned) did not undergo any thermal or vapor conditioning. The nitrogen gas was supplied dry to the system (i.e., no organic solvents were used), and the micronized material was collected under at ambient temperature. Batch 1 was collected and transferred into a purged isolator for sampling.

Batch 2 (annealed/conditioned) was conditioned according to the present description using a conditioning gas that included an ethanol vapor, with a target of 75% relative saturation in the conditioning zone. To form the conditioning gas, ethanol (95% w/w) was atomized in nitrogen gas using a 0.21" atomizer nozzle with a set atomizer gas flow rate of 30 std. L/min (SLPM) and a liquid flow rate of 32 g/min. The conditioning gas flow rate was set to 205 SLPM with a humidifier inlet temperature of 185° C. and conditioning zone outlet of 30° C. The jet mill grind pressure was delivered at 75 psig with an injection pressure of 80 psig, resulting in a nominal micronizer gas flow rate of 122 SLPM, along with a total conditioning gas flow rate (including the atomizer gas flow) of 235 SLPM. The conditioning gas to micronizing gas (also referred to as a delivery gas) ratio (CMR) for this process configuration was 1.9:1, with a nominal total system gas flow rate of 357 SLPM. Batch 2 was collected in a 0.5 L stainless steel collector, transferred to a purged (<5% RH) isolator and sampled for analysis.

Both batches of micronized budesonide were analyzed for particle size distribution by Sympatec laser diffraction, with the results provided in Table 4. As can be seen in Table 4, Batch 2 (annealed) demonstrated good physical stability after micronization, whereas Batch 1 (unannealed) demonstrated potential agglomeration marked by a significant shift in size distribution.

TABLE 4

Particle Size Distribution of Micronized Budesonide.

| Micronized Budesonide | D10 (μm) | D50 (μm) | D90 (μm) | Span |
|---|---|---|---|---|
| Batch 1 (unannealed) | 0.6 | 2.3 | 5.4 | 2.1 |
| Batch 2 (annealed) | 0.5 | 1.2 | 2.5 | 1.7 |

Figure 9:
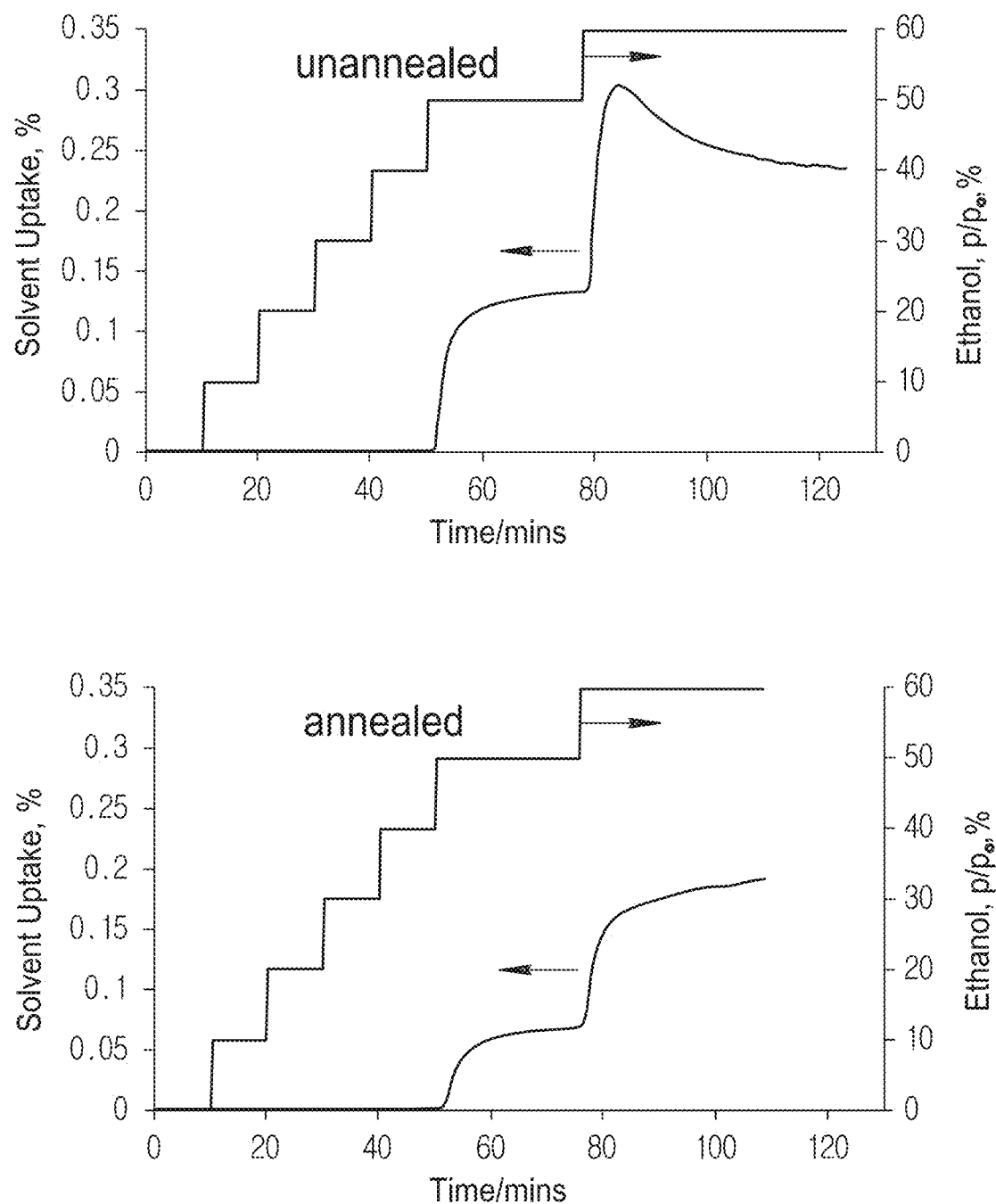
FIG. 9 provides the ethanol vapor sorption isotherm at 25° C. for micronized budesonide materials prepared in Example 2.
Figure 10:
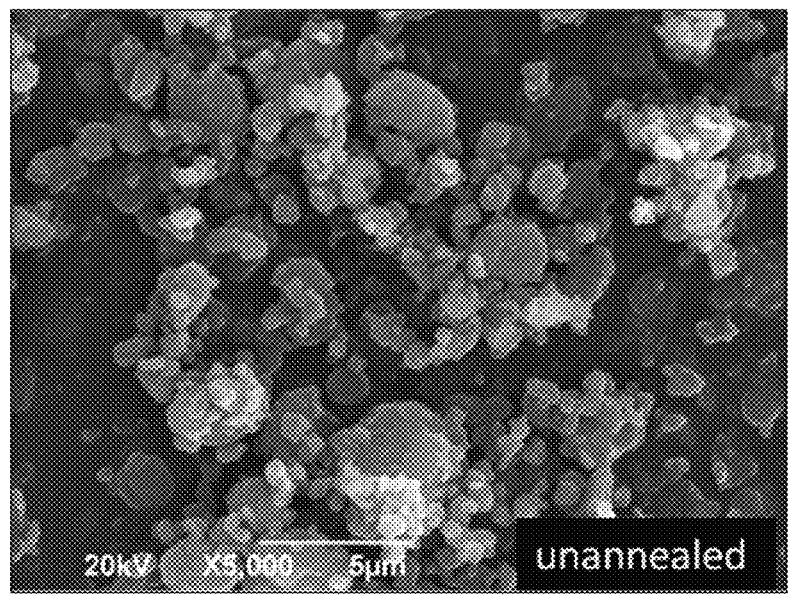
FIG. 10 includes SEM micrographs of micronized budesonide materials prepared in Example 2.
Figure 10:
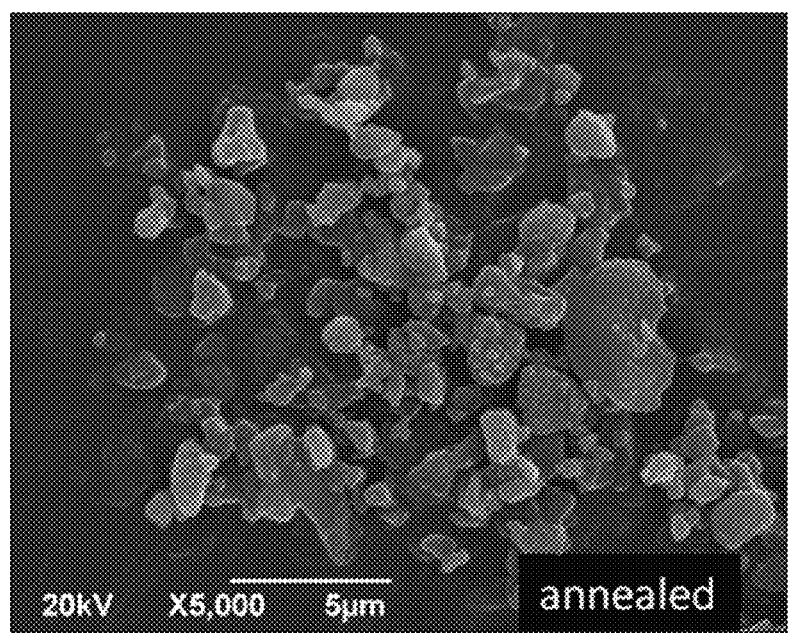

The amorphous content by vapor sorption and particle morphology for both batches were also assessed. FIG. 9 provides the ethanol vapor sorption isotherm at 25° C. for both batches of micronized budesonide. As can be seen in FIG. 9, Batch 1 (unannealed, top) remained substantially amorphous (weight loss at 60% $p/p_o$), while Batch 2 (annealed, bottom) was stable and showed no crystallization event. FIG. 10 provides SEM imaging of the material from Batch 1 and Batch 2, and as can be seen by reference to FIG. 10, the annealed material of Batch 2 (right) presented smoother surfaces and more rounded edges than the unannealed material of Batch 1 (left).

Example 3

Fluticasone propionate (S-(fluoromethyl)-6α,9-difluoro-11β, 17-dihydroxy-16α-methyl-3-oxoandrosta-1, 4-diene-17β-carbothioate, 17-propanoate) was micronized using a laboratory scale jet mill set at 65 psig grinding pressure and 74 psig injection pressure. The crystalline fluticasone was fed into the jet mill at a powder feed rate of approximately 25±10% g/hr. Two batches of micronized fluticasone were produced. One was not subjected to further processing, while the second was conditioned to remove amorphous content according to the present description.

Batch 1 (unannealed/not conditioned) did not undergo any thermal or vapor conditioning. The nitrogen gas was supplied dry to the system (i.e., no organic solvents were used), and the micronized material was collected under at ambient temperature. Batch 1 was collected and transferred into a purged isolator for sampling.

Batch 2 (annealed/conditioned) was conditioned according to the present description using a conditioning gas that included an ethanol vapor, with a target of 75% relative saturation in the conditioning zone. To form the conditioning gas, ethanol (95% w/w) was atomized in nitrogen gas using a 0.21" atomizer nozzle with a set atomizer gas flow rate of 30 std. L/min (SLPM) and a liquid flow rate of 32 g/min. The conditioning gas flow rate was set to 205 SLPM with a humidifier inlet temperature of 185° C. and conditioning zone outlet of 30° C. At the given grind and injection pressures delivered to the system, the resulting micronizer gas flow was nominally 108 SLPM, along with a total conditioning gas flow rate (including the atomizer gas flow) of 235 SLPM. The conditioning gas to micronizing gas (also referred to as a delivery gas) ratio (CMR) for this process was 2.2:1, with a total gas flow of 343 SLPM. Batch 2 was collected in a 0.5 L stainless steel collector, transferred to a purged (<5% RH) isolator and sampled for analysis.

Both batches of micronized fluticasone were analyzed for particle size distribution by Sympatec laser diffraction, with the results provided in Table 5. As can be seen in Table 5, Batch 2 (annealed) demonstrated good physical stability after micronization, whereas Batch 1 (unannealed) demonstrated agglomeration marked by a shift in size distribution.

TABLE 5

Particle Size Distribution of Micronized Fluticasone Propionate.

| Micronized Fluticasone propionate | D10 (μm) | D50 (μm) | D90 (μm) | Span |
|---|---|---|---|---|
| Batch 1 (unannealed) | 0.5 | 1.5 | 3.4 | 2.0 |
| Batch 2 (annealed) | 0.5 | 1.4 | 3.1 | 1.9 |

Figure 11:
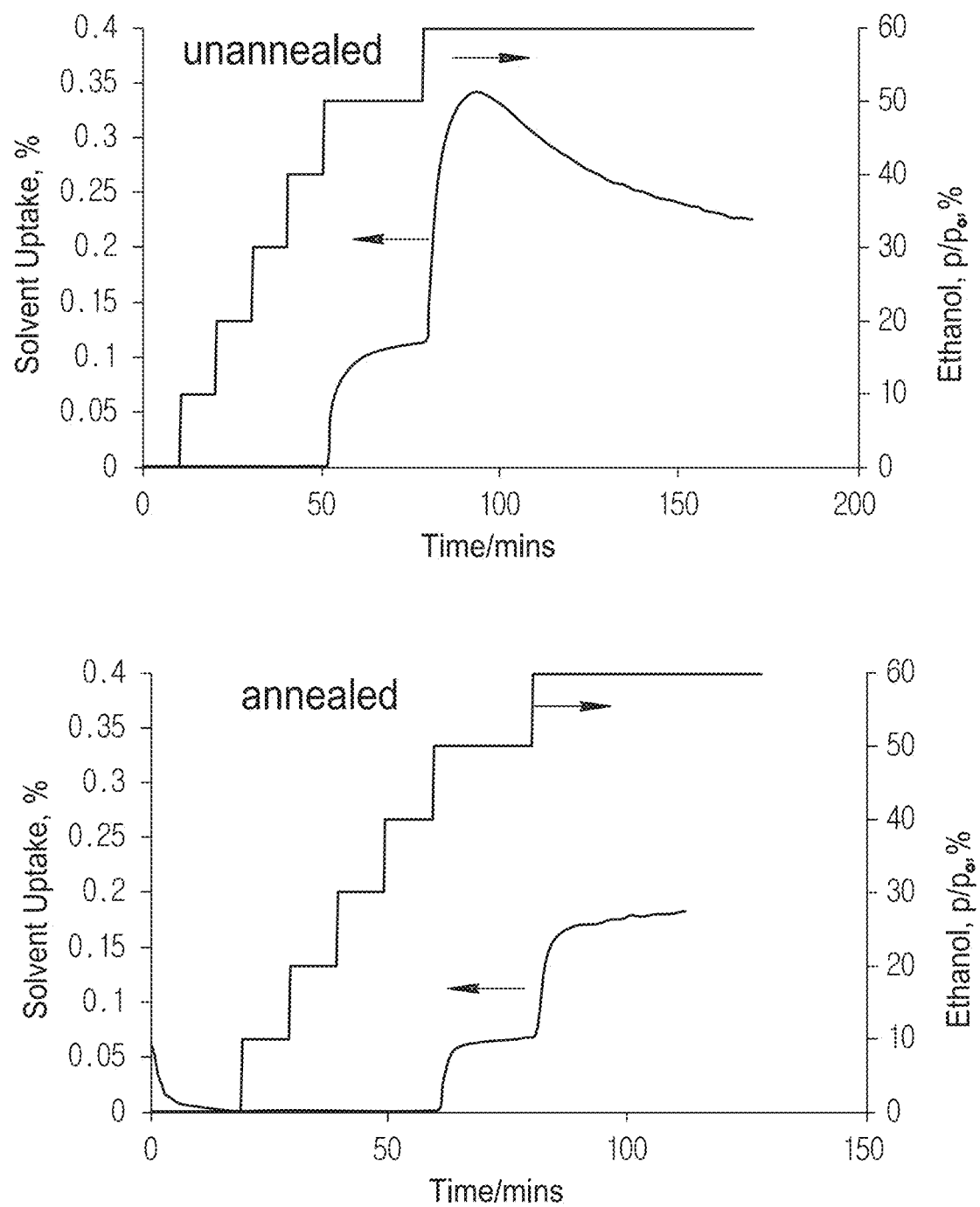
FIG. 11 provides the ethanol vapor sorption isotherm at 25° C. for micronized fluticasone propionate materials prepared in Example 3.
Figure 12:
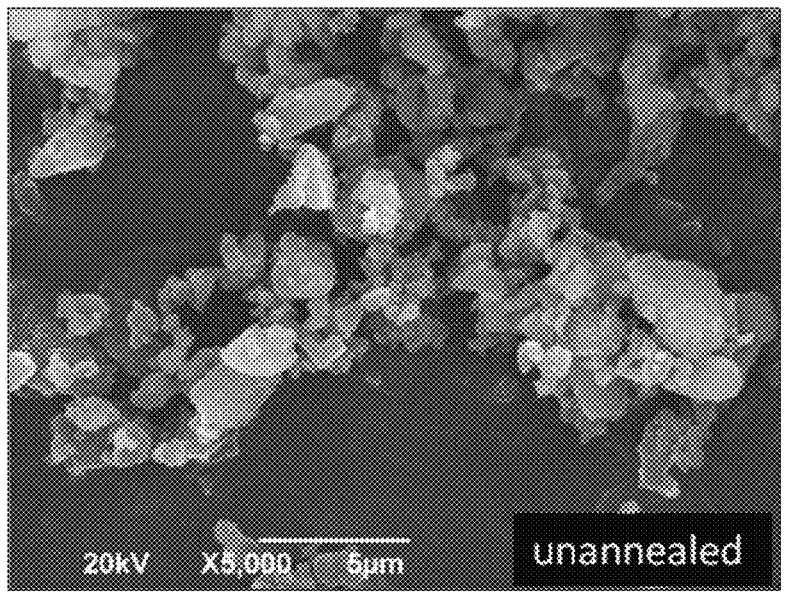
FIG. 12 includes SEM micrographs of micronized fluticasone materials prepared in Example 3.
Figure 12:
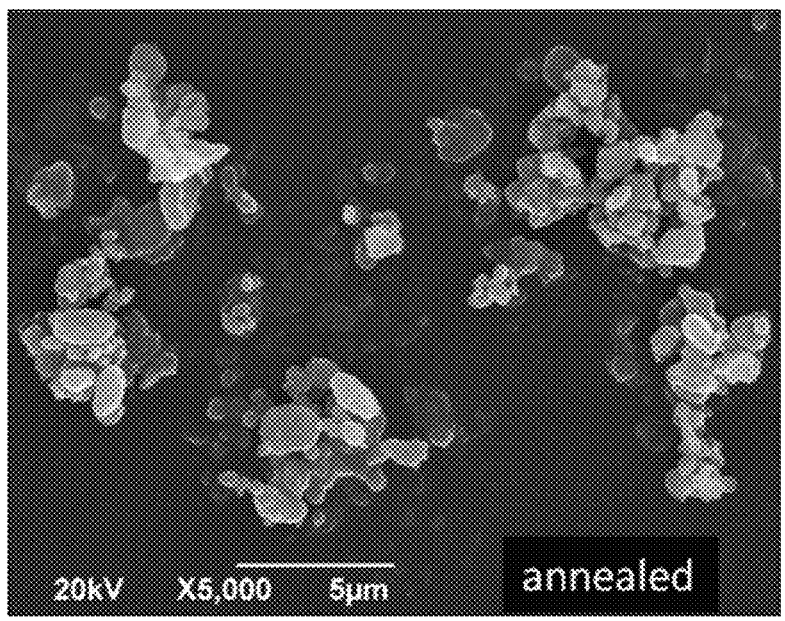

The amorphous content by vapor sorption and particle morphology for both batches were also assessed. FIG. 11 provides the ethanol vapor sorption isotherm at 25° C. for both batches of micronized fluticasone. As can be seen in FIG. 11, Batch 1 (unannealed, top) remained substantially amorphous (weight loss at 60% $p/p_o$), while Batch 2 (annealed, bottom) was stable and showed no crystallization event. FIG. 12 provides SEM imaging of the material from Batch 1 and Batch 2, and as can be seen by reference to FIG. 10, the annealed material of Batch 2 (right) presented smoother surfaces and more rounded edges than the unannealed material of Batch 1 (left).

Example 4

Three scale-up batches of micronized glycopyrrolate (GP) were produced via a large-scale in-process micronization and conditioning system according to the present description that utilized a two-collector process at approximately 1 kg per batch. The first two lots were manufactured using a single, raw crystalline API lot, while the third used a different lot from the same vendor. All batches were produced on different dates using the same process configuration that utilized the same 4" jet mill, and the same conditioning environment (i.e., a target of 55% RH at 40° C. conditioning zone outlet temperature).

The system was brought to steady-state equilibrium, with the jet mill operating at 68 psig injection pressure and 48 psig grind pressure for a micronizer gas flow of approximately 36 SCFM. Again, the micronizer gas also served as the delivery gas for the micronized material. The conditioning gas flow rate was supplied at approximately 78 SCFM with a humidifier outlet temperature of 57° C. Water was delivered to the 0.21" atomizer nozzle at a liquid flow rate of 75.1 ml/min. The conditioning to micronization gas ratio (CMR) was set at 2.2:1. Product was collected in 8 L stainless steel collectors, which were heated using a thermal jacket to prevent the collector environment from falling below the dew-point temperature.

Once the system reached steady-state, powder was fed into the jet mill at a nominal rate of 1 kg/hr. A collector change-out was performed half way through each run with a collector purging step before each change-out to obviate the risk of any post-process affects due to residual vapor. The collectors were transferred to a purged isolator (<5% RH) for sampling and packaging to prevent any post-process affects due to ambient moisture.

All batches were analyzed for particle size distribution by Sympatec laser diffraction, with the results provided in Table 6. n=3 replicates per collector were assessed (mean values are shown). As can be seen in Table 6, the particle size distribution achieved in each batch exhibited good batch to batch reproducibility.

TABLE 6

Particle Size Distribution of Micronized/Annealed GP

| Micronized/Annealed Glycopyrrolate | D10 (μm) | D50 (μm) | D90 (μm) | Span |
|---|---|---|---|---|
| Batch A - Collector 1 | 0.52 | 1.48 | 3.02 | 1.68 |
| Batch A - Collector 2 | 0.52 | 1.47 | 2.99 | 1.69 |
| Batch B - Collector 1 | 0.52 | 1.47 | 3.02 | 1.70 |
| Batch B - Collector 2 | 0.52 | 1.46 | 2.99 | 1.70 |
| Batch C - Collector 1 | 0.52 | 1.47 | 3.03 | 1.70 |
| Batch C - Collector 2 | 0.51 | 1.45 | 2.96 | 1.69 |

All batches were also analyzed for amorphous content by dynamic vapor sorption using n=2 replicates per collector. The results are provided in Table 7, which reflects that the amorphous content achieved in each batch also exhibited good batch to batch reproducibility.

TABLE 7

Amorphous Content of Conditioned GP

| Micronized/Annealed GP | Calculated Amorphous Content, Collector 1 | Calculated Amorphous Content, Collector 2 |
|---|---|---|
| Batch A | 2.65% | 2.35% |
| Batch B | 2.65% | 2.40% |
| Batch C | 2.65% | 2.45% | psig. Identical lots of the raw input material were used for dispensing both batches. Process conditions for each batch are provided in Table 8.

Sucrose A (unannealed/not conditioned) did not undergo any thermal or vapor conditioning. The nitrogen gas was supplied dry to the system, and the system was run at ambient temperature. The jet mill was operated at 80 psig injection pressure and 70 psig grind pressure for a nominal micronizer gas flow of approximately 45.0 SCFM. The conditioning gas flow rate (ambient temperature, 0% RH) was supplied at approximately 61.0 SCFM. The conditioning to micronizing gas Ratio (CMR) was set at 1.4:1. Product was collected in 8 L stainless steel collectors, without the use of a thermal jacket.

Powder was fed into the jet mill at a nominal feed rate of 0.5 kg/hr. A collector change-out was performed half way through each run. The collectors were transferred to a purged isolator (<5% RH) for sampling and packaging to prevent any post-process affects due to ambient moisture.

Sucrose B (annealed/conditioned) was conditioned at a target 55% relative humidity at 40° C. conditioning zone outlet temperature. The system was brought to steady-state equilibrium, with the jet mill operating at 80 psig injection pressure and 76 psig grind pressure for a nominal micronizer gas flow of approximately 49.4 SCFM. The conditioning gas flow rate was supplied at approximately 61.8 SCFM with a humidifier outlet temperature of 157.2° C. Water was delivered to a 0.21" atomizer nozzle at a liquid flow rate of 76.2 ml/min. The conditioning to micronizing gas Ratio (CMR) was set at 1.4:1. Product was collected in 8 L stainless steel collectors, which were heated using a thermal jacket to prevent the collector environment from falling below the dew-point temperature.

Once the system reached steady state, powder was fed into the jet mill at a rate of 0.5 kg/hr. A collector change-out was performed half way through each run, including a system purge-out step prior to each change-out to obviate the risk of any post-process affects due to residual vapor. The collectors were transferred to a purged isolator (<5% RH) for sampling and packaging to prevent any post-process affects due to ambient moisture.

TABLE 8

Process Conditions for Production of Micronized Sucrose Batches.

| Batch # | Nominal Powder Feed Rate kg/hr | Jet Mill Grind Pressure psi | Jet Mill Injection Pressure psi | Nominal Micronizer Flow Rate SCFM | CMR | Nominal Conditioning Gas Flow Rate SCFM | Approx. Liquid Flow Rate ml/min | Target Conditioning ° C./% RH |
|---|---|---|---|---|---|---|---|---|
| Sucrose A | 0.5 | 70 | 80 | 45.2 | 1.4 | 61.0 | N/A | 18/0 |
| Sucrose B | 0.5 | 76 | 80 | 49.4 | 1.4 | 61.8 | 76.2 | 40/55 |

Example 5

Sucrose (saccharose; α-D-glucopyranosyl-(1→2)-β-D-fructofuranoside) was micronized and conditioned using the large scale micronization/annealing system utilized in Example 4. Particulate sucrose was delivered to the 4" jet mill at a nominal powder feed rate of 0.5 kg/hr. Two batches of micronized sucrose were produced. For the first, the 4" jet mill was set at an 80 psig injection pressure and a grind pressure of 70 psig. For the second, the 4" jet mill was set at an 80 psig injection pressure and a grind pressure of 76

Figure 15:
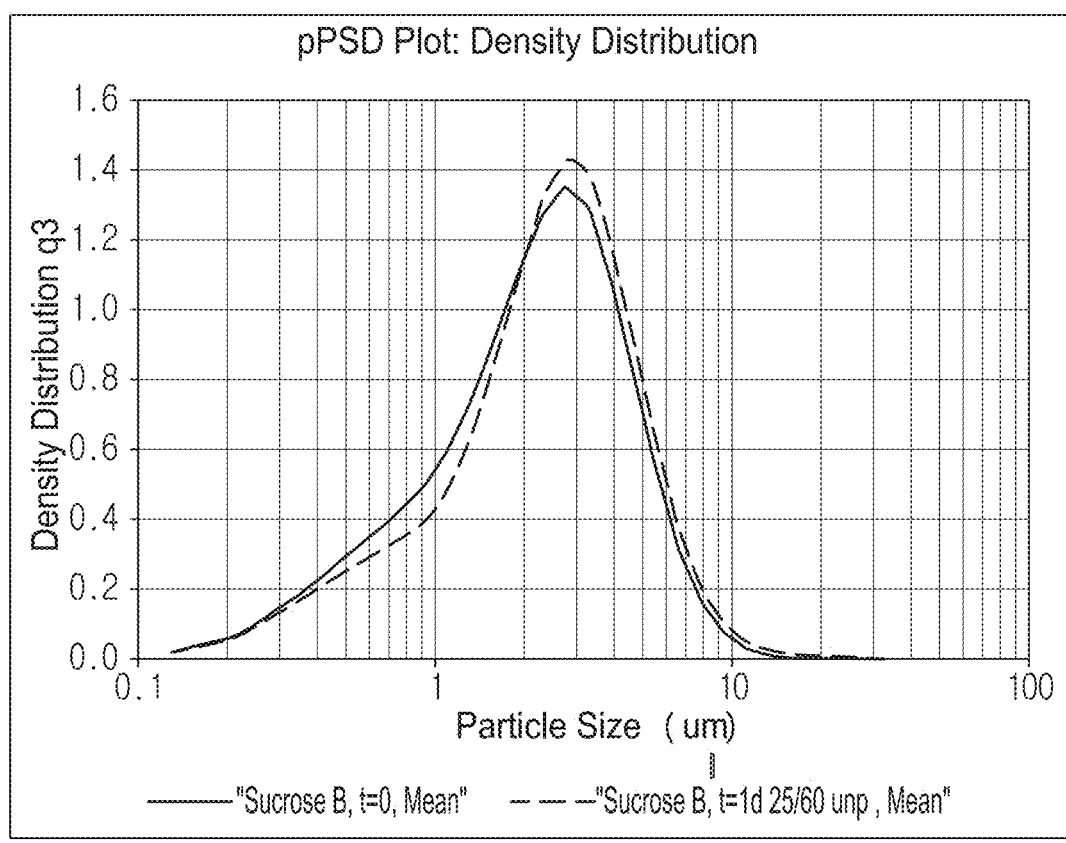
FIG. 15 provides a graph illustrating the particle size distribution of micronized, conditioned sucrose material prepared in Example 4.

Both micronized sucrose batches were analyzed for particle size distribution by Sympatec laser diffraction. The results of the analysis are provided in Table 9 and FIG. 15. Sucrose A was not tested after exposure, however fusing of the material on stability was confirmed by visual observation, demonstrating an unstable powder. Sucrose B was exposed to a 25° C./60% RH environment and showed good stability even post-exposure. FIG. 15 shows the particle size distribution observed in Sucrose B after it was freshly made and then after exposed to a 25° C./60% RH environment.

TABLE 9

Particle Size Distribution of Micronized Sucrose

| Batch # | Particle Size Distribution Initial | | | | Particle Size Distribution T = 1 day at 25° C./60% RH | | | | Physical Stability |
|---|---|---|---|---|---|---|---|---|---|
| | X10 (μm) | X50 (μm) | X90 (μm) | Span (μm) | X10 (μm) | X50 (μm) | X90 (μm) | Span (μm) | |
| Sucrose 1 | 0.5 | 1.7 | 4.5 | 2.4 | NT | NT | NT | NT | Unstable, fused |
| Sucrose 2 | 0.6 | 2.2 | 4.9 | 1.9 | 0.7 | 2.5 | 5.2 | 1.9 | Stable, no fusing |

Figure 13:
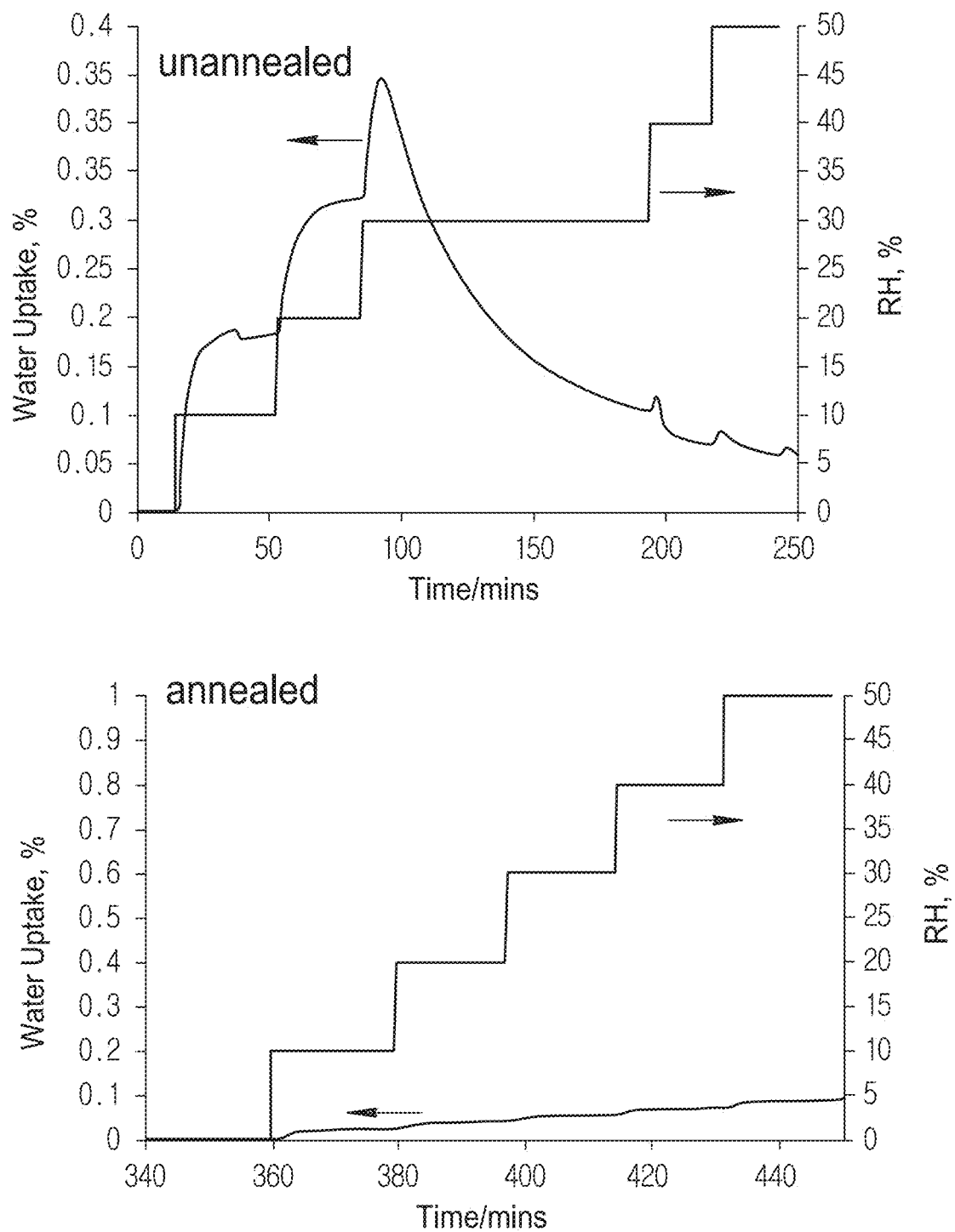
FIG. 13 provides the water vapor sorption isotherm at 25° C. for micronized sucrose materials prepared in Example 4.
Figure 14:
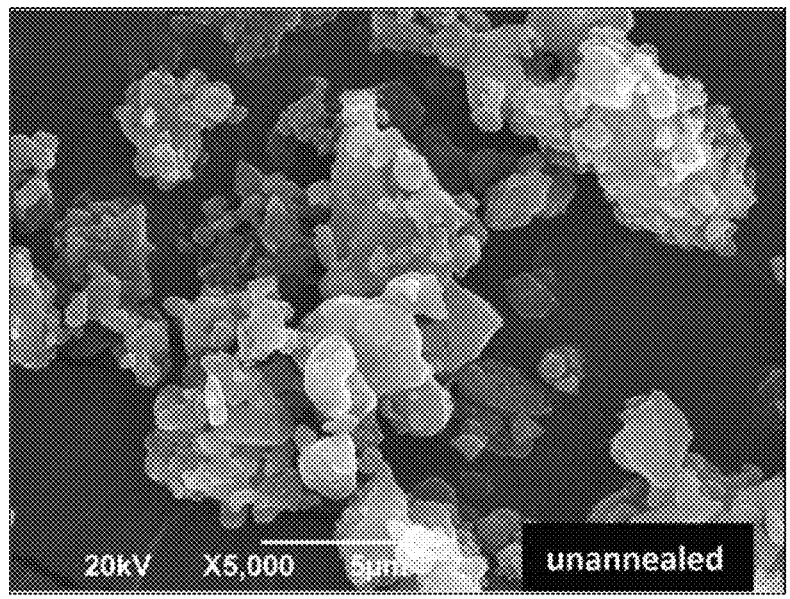
FIG. 14 includes SEM micrographs of micronized sucrose materials prepared in Example 4.
Figure 14:
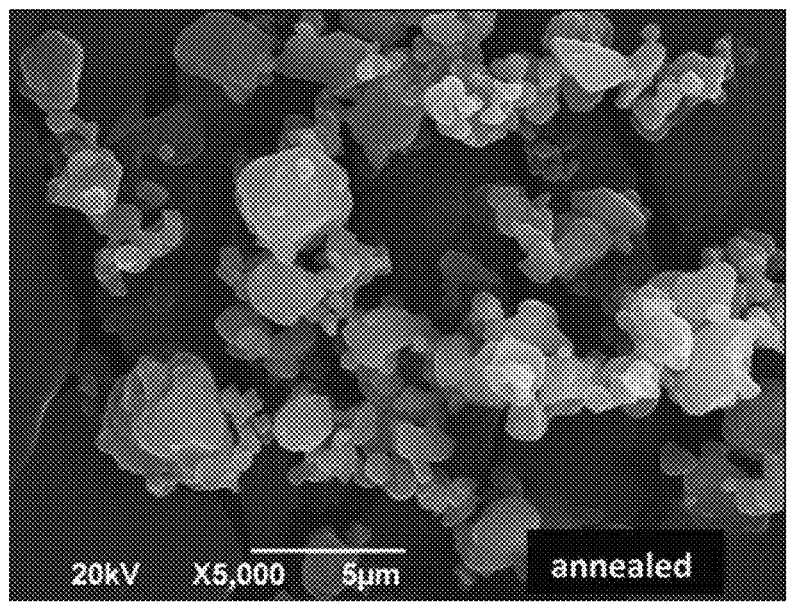

The amorphous content by vapor sorption and particle morphology for both batches of micronized sucrose were also assessed. FIG. 13 provides the water vapor sorption isotherm at 25° C. for both batches of micronized sucrose. As can be seen in FIG. 13, Sucrose A (unannealed, top) remained substantially amorphous (weight loss at 30% $p/p_o$), while Sucrose B (annealed, bottom) was stable and showed no crystallization event. FIG. 14 provides SEM imaging of the material from Sucrose A and Sucrose B, and as can be seen by reference to FIG. 14, the annealed material of Sucrose B (right) presented smoother surfaces and more rounded edges than the unannealed material of Sucrose A (left).

Example 6

Compound A, a novel bi-functional muscarinic antagonist and beta2 agonist (IUPAC: 7-[(1R)-2-[2-[2-fluoro-5-[[4-(2-isopropylthiazole-4-carbonyl)-1-oxa-4,9-diazaspiro[5.5]undecan-9-yl]methyl]phenyl]ethylamino]-1-hydroxy-ethyl]-4-hydroxy-3H-1,3-benzothiazol-2-one; di[[(1S,4R)-7,7-dimethyl-2-oxo-norbornan-1-yl]methanesulfonic acid] salt), was selected for micronization and subsequent solvent removal using primary and secondary conditioning steps. Compound A retained ~5% residual isopropyl alcohol solvent after manufacture. Compound A was micronized and conditioned using an in-process conditioning system according to the present description that included a 1" jet mill. Process conditions were selected to promote solvent exchange to reduce or remove residual isopropyl alcohol and replace the isopropyl alcohol either directly with water or with ethanol and secondarily with water. Three batches of micronized Compound A were produced as described in Table 10 below. Identical lots of the raw input material were used for dispensing all three batches.

TABLE 10

| Batch Description | Nominal Powder Feed rate g/hr | Jet Mill Grind Pressure psi | Jet Mill Injection Pressure psi | Temp ° C. | % Relative Sat. % RS | Batch Yields % |
|---|---|---|---|---|---|---|
| No Conditioning | 25 ± 2 | 70 | 80 | 21 | 0 | 49% |
| 29° C./69% RH | 25 ± 2 | 70 | 80 | 29 | 69 | 62% |
| 30 C./53% RS (ethanol) | 25 ± 2 | 70 | 80 | 30 | 53 | 53% |

Batch 1 (unannealed) did not undergo any thermal or vapor conditioning. The nitrogen gas was supplied dry to the system and ran at ambient temperature (i.e., no heat or solvent vapor was used). The total conditioning gas flow rate was 255 SLPM. The micronization gas flow rate was about 110 SLPM at the given milling pressures, giving a conditioning to micronization gas Ratio (CMR) of 2.3:1 and total gas flow of 365 SLPM. Batch 1 was collected and transferred into a purged isolator for sampling.

Batch 2 (conditioned with water vapor at 29° C./69% RH) was conditioned using a conditioning gas that provided water vapor at 69% relative humidity (RH) in the conditioning zone. The conditioning gas was formed by atomizing water in nitrogen gas using a 0.21" atomizer nozzle, with a set atomizer gas flow rate of 35 std. L/min (SLPM) and a liquid flow rate of 7 g/min. The conditioning gas flow rate was set to 220 SLPM with a humidifier inlet temperature of 100° C. and conditioning zone outlet of 29° C. The total conditioning gas flow rate including the atomizer was 255 SLPM. The micronization gas flow rate was about 110 SLPM at the given milling pressures, giving a conditioning to micronization gas Ratio (CMR) of 2.3:1 and total gas flow of 365 SLPM. Batch 2 was collected in a 0.5 L stainless steel collector, transferred to a purged (<5% RH) isolator and sampled for analysis.

Batch 3 (primary conditioning with ethanol at 30° C./53% RS; secondary conditioning with water at 30° C./67% RH) was conditioned using a conditioning gas including ethanol vapor, with a target of 75% relative saturation in the conditioning zone. The conditioning gas was formed by atomizing ethanol (95% w/w) in nitrogen gas using a 0.21" atomizer nozzle, with a set atomizer gas flow rate of 35 std. L/min (SLPM) and a liquid flow rate of 28 g/min. The conditioning gas flow rate was set to 220 SLPM with a humidifier inlet temperature of 150° C. and conditioning zone outlet of 30° C. The micronization gas flow rate was about 110 SLPM at the given milling pressures, giving a conditioning to micronization gas Ratio (CMR) of 2.3:1 and total gas flow of 365 SLPM. Upon completion of condition ing with ethanol, ethanol liquid flow was stopped, and the process was adjusted to provide a conditioning gas containing water vapor. The humidifier inlet temperature of 100° C. was set and water was then fed into the system at a flow rate of 7 g/min at a CZ outlet temperature and collector temperature of 30° C. The material was secondarily conditioned in the collector with a conditioning gas containing water vapor at 67% RH. Batch 3 was collected in a 0.5 L stainless steel collector, transferred to a purged (<5% RH) isolator and sampled for analysis.

All three batches were analyzed for particle size distribution by Sympatec laser diffraction, with the results shown in Table 11. Particle Size Distribution of conditioned Compound A demonstrates good reproducibility, and the particle size distribution of the conditioned Compound A is consistent with the unannealed micronized material.

TABLE 11

| Compound A, PSD | D10 (μm) | D50 (μm) | D90 (μm) |
|---|---|---|---|
| Raw (Un-milled) | 1.1 | 3.7 | 16.3 |
| Unannealed | 0.6 | 1.6 | 3.1 |
| 30° C./70% RH | 0.6 | 1.6 | 3.1 |
| 30° C./55% RS (ethanol); 30° C./70% RH (water) | 0.6 | 1.7 | 3.2 |

Residual solvent content of the material from different batches was also analyzed. Table 12 shows the residual solvent content of materials from each batch as assessed by GC analysis. Residual solvent is partially removed using primary (ethanol) and secondary (water) conditioning. Material that was treated using a secondary conditioning process exhibited increased replacement of the IPA.

TABLE 12

| Compound A Batches | % IPA (w/w) | % EtOH (w/w) | % Water |
|---|---|---|---|
| Raw (un-milled) | 4.7% | 0.0% | 3.1% |
| Unannealed | 3.9% | 0.2% | 3.0% |
| 30° C./70% RH | 3.6% | 0.1% | 3.4% |
| 30° C./55% RS; 30° C./70% RH | 2.1% | 1.2% | 3.4% |

Example 7

Compound A (IUPAC: 7-[(1R)-2-[2-[2-fluoro-5-[[4-(2-isopropylthiazole-4-carbonyl)-1-oxa-4,9-diazaspiro[5.5]undecan-9-yl]methyl]phenyl]ethylamino]-1-hydroxy-ethyl]-4-hydroxy-3H-1,3-benzothiazol-2-one; di[[(1S,4R)-7,7-dimethyl-2-oxo-norbornan-1-yl]methanesulfonic acid] salt) was received with a 3.8% ethanol residual content. This material had been previously micronized and conditioned according to the present description to reduce the presence of isopropyl (IPA) and ethanol (EtOH) by solvent exchange/removal. The material was exposed to another conditioning gas that included water vapor, and was mixed with the conditioning gas in a conditioning zone for approximately 1.5 hours. As shown in Table 13, residual IPA and EtOH was nearly completely removed and water content of the material increased.

TABLE 13

| Micronized Compound A Batch | % IPA (w/w) | % EtOH (w/w) | % Water |
|---|---|---|---|
| As Received | 0.1% | 3.8% | 3.1% |
| 30° C./70% RH (water) | 0.0% | 0.1% | 3.6% |

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including but not limited to U.S. Provisional Application No. 61/799,956, filed Mar. 15, 2013, are incorporated herein by reference, in their entirety. Aspects of the embodiments can be modified, if necessary to employ concepts of the various patents, applications and publications to provide yet further embodiments.

The invention claimed is:

1. A method of conditioning micronized crystalline particles comprising corticosteroid, long-acting muscarinic agent, or short-acting beta-agonist, or a salt thereof, wherein at least one of the micronized crystalline particles comprises an amorphous region and/or a residual solvent, the method comprising:

aerosolizing the micronized crystalline particles;

continuously mixing the micronized crystalline particles with a conditioning gas comprising a carrier gas and a conditioning vapor in a chamber, wherein the conditioning gas is provided at a temperature exceeding the glass transition temperature (Tg) of the amorphous region of the at least one micronized crystalline particle by about 20° C. and at a relative humidity to promote annealing of the at least one micronized crystalline particle;

maintaining the aerosolized micronized crystalline particles in contact with the conditioning gas for between about 0.1 to 600 seconds to result in annealing of the at least one micronized crystalline particle, wherein said annealing results in one or both of reducing the presence of amorphous region or reduction in the amount of residual solvent; and separating the micronized crystalline particles from the conditioning gas.

2. The method of claim 1, wherein the micronized crystalline particles are water soluble, the solvent vapor included in the conditioning gas is an aqueous solvent vapor, and the conditioning gas is provided at a temperature ranging from 20° C. to 100° C. and at a relative humidity ranging from 0.05% to 95%.

3. The method of claim 1, wherein the micronized crystalline particles are not water soluble, the solvent vapor included in the conditioning gas is an organic solvent vapor, and the conditioning gas is provided at a temperature ranging from 20° C. to 100° C. and at a relative saturation of a non-aqueous solvent in the range of 0.05% to 95%.

4. The method of claim 1, wherein the micronized crystalline particles are an admixture of water soluble and non-water soluble materials, the solvent vapor included in the conditioning gas comprises an aqueous solvent vapor and an organic solvent vapor, and the conditioning gas is supplied at a temperature ranging from 10° C. to 100° C. and at a relative humidity of the aqueous solvent in the range of 0.05% to 95% and a relative saturation of the non-aqueous solvent in the range of 0.05% to 95%.

5. The method of claim 1, wherein the micronized crystalline particles are produced using a jet mill and are aerosolized in the jet mill gas flow.

6. The method of claim 1, wherein the conditioning gas is mixed with the aerosolized micronized crystalline particles in a ratio of 1 to 10 parts conditioning gas with 1 part of the aerosolized micronized crystalline particles.

7. The method of claim 1, wherein the conditioning gas is supplied at a flow rate ranging from 25 standard cubic feet per minute (SCFM) up to 300 SCFM while mixing with the micronized crystalline particles.

8. The method of claim 1, wherein the aerosolized micronized crystalline particles are supplied at a flow rate ranging from 25 standard cubic feet per minute (SCFM) up to 200 SCFM while mixing with the conditioning gas.

9. The method of claim 1, wherein the conditioning gas comprises nitrogen gas.

10. The method of claim 1, wherein the micronized crystalline particles are mixed with the conditioning gas in a closed chamber.

11. The method of claim 1, wherein the micronized crystalline particles comprise glycopyrrolate.

12. The method of claim 1, wherein the micronized crystalline particles comprise budesonide.

13. A system for in-process conditioning of micronized crystalline particles comprising corticosteroid, long-acting muscarinic agent, or short-acting beta-agonist, or a salt thereof, wherein at least one of the micronized crystalline particles comprises an amorphous region and/or a residual solvent, the system comprising:
  a micronizing zone comprising a device for micronizing the crystalline particles;
  a mixing zone in fluid communication with the micronizing zone, wherein the micronized crystalline particles are delivered from the micronizing zone to the mixing zone and therein mixed with a conditioning gas;
  a conditioning gas supply zone in fluid communication with the mixing zone, the conditioning gas supply zone providing the conditioning gas at a desired temperature and solvent vapor concentration to the mixing zone to be mixed with the micronized crystalline particles;
  a conditioning zone in fluid communication with the mixing zone, wherein the mixture of the micronized crystalline particles and the conditioning gas is delivered and remains in the conditioning zone for a desired residence time, and wherein the conditioning gas is provided at a temperature exceeding the glass transition temperature (Tg) of the amorphous region of the at least one micronized crystalline particle by about 20° C. and at a relative humidity to promote annealing of the at least one micronized crystalline particle;
  a separation and collection zone, wherein the conditioned micronized crystalline particles are separated from the conditioning gas and the conditioned active agent is collected.

14. The system of claim 13, wherein the micronized crystalline particles are water soluble and the conditioning gas supply zone is configured to provide the conditioning gas at a temperature ranging from 20° C. to 100° C. and at a humidity ranging from 0.05% to 90% relative humidity.

15. The system of claim 13, wherein the micronized crystalline particles are not water soluble and the conditioning gas supply zone is configured to provide the conditioning gas at a temperature ranging from 20° C. to 100° C. and at a relative saturation of a non-aqueous solvent in the range of 0.05% to 90% in the flowing conditioning gas stream.

16. The system of claim 13, wherein the micronized crystalline particles are an admixture of water soluble and non-water soluble materials, and the conditioning gas supply zone is configured to provide the conditioning gas at a temperature ranging from 20° C. to 30° C. and at a relative humidity of 50 to 75% and a relative saturation of a non-aqueous solvent in the range of 50% to 75% in the flowing conditioning gas stream.

17. The system of claim 13, wherein the conditioning gas supply zone is configured to provide the conditioning gas at a temperature of about 25° C. and with a humidity of about 65% relative humidity.

18. The system of claim 13, wherein the conditioning zone is configured to maintain the mixture of the micronized crystalline particles and the conditioning gas within the conditioning zone for a residence time of between about 0.5 to 60 seconds.

19. The system of claim 13, wherein the conditioning zone is configured to maintain the mixture of the micronized crystalline particles and the conditioning gas within the conditioning zone for a residence time of between about 1 to about 10 seconds.

20. The system of claim 13 wherein the conditioning zone is configure to maintain the mixture of the micronized crystalline particles and the conditioning gas within the conditioning zone for a residence time of about 3 seconds.

21. The system of claim 13, wherein the micronizing zone comprises a jet mill configured for micronizing the crystalline particles.

22. The system of claim 13, wherein the conditioning gas supply zone is configured to provide the conditioning gas to the mixing zone at a flow rate ranging from 150 standard cubic feet per minute (SCFM) up to 300 SCFM.

23. The system of claim 13, wherein the micronizing zone is configured to deliver the micronized crystalline particles as an aerosolized particulate material to the mixing zone at a flow rate ranging from 35 standard cubic feet per minute (SCFM) up to 200 SCFM.

24. The system of claim 13, wherein the mixing zone comprises a dispersion head assembly, and wherein the conditioning gas and the micronized crystalline particles are mixed in the dispersion head assembly.

25. The system of claim 24, wherein the dispersion head assembly comprises a mixing head configured to control the mixing of the conditioning gas and the micronized crystalline particles.

26. The system of claim 25, wherein the mixing head comprises an injection nozzle inlet configured to deliver the conditioning gas to an injection nozzle, and wherein the mixing head comprises a delivery gas inlet configured to deliver the micronized crystalline material to the injection nozzle, and wherein the injection nozzle is configured for mixing the conditioning gas with the micronized crystalline particles.

27. The system of claim 13, wherein the residence time in the conditioning zone of the mixture of the micronized crystalline particles and the conditioning gas may be modified by adjusting the geometry of the conditioning zone.

28. The system of claim 13, wherein the residence time in the conditioning zone of the mixture of the micronized crystalline particles and the conditioning gas may be modified by adjusting the rate at which the mixture of the micronized crystalline particles and the conditioning gas is delivered from the mixing zone to the conditioning zone.

29. The system of claim 13, wherein the separation and collection zone comprises a cyclone collector.

* * * * *